(12) United States Patent
Harding et al.

(10) Patent No.: US 9,051,351 B2
(45) Date of Patent: *Jun. 9, 2015

(54) HEPATOCYTE GROWTH FACTOR MIMICS AS THERAPEUTIC AGENTS

(71) Applicant: Washington State University, Pullman, WA (US)

(72) Inventors: Joseph W. Harding, Pullman, WA (US); John W. Wright, Pullman, WA (US); Caroline C. Benoist, Nashville, TN (US); Leen H. Kawas, Pullman, WA (US); Gary A. Wayman, Pullman, WA (US)

(73) Assignee: Washington State University, Pullman, WA (US)

( * ) Notice: Subject to any disclaimer, the term of this patent is extended or adjusted under 35 U.S.C. 154(b) by 17 days.

This patent is subject to a terminal disclaimer.

(21) Appl. No.: 14/038,973

(22) Filed: Sep. 27, 2013

(65) Prior Publication Data

US 2014/0051633 A1   Feb. 20, 2014

Related U.S. Application Data

(63) Continuation-in-part of application No. PCT/US2012/031815, filed on Apr. 2, 2012.

(60) Provisional application No. 61/471,122, filed on Apr. 2, 2011, provisional application No. 61/471,124, filed on Apr. 2, 2011, provisional application No. 61/706,567, filed on Sep. 27, 2012, provisional application No. 61/706,437, filed on Sep. 27, 2012.

(51) Int. Cl.
| | |
|---|---|
| *A61K 38/05* | (2006.01) |
| *C07K 5/065* | (2006.01) |
| *C07K 5/103* | (2006.01) |
| *C07K 5/083* | (2006.01) |
| *C07K 14/475* | (2006.01) |

(52) U.S. Cl.
CPC ............ *C07K 5/06078* (2013.01); *C07K 5/101* (2013.01); *C07K 5/0808* (2013.01); *C07K 14/4753* (2013.01); *A61K 38/05* (2013.01)

(58) Field of Classification Search
CPC . A61K 38/05; C07K 5/06078; C07K 14/4753
See application file for complete search history.

(56) References Cited

PUBLICATIONS

Jackowski, British Journal of Neurosurgery 9:303-317 (1995).*

* cited by examiner

*Primary Examiner* — Robert C Hayes
(74) *Attorney, Agent, or Firm* — Whitham Curtis Christofferson & Cook, PC

(57) ABSTRACT

Small molecule, peptidic hepatocyte growth factors mimics, which act as both mimetics and antagonists, have been generated. These molecules have been shown or predicted to have therapeutic potential for numerous pathologies including dementia (e.g. Alzheimer's) and Parkinson's disease.

1 Claim, 40 Drawing Sheets

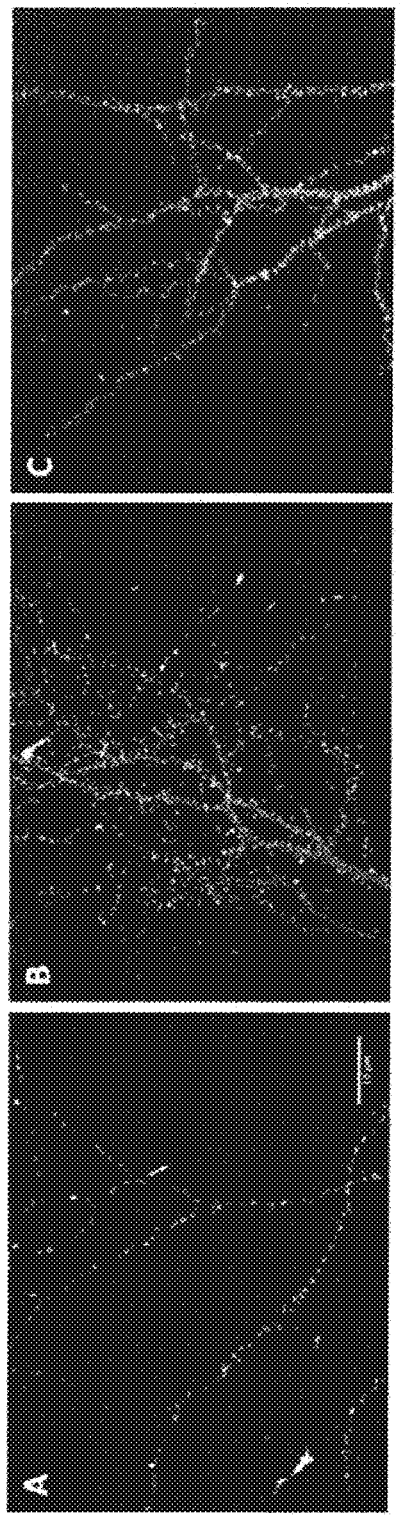
*Figure 3A*     *Figure 3B*     *Figure 3C*
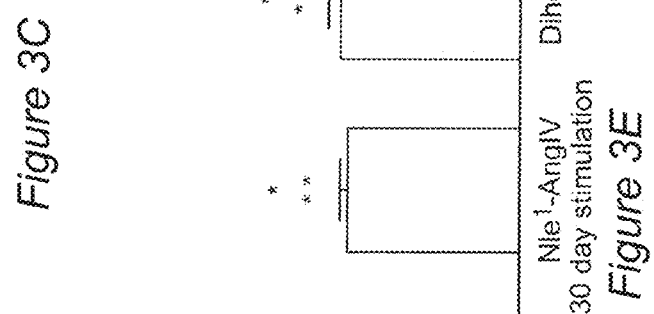
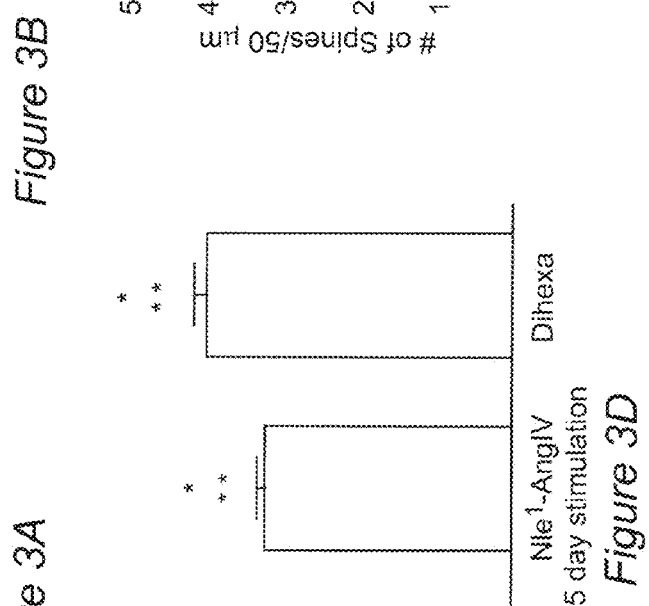
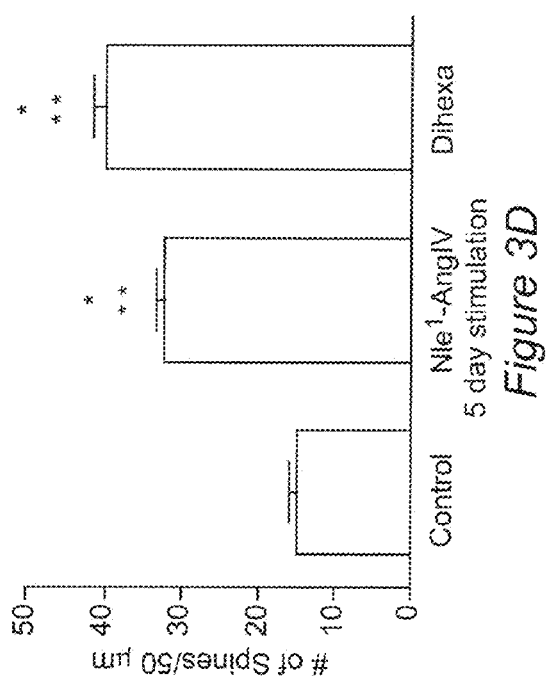
*Figure 3D*
*Figure 3E*

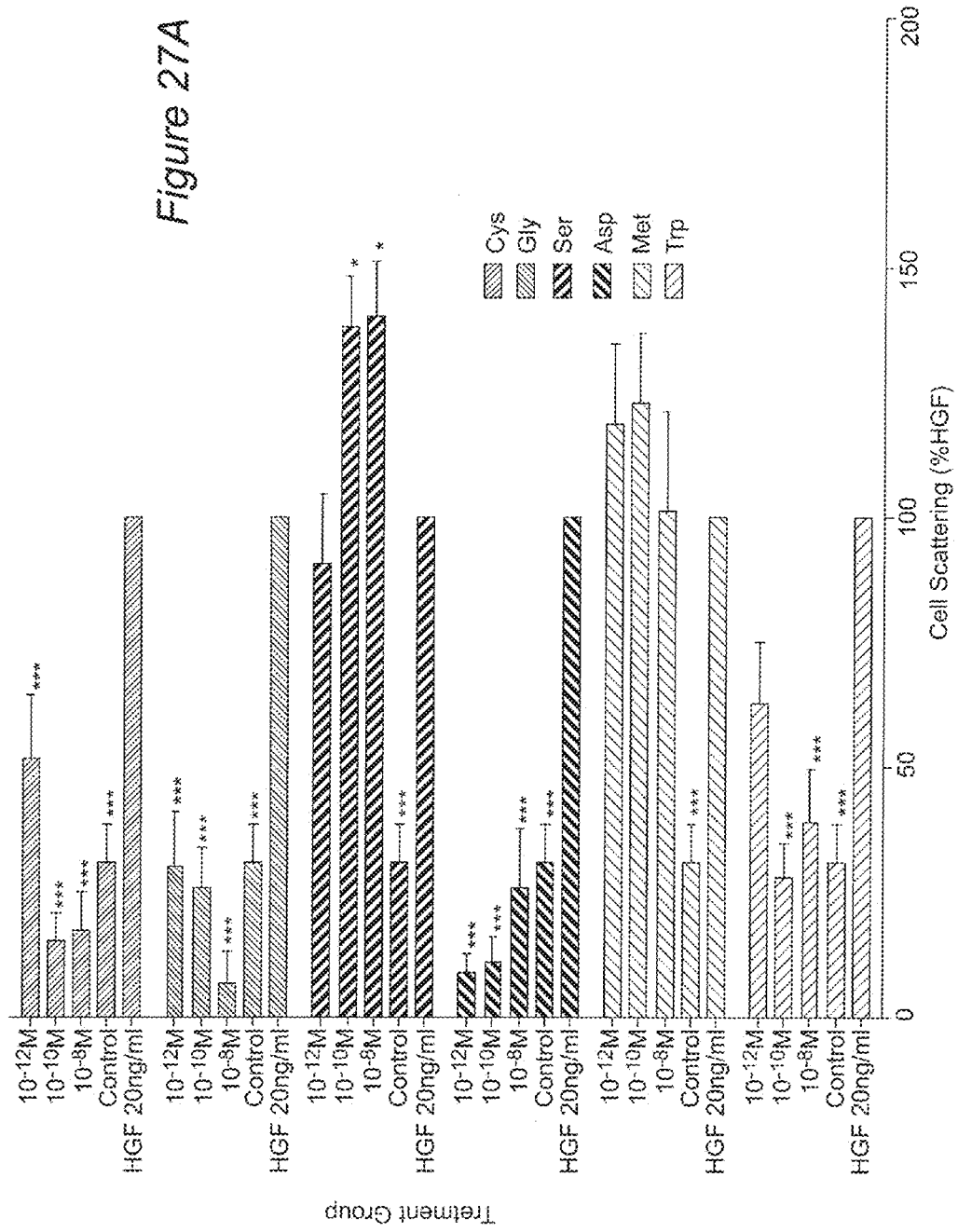

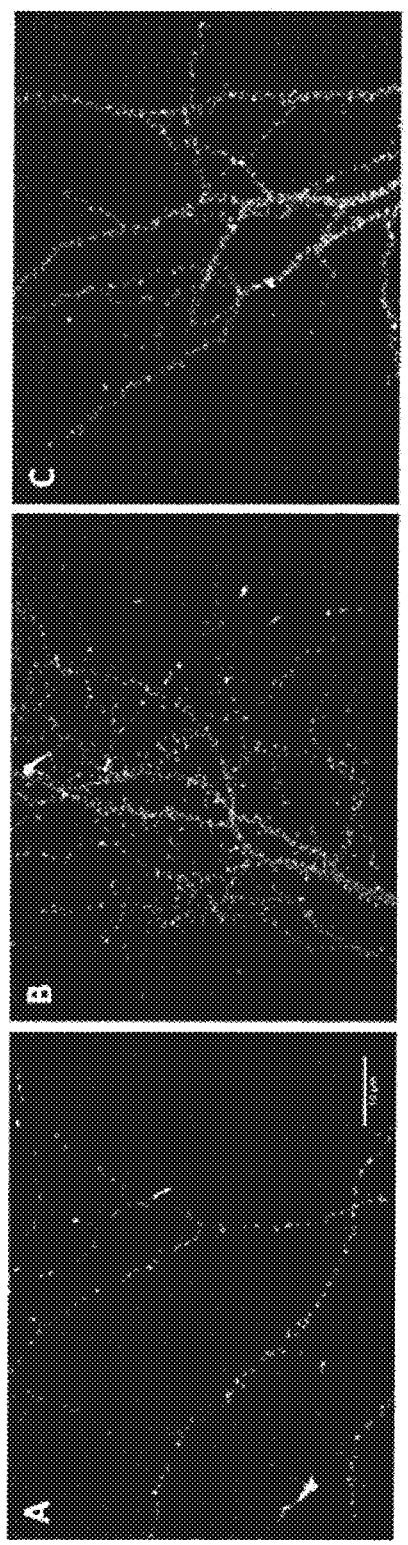
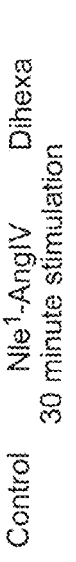
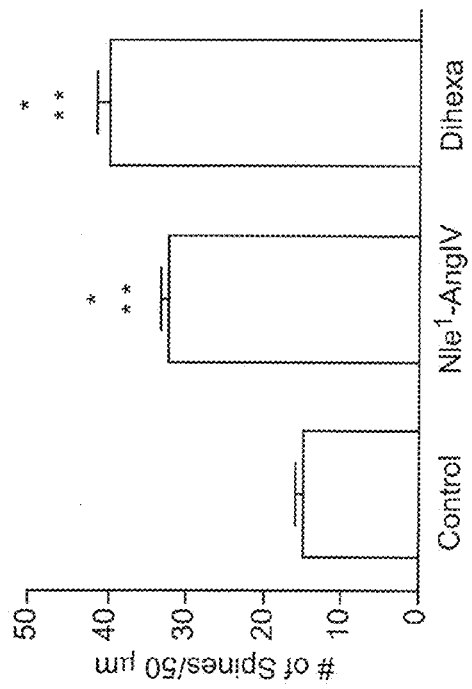
Figure 38A  Figure 38B  Figure 38C
Figure 38D
Figure 38E

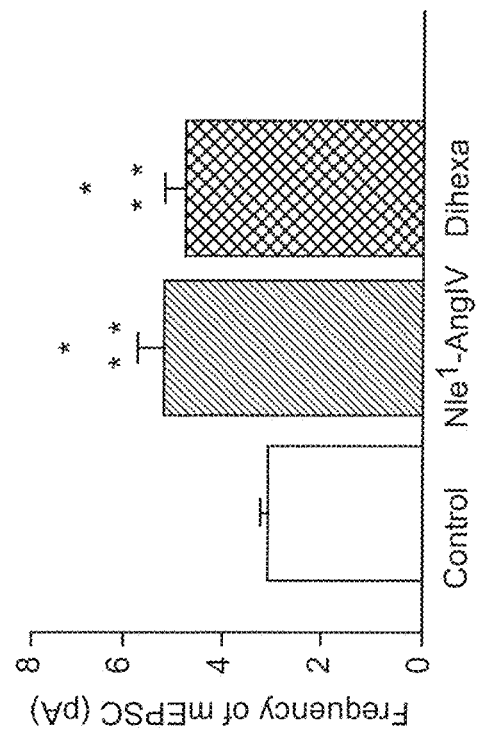
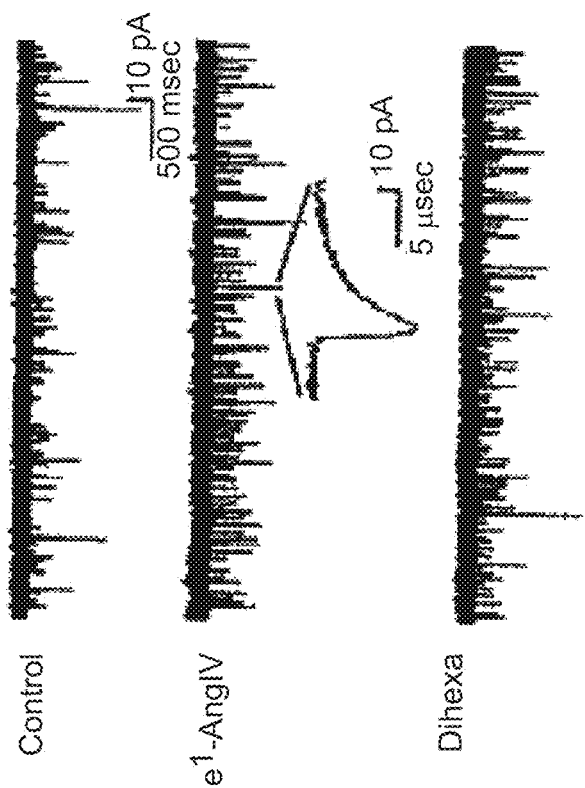
Figure 41A
Figure 41B

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Synthetic angiotensin ligand
<220> FEATURE:
<221> NAME/KEY: MISC_FEATURE
<222> LOCATION: (1)..(1)
<223> OTHER INFORMATION: Norleucine
<220> FEATURE:
<221> NAME/KEY: MISC_FEATURE
<222> LOCATION: (3)..(4)
<223> OTHER INFORMATION: A reduced peptide bond (-CH2-NH2-)

<400> SEQUENCE: 1

Xaa Tyr Leu His Pro Phe
1               5

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 2
gtgtcaggag gtgtttggaa ag                                          22

<210> SEQ ID NO 3
<211> LENGTH: 6
<212> TYPE: PRT
<213> ORGANISM: Artificial Sequence
<220> FEATURE:
<223> OTHER INFORMATION: Synthetic hinge peptide

<400> SEQUENCE: 3

Asp Tyr Ile Arg Asn Cys
1               5
```

HEPATOCYTE GROWTH FACTOR MIMICS AS THERAPEUTIC AGENTS

CROSS-REFERENCE TO RELATED APPLICATIONS

This application is a continuation-in-part of U.S. Pat. No. 8,598,118 filed Feb. 15, 2013 which is a continuation of International Application No. PCT/US2012/031815, filed Apr. 2, 2012, which claims priority to U.S. Application No. 61/471,122, filed Apr. 2, 2011, and U.S. Application No. 61/471,124, filed Apr. 2, 2011, the complete contents of which are herein incorporated by reference.

BACKGROUND OF THE INVENTION

1. Field of the Invention

The invention generally relates to methods of using hepatocyte growth factor (HGF) mimics to treat dementia and Parkinson's disease.

2. Background of the Invention

Dementia

There are approximately 10 million diagnosed dementia patients in the United States alone and that number continues to grow every year as the population ages. The costs of treatment and care of these patients are in excess of $70 billion annually and are increasing rapidly. Unfortunately, the current treatment options for the management of dementia are severely limited and largely ineffective. The lack of treatment options for a burgeoning health problem of this magnitude necessitates that new and innovative therapeutic approaches be developed as quickly as possible.

At its core dementia results from a combination of diminished synaptic connectivity among neurons and neuronal death in the entorhinal cortex, hippocampus and neocortex. Therefore, an effective treatment would be expected to augment synaptic connectivity, protect neurons from underlying death inducers, and stimulate the replacement of lost neurons from preexisting pools of neural stem cells. These clinical endpoints advocate for the therapeutic use of neurotrophic factors, which mediate neural development, neurogenesis, neuroprotection, and synaptogenesis. Neurotrophic factors have been considered as treatment options for many neurodegenerative diseases including Alzheimer's disease.

Parkinson's Disease

A treatment option long considered for Parkinson's disease (PD) has been the application of growth factors with the intention of halting disease progression, restoring lost function, or hopefully both. However, this dream has gone largely unfulfilled at the level of clinical medicine because of limitations related to brain delivery and costs. Growth factors are universally large proteins that are both metabolically labile and too large to pass the blood-brain barrier (BBB). As such, most approaches to delivery have utilized gene therapy methods with the hope that the growth factor will be expressed in the correct location at a high enough concentration and for a long enough period to provide clinical relief. Although a number of creative and successful approaches in animal models have been employed to deliver growth factors (e.g. GDNF) to the brain, these methodologies are technically complex and prohibitively difficult to bring to practice with large numbers of patients.

Unfortunately, the direct use protein neurotrophic factors as therapeutic agents has at least two serious limitations: 1) their large size and hydrophilic character preclude blood-brain barrier permeability (BBB); and 2) the need to manufacture such proteins by recombinant methods at high cost would limit their widespread use.

It would be a boon to have available molecules with growth factor activity which are orally active, display profound growth factor activity, and yet are inexpensive to synthesize, for the treatment of dementia and PD.

SUMMARY

The invention provides small molecule mimetics of the growth factor hepatocyte growth factor (HGF) orally active, display profound growth factor activity, and are inexpensive to synthesize. The mimetics display profound anti-dementia and anti-PD activity, and herein are described methods for treating and/or preventing dementia and PD using the HGF minetics.

It is an object of the invention to provide methods for treating, slowing progression of and/or reversing symptoms of dementia in a subject in need thereof. The methods comprise a step of administering to the subject a therapeutic amount of one or more hepatocyte growth factor (HGF) mimics having the general structural formula

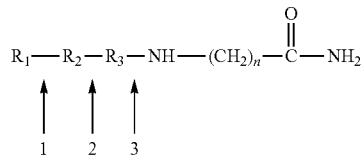

where
$R_1$ is one of an N-acyl group, a substituted or unsubstituted phenyl, a norleucine group, and an amino acid selected from tyrosine, phenylalanine, aspartic acid, arginine, isoleucine, serine, histidine, glycine, cysteine, methionine, tryptophan, lysine norvaline, ornithine, and s-benzyl cysteine;
$R_2$ is an amino acid selected from the group selected from the group consisting of tyrosine, phenylalanine, aspartic acid, arginine, isoleucine, serine, histidine, glycine, cysteine, methionine, tryptophan, lysine and valine;
$R_3$ is an amino acid selected from isoleucine, leucine and valine; and
n ranges from 3-6;
and wherein covalent bonds 1, 2 and 3 are selected from the group consisting of peptide bonds or reduced peptide bonds.

In some aspects, the one or more HGF mimics is hexanoic-tyrosine-isoleucine-(6)-amino-hexanoic amide. In additional aspects, the dementia is Alzheimer's disease dementia.

The invention also provides methods for enhancing cognitive function and/or treating and/or preventing cognitive dysfunction in a subject in need thereof. The methods comprise a step of administering to the subject a therapeutic amount of one or more hepatocyte growth factor (HGF) mimics having the general structural formula

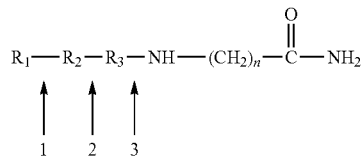

where
$R_1$ is one of an N-acyl group, a substituted or unsubstituted phenyl, a norleucine group, and an amino acid selected from tyrosine, phenylalanine, aspartic acid, arginine, isoleucine, serine, histidine, glycine, cysteine, methionine, tryptophan, lysine norvaline, ornithine, and s-benzyl cysteine;

$R_2$ is an amino acid selected from the group selected from the group consisting of tyrosine, phenylalanine, aspartic acid, arginine, isoleucine, serine, histidine, glycine, cysteine, methionine, tryptophan, lysine and valine;

$R_3$ is an amino acid selected from isoleucine, leucine and valine; and n ranges from 3-6;

and wherein covalent bonds 1, 2 and 3 are selected from the group consisting of peptide bonds or reduced peptide bonds.

In some aspects, the step of administering is performed multiple times over a period of time. In some aspects, the methods further comprise the steps of testing cognition of the subject during the period of time, and adjusting an amount of the one or more HGF mimics administered based on test results. For example, the amount of mimic may be increased if no or an insufficient response to treatment is observed, or decreased if a desired level of improvement is observed, etc. In some aspects, the one or more HGF mimics is hexanoic-tyrosine-isoleucine-(6)-amino-hexanoic amide.

The invention further provides methods for providing neuroprotection and/or inducing neuroregeneration in a subject in need thereof. The methods comprise a step of administering to the subject a therapeutic amount of one or more hepatocyte growth factor (HGF) mimics having the general structural formula

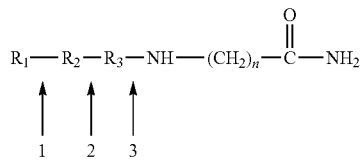

where $R_1$ is one of an N-acyl group, a substituted or unsubstituted phenyl, a norleucine group, and an amino acid selected from tyrosine, phenylalanine, aspartic acid, arginine, isoleucine, serine, histidine, glycine, cysteine, methionine, tryptophan, lysine norvaline, ornithine, and s-benzyl cysteine;

$R_2$ is an amino acid selected from the group selected from the group consisting of tyrosine, phenylalanine, aspartic acid, arginine, isoleucine, serine, histidine, glycine, cysteine, methionine, tryptophan, lysine and valine;

$R_3$ is an amino acid selected from isoleucine, leucine and valine; and n ranges from 3-6;

and wherein covalent bonds 1, 2 and 3 are selected from the group consisting of peptide bonds or reduced peptide bonds.

In some instances, the one or more HGF mimics is hexanoic-tyrosine-isoleucine-(6)-amino-hexanoic amide.

In yet further aspects, the invention provides methods of treating Stage I, Stage II or Stage III dementia in a subject in need thereof. The methods comprise administering to the subject a therapeutic amount of one or more hepatocyte growth factor (HGF) mimics having the general structural formula

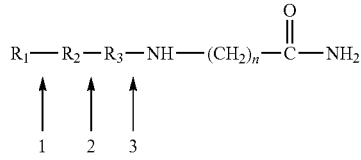

where $R_1$ is one of an N-acyl group, a substituted or unsubstituted phenyl, a norleucine group, and an amino acid selected from tyrosine, phenylalanine, aspartic acid, arginine, isoleucine, serine, histidine, glycine, cysteine, methionine, tryptophan, lysine norvaline, ornithine, and s-benzyl cysteine;

$R_2$ is an amino acid selected from the group selected from the group consisting of tyrosine, phenylalanine, aspartic acid, arginine, isoleucine, serine, histidine, glycine, cysteine, methionine, tryptophan, lysine and valine;

$R_3$ is an amino acid selected from isoleucine, leucine and valine; and n ranges from 3-6;

and wherein covalent bonds 1, 2 and 3 are selected from the group consisting of peptide bonds or reduced peptide bonds.

In some cases, the one or more HGF mimics is hexanoic-tyrosine-isoleucine-(6)-amino-hexanoic amide.

BRIEF DESCRIPTION OF THE DRAWINGS

FIG. 3A-E. Time dependent effects of $Nle^1$-AngIV and Dihexa treated neurons on spinogenesis. Hippocampal neurons transfected with mRFP-β-actin were treated with $10^{-12}$ M Dihexa or $Nle^1$-Ang IV for 5 days in culture or for 30 minutes prior to fixation on day in vitro 12 (DIV 12), promote spinogenesis. A) Representative image of the dendritic arbor of a 5 day vehicle treated hippocampal neuron. B) Representative image of a dendritic arbor from a neuron stimulated for 5 days with $10^{-12}$ M Dihexa. C) Representative image of the dendritic arbor of a neuron stimulated with $10^{-12}$ M $Nle^1$-Ang IV for 5 days. D) Bar graph representing the number of spines per 50 μm dendrite length per treatment condition following a 5 day in vitro treatment. * P<0.001; n=200. E) Bar graph representing the number of spines per 50 μm dendrite length per treatment condition following an acute 30 minute treatment. * P<0.001; n=60. *Data obtained from separate cultures; cultures were 12 days old at time of fixing. Mean±S.E.M. by one-way ANOVA and Tukey post hoc test.

FIG. 38A-E. Nle$^1$-AngIV and Dihexa increase the number of dendritic spines. Time dependent effects of Nle$^1$-AngIV and Dihexa treated neurons on spinogenesis. Hippocampal neurons transfected with mRFP-β-actin were treated with $10^{-12}$ M dihexa or $10^{-12}$ M Nle$^1$-Ang IV for 5 days or 30 minutes in culture prior to fixation on day in vitro 12 (DIV12). A) Representative image of the dendritic arbor of a 5 day vehicle treated hippocampal neuron. B) Representative image of a dendritic arbor from a neuron stimulated for 5 days with $10^{-12}$ M dihexa. C) Representative image of the dendritic arbor of a neuron stimulated with $10^{-12}$ M Nle$^1$-Ang IV for 5 days. D) Bar graph representing the number of spines per 50 μm dendrite length per treatment condition following a 5 day in vitro treatment. *p<0.001; n=200 dendritic segments. E) Bar graph representing the number of spines per 50 μm dendrite length per treatment condition following an acute 30 minute treatment. *p<0.001; n=60 dendritic segments. Mean±S.E.M. Analysis by one-way ANOVA and Tukey post hoc test.

FIGS. 41A and B. Increased frequencies of mini-excitatory postsynaptic currents (mEPSCs) in dissociated hippocampal neurons treated with Nle$^1$-AngIV and Dihexa. Recordings were carried out on rat dissociated hippocampal neurons treated with vehicle, $10^{-12}$ M Nle$^1$-AngIV or $10^{-12}$ M dihexa for 5 days prior to recording. The post-synaptic currents, which were recorded in the presence of strychnine, picrotoxin and tetrodotoxin, represented spontaneous bursts likely mediated by AMPA receptors. A) Representative traces of mEPSC recordings from Nle$^1$-AngIV or dihexa treated hippocampal neurons. B) Bar graph illustrating the increase in mEPSC frequencies in hippocampal neurons that resulted from Nle$^1$-AngIV or Dihexa treatment. The increased frequencies indicate that dendritic spines induced by Nle$^1$-AngIV or dihexa support functional synaptic transmission. *** p<0.001; Mean±S.E.M.; n=25.

DETAILED DESCRIPTION

Figure 1A:
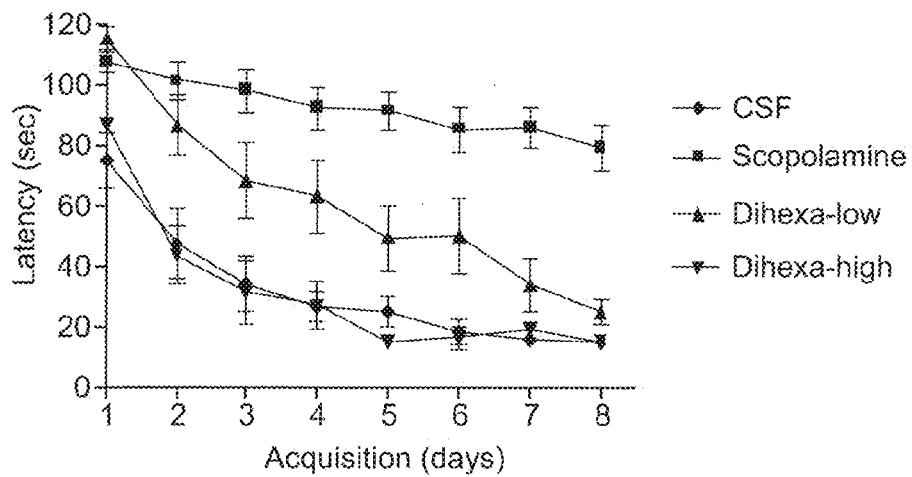
FIGS. 1A, B, and C. Effect of Dihexa on spatial learning in the water maze. A: 30 minutes before beginning testing rats were given scopolamine directly into the brain intracerebroventricularly (ICV) and 10 minutes later Dihexa was given ICV at 10 pmoles (low dose) or 100 pmoles (high dose). This was done daily before the first training trial. There were 5 trials per day for 8 days. The latency to find the pedestal was considered a measure of learning and memory. Rats receiving high Dihexa were able to completely overcome the scopolamine deficits and were no different than controls. B. 30 minutes before beginning testing rats were given scopolamine directly into the brain intracerebroventricularly (ICV) and 10 minutes later Dihexa was given orally 1.25 mg/kg/day (low dose) and 2 mg/kg/day (high dose). This was done daily before the first training trial. There were 5 trials per day for 8 days. The latency to find the pedestal was considered a measure of learning and memory. Rats receiving high dose Dihexa were able to completely overcome the scopolamine deficits and were no different than controls. C: Aged rats of mixed sex and age (22-26 months) were randomly assigned to a control/untreated group or a Dihexa treated group (2 mg/kg/day). Rats were not prescreened. Note that normally~50% of aged rats show deficits, thus the large group errors. The Dihexa group performed significantly better than untreated controls.

Peptide analogs or mimics of HGF (also referred to as "growth factor mimics" or "analogs" or "mimetics") having a variety of therapeutic utilities have the following general structural formula:

$$R_1 - R_2 - R_3 - NH - (CH_2)_n - \overset{O}{\underset{\|}{C}} - NH_2$$
$$\uparrow \quad \uparrow \quad \uparrow$$
$$1 \quad 2 \quad 3$$

where $R_1$ is an N-acyl group such as, for example, hexanoyl, heptanoyl, pentanoyl, butanoyl, propanoyl, acetanoyl, or benzoyl,
 a substituted or unsubstituted phenyl,
 a D or L norleucine,
 an amino acid (D or L) such as, for example, lysine, arginine, norvaline, ornithine, or S-benzyl cysteine amino acid residues;

$R_2$ is an amino acid (D or L), such as, for example, tyrosine, cysteine, phenyalanine, aspartic acid, glutamic acid, glycine, tryptophan, lysine, homocysteine, homoserine, homophenylalanine;

$R_3$ is a D or L isoleucine, leucine or valine amino acid residue; and n ranges from 3-6;

and wherein covalent bonds 1, 2 and 3 are either peptide bonds (e.g. —CO—NH— or reduced peptide bonds (CH$_2$—NH$_2$).

An exemplary peptide bond and reduced peptide bond are depicted below:

Peptide bond    Reduced peptide bond

Compounds within the general structural formula have been synthesized and analyzed according to the following procedures.

Standard Synthesis Method:

All compounds were synthesized by solid phase methods using an AAPPTEC Endeavor 90 peptide synthesizer using Fmoc protected amino acids. All peptide amides were synthesized on a Rink resin. The resin was pre-swollen in dimethylformamide (DMF) and deprotected with 20% piperidine/DMF for 30 minutes. The piperidine/DMF was then removed by filtration. After deprotection, the N-α. Fmoc protected amino acid was added to reaction vessel as a dry powder (3 equivalents). The vessel was then filled with ⅔ full with DMF and dry diisopropylethylamine (DIPEA; 3.5-4 equivalents) was added. Next N-[(1H-benzotriazol-1-yl) (dimethylamino)methylene]-N-methyl-methanaminium hexafluorophosphate N-oxide (HBTU; 2.9 equivalents) was added and the suspension mixed for 30 minutes. The solution was then removed by filtration. The resin was then washed twice with DMF, twice with methanol, twice with dichloromethane, and finally twice more with DMF. Solutions were removed by filtration after each wash. Coupling efficiency was monitored using a Kaiser test for free amines. If the test was positive the amino acid was re-coupled to the resin or growing peptide chain. If the test indicated a good linkage, the resin was washed once more with DMF, deprotected with 20% piperidine/DMF for 30 minutes as indicated above, and again washed with DMF. The coupling then proceeded as indicated above.

Acylation of the N-Terminal of the Peptide:

After final deprotection, the peptide resin is incubated with 20% of the appropriate acyl anhydride in DMF and DIPEA (1.5 equivalents) for 30 minutes at room temperature. The resin was now washed twice with DMF, twice with methanol, twice with dichloromethane, and finally twice more with DMF. The solution was removed by filtration and a Kaiser test was performed to verify the completeness of the capping. If free amine was detected the capping procedure was repeated.

Insertion of an N-Terminal Reduced Peptide Bond:

After deprotection, hexanal (3 equivalents) DMF was added to the resin and allowed to mix for 5 minutes. Next, 3 equivalents of sodium cyanoborohydride were added and the suspension was mixed for an additional 2 hours. After the standard washing procedure was performed (see above), the Kaiser test was again used to verify the completeness of the reaction. If coupling was deemed incomplete, the procedure was repeated.

Cleavage of Peptide from Rink Resin:

After the last amino acid was deprotected and washed the resin was transferred to a sintered glass funnel (4 porosity) and the DMF removed by vacuum. The semi-dry resin was then suspended in 20% trifluoroacetic acid (TFA) with 2.5% triisopropyl-silane as a scavenger, incubated at room temperature for 15 minutes, and filtered. The resin was washed three times with additional DMF and filtered. Ten volumes of ice-cold diethyl ether were added to the combined filtrates and the mixture allowed to set at 4° C. overnight. Precipitated peptide was recovered by filtration and washed three times with ice-cold ether. For very hydrophobic peptides the combined ether washes were re-extracted with DMF, allowed to precipitate peptide, and filtered to recover additional peptide.

Peptide Purification and Analysis:

Crude peptides were first purified by reverse phase HPLC using a C18 column using gradient elution. The typical gradient was 10% to 40% component B over 30 minutes at a flow rate of 1 ml/min at 37° C. where component A was 80 mM triethyamine phosphate, pH 3.0 and component B was acetonitrile (ACN). In all instances only a single peak with 215 nm absorption was detected and collected. The collected compound was lyophilized and redissolved in 20% methanol and injected onto a second C18 column. The HPLC/MS system used was from Shimadzu (Kyoto, Japan), consisting of a CBM-20A communications bus module, LC-20AD pumps, SIL-20AC auto sampler, SPD-M20A diode array detector and LCMS-2010EV mass spectrometer. Data collection and integration were achieved using Shimadzu LCMS solution software. The analytical column used was an Econosphere C18 (100 mm×2.1 mm) from Grace Davison Discovery Science (Deerfield, Ill., USA). The mobile phase consisted of HPLC grade methanol and water with 0.1% trifluoroacetic acid. Separation was carried out using a non-isocratic method (20%-50% methanol over 30 min) at 37° C. and a flow rate of 0.3 mL/min. For MS analysis, a positive ion mode (Scan) was used and peaks analyzed at the anticipated m/z. Typical peak purity analysis revealed a peak purity index of >0.95. Wavelength ratioing with the diode array detector further confirmed peak purity.

Table 1 below presents a listing of compounds in Family 1, drawn to mimetics, and Famillies 2-5, drawn to antagonists, all of which have been synthesized and analyzed according to the procedures described above.

TABLE 1

General Structure of Family 1 (Mimetics) and Families 2-5 (Antagonists)

$$R_1—R_2—R_3—NH—(CH_2)_n—\overset{O}{\underset{\|}{C}}—NH_2$$

↑ ↑ ↑
1 2 3

| Family # | R₁ (N-acyl group) | R2 | R3 | 1 |
|---|---|---|---|---|
| 1 | hexanoyl | Tyr | Ile | pb |
|   | heptanoyl | Tyr | Ile | pb |
|   | pentanoyl | Tyr | Ile | pb |
|   | butanoyl | Tyr | Ile | pb |
|   | propanoyl | Tyr | Ile | pb |
|   | acetanoyl | Tyr | Ile | pb |
|   | benzoyl | Tyr | Ile | pb |
|   | hexanoyl | Tyr | Ile | ψ |

| Family # | R1 | R2 | R3 |
|---|---|---|---|
| 2 | D-Nle | Tyr | Ile |
|   | D-Nle | Phe | Ile |
|   | D-Nle | Asp | Ile |
|   | D-Nle | Arg | Ile |
|   | D-Nle | Ile | Ile |
|   | D-Nle | Ser | Ile |
|   | D-Nle | His | Ile |
|   | D-Nle | Gly | Ile |
|   | D-Nle | Cys | Ile |
|   | D-Nle | Met | Ile |
|   | D-Nle | Trp | Ile |
|   | D-Nle | Lys | Ile |
|   | D-Nle | Val | Ile |
|   | D-Nle | Gly | D-Ile |
| 3 | D-Nle | D-Tyr | Ile |
|   | D-Nle | D-Phe | Ile |
|   | D-Nle | D-Asp | Ile |
|   | D-Nle | D-Arg | Ile |
|   | D-Nle | D-Ile | Ile |
|   | D-Nle | D-Ser | Ile |
|   | D-Nle | D-His | Ile |
|   | D-Nle | D-Gly | Ile |
|   | D-Nle | D-Cys | Ile |
|   | D-Nle | D-Met | Ile |
|   | D-Nle | D-Trp | Ile |
|   | D-Nle | D-Lys | Ile |
| 4 | Tyr | Tyr | Ile |
|   | Phe | Tyr | Ile |
|   | Asp | Tyr | Ile |
|   | Arg | Tyr | Ile |
|   | Ile | Tyr | Ile |
|   | Ser | Tyr | Ile |
|   | His | Tyr | Ile |
|   | Gly | Tyr | Ile |
|   | Cys | Tyr | Ile |
|   | Met | Tyr | Ile |
|   | Typ | Tyr | Ile |
|   | Lys | Tyr | Ile |
| 5 | D-Tyr | Tyr | Ile |
|   | D-Phe | Tyr | Ile |
|   | D-Asp | Tyr | Ile |
|   | D-Arg | Tyr | Ile |
|   | D-Ile | Tyr | Ile |
|   | D-Ser | Tyr | Ile |
|   | D-His | Tyr | Ile |
|   | D-Cys | Tyr | Ile |
|   | D-Met | Tyr | Ile |
|   | D-Typ | Tyr | Ile |
|   | D-Lys | Tyr | Ile |

Arrows 1-3 denote
pb = peptide bond;
ψ = reduced peptide bond ($CH_2$—$NH_2$)
n = 5

With reference to Table 1, while a number of compounds which have been synthesized include tyrosine and isoleucine at $R_2$ and $R_3$, respectively, a wide range of amino acid and other residues might be used for the mimetics or agonists (Family 1 and Families 2-5, respectively) in the practice of embodiments of the invention at these other positions including, without limitation, tyrosine, cysteine, methionine, phenylalaine, aspartic acid, glutamic acid, histidine, tryptophan, lysine, leucine, valine, homocysteine, homoserine, and homophenylalanine. Further, while the mimetics include certain N-acyl groups as specified in Table 1 (Family 1), in the practice of various embodiments of the invention other N-acyl groups or substituted or unsubstituted phenyl groups may be used at $R_1$. In addition, while a number of the agonists in Table 1 (Families 2-5) have norleucine at $R_1$, or an amino acid residue, in the practice of various embodiments of this invention a number of an amino acid residues (D or L) may be used at residue $R_1$, including without limitation, tyrosine, phenylalanine, aspartic acid, arginine, isoleucine, serine, histidine, glycine, cysteine, methionine, tryptophan, norvaline, ornithine, S-benzyl cysteine amino acid residues. Finally, while all the compounds synthesized and tested in Table 1 included 5 methyl repeats, the methyl repeats (n) could range from 3-6 within the practice of the some of the embodiments of the present invention.

Compounds within Table 1 have also been assessed as follows:

Assessment of HGF Mimetic Activity:

HGF mimetic activity was typically assessed by one or both of two methods: augmentation of HGF-dependent c-Met phosphorylation in HEK293 cells, or 2) augmentation of HGF-dependent cell scattering in MDCK cells. All the compounds in Family one were tested using the c-Met phosphorylation assay. N-hexanoyl-Tyr-Ile-(6) aminohexamide was further evaluated and found to have spectacularly augment HGF-dependent MDCK cell scattering. Table 2 presents a summary of the results.

TABLE 2

| Compound ($10^{-12}$M) | HGF Mimetic Activity |
| --- | --- |
| N-heptanoyl-Tyr-Ile-(6) aminohexamide | ++++ |
| N-hexanoyl-Tyr-Ile-(6) aminohexamide | ++++ |
| N-pentaanoyl-Tyr-Ile-(6) aminohexamide | ++++ |
| N-butanoyl-Tyr-Ile-(6) aminohexamide | +++ |
| N-propananoyl-Tyr-Ile-(6) aminohexamide | ++ |
| N-acetanoyl-Tyr-Ile-(6) aminohexamide | + |
| N-benzoyl-Tyr-Ile-(6) aminohexamide | + |
| N-hexanoyl-ψ (CH$_2$—NH$_2$)-Tyr-Ile-(6) aminohexamide | +++ |

Cell Culture.

Human embryonic kidney cells 293 (HEK293), Madin Darby canine kidney cells (MDCK), and B16F10 murine melanoma cells were grown in DMEM, 10% fetal bovine serum (FBS). Cells were grown to 90-100% confluency before use. For most but not all studies HEK and MDCK cells were serum starved for 24 hours prior to the initiation of drug treatment.

Western Blotting.

HEK293 cells were seeded in 6 well tissue culture plates and grown to 95% confluency in DMEM containing 10% FBS. The cells were serum deprived for 24 hours prior to the treatment to reduce the basal levels of phospho-Met. Following serum starvation, cocktails comprised of vehicle and HGF (2.5 ng/ml) with/without the test compound were prepared and pre-incubated for 30 minutes at room temperature. The cocktail was then added to the cells for 10 minutes to stimulate the Met receptor and downstream proteins. Cells were harvested using RIPA lysis buffer (Upstate) fortified with phosphatase inhibitor cocktails 1 and 2 (Sigma-Aldrich; St. Louis, Mo.). The lysate was clarified by centrifugation at 15,000 g for 15 minutes, protein concentrations were determined using the BCA total protein assay, and then appropriate volumes of the lysates were diluted with 2× reducing Laemmli buffer and heated for ten minutes at 95° C. Samples containing identical amounts of protein were resolved using SDS-PAGE (Criterion, BioRad Laboratories), transferred to nitrocellulose, and blocked in Tris-buffered saline (TBS) containing 5% milk for one hour at room temperature. The phospho-Met antibody was added to the blocking buffer at a final concentration of 1:1000 and incubated at 4° C. overnight with gentle agitation. The membranes were then washed several times with water and TBS (PBS, 0.05% Tween-20), a 1:5000 dilution of horseradish-peroxidase conjugated goat anti-rabbit antiserum was added, and the membranes further incubated for one hour at room temperature. Proteins were visualized using the Supersignal West Pico Chemiluminescent Substrate system (Pierce, Fenton, Mo.) and molecular weights determined by comparison to protein ladders (BenchMark, Invitrogen; and Kaleidoscope, BioRad). Images were digitized and analyzed using a UVP phospho-imager.

Scattering Assay.

MDCK cells were grown to 100% confluency on the coverslips in six-well plates and washed twice with PBS. The confluent coverslips were then aseptically transferred to new six well plates containing 900 µl serum free DMEM. Norleual, Hinge peptide, and/or HGF (2.5 ng/ml) were added to appropriate wells. Control wells received PBS vehicle. Plates were incubated at 37° C. with 5% CO$_2$ for 48 hours. Media was removed and cells were fixed with methanol. Cells were stained with Diff-Quik Wright-Giemsa (Dade-Behring, Newark, Del.) and digital images were taken. Coverslips were removed with forceps and more digital images were captured. Pixel quantification of images was achieved using Image J and statistics were performed using Prism 5 and InStat v.3.05.

For the general structural formula presented above, and reproduced below for ease of reference, there are several different compounds which can be prepared according to the synthesis procedures described above and used for therapies described below. Table 3 identifies various exemplary families with various listed compounds in those families (identified by substitution of moieties within the general formula).

TABLE 3

General Structure:

$$R_1 - R_2 - R_3 - NH - (CH_2)_n - \overset{O}{\underset{\|}{C}} - NH_2$$

↑     ↑     ↑
        1     2     3

| Family # | R$_1$ | R2 | R3 | n | 1 | 2 | 3 |
| --- | --- | --- | --- | --- | --- | --- | --- |
| 1 | hexanoyl | Y | I | 5 | pb | pb | pb |
|   | heptanoyl | Y | I | 5 | pb | pb | pb |
|   | pentanoyl | Y | I | 5 | pb | pb | pb |
|   | butanoyl | Y | I | 5 | pb | pb | pb |
|   | propanoyl | Y | I | 5 | pb | pb | pb |
|   | acetanoyl | Y | I | 5 | pb | pb | pb |
|   | isopropanoyl | Y | I | 5 | pb | pb | pb |
|   | tert-butanoyl | Y | I | 5 | pb | pb | pb |
|   | isobutanoyl | Y | I | 5 | pb | pb | pb |
|   | benzoyl | Y | I | 5 | pb | pb | pb |
| 2 | hexanoyl | Y | I | 5 | ψ | pb | pb |
|   | heptanoyl | Y | I | 5 | ψ | pb | pb |
|   | pentanoyl | Y | I | 5 | ψ | pb | pb |
|   | butanoyl | Y | I | 5 | ψ | pb | pb |
|   | propanoyl | Y | I | 5 | ψ | pb | pb |
|   | acetanoyl | Y | I | 5 | ψ | pb | pb |
|   | isopropanoyl | Y | I | 5 | ψ | pb | pb |
|   | tert-butanoyl | Y | I | 5 | ψ | pb | pb |
|   | isobutanoyl | Y | I | 5 | ψ | pb | pb |
|   | benzoyl | Y | I | 5 | ψ | pb | pb |
| 3 | hexanoyl | Y | I | 5 | ψ | pb | ψ |
|   | heptanoyl | Y | I | 5 | ψ | pb | ψ |
|   | pentanoyl | Y | I | 5 | ψ | pb | ψ |
|   | butanoyl | Y | I | 5 | ψ | pb | ψ |
|   | propanoyl | Y | I | 5 | ψ | pb | ψ |
|   | acetanoyl | Y | I | 5 | ψ | pb | ψ |
|   | isopropanoyl | Y | I | 5 | ψ | pb | ψ |
|   | tert-butanoyl | Y | I | 5 | ψ | pb | ψ |
|   | isobutanoyl | Y | I | 5 | ψ | pb | ψ |
|   | benzoyl | Y | I | 5 | ψ | pb | ψ |
| 4 | hexanoyl | Y | I | 5 | pb | pb | ψ |
|   | heptanoyl | Y | I | 5 | pb | pb | ψ |
|   | pentanoyl | Y | I | 5 | pb | pb | ψ |
|   | butanoyl | Y | I | 5 | pb | pb | ψ |
|   | propanoyl | Y | I | 5 | pb | pb | ψ |
|   | acetanoyl | Y | I | 5 | pb | pb | ψ |
|   | isopropanoyl | Y | I | 5 | pb | pb | ψ |
|   | tert-butanoyl | Y | I | 5 | pb | pb | ψ |
|   | isobutanoyl | Y | I | 5 | pb | pb | ψ |
|   | benzoyl | Y | I | 5 | pb | pb | ψ |
| 5 | hexanoyl | F | I | 5 | pb | pb | pb |
|   | heptanoyl | F | I | 5 | pb | pb | pb |
|   | pentanoyl | F | I | 5 | pb | pb | pb |
|   | butanoyl | F | I | 5 | pb | pb | pb |
|   | propanoyl | F | I | 5 | pb | pb | pb |
|   | acetanoyl | F | I | 5 | pb | pb | pb |
|   | isopropanoyl | F | I | 5 | pb | pb | pb |
|   | tert-butanoyl | F | I | 5 | pb | pb | pb |
|   | isobutanoyl | F | I | 5 | pb | pb | pb |
|   | benzoyl | F | I | 5 | pb | pb | pb |

TABLE 3-continued

General Structure:

$$R_1—R_2—R_3—NH—(CH_2)_n—\overset{\overset{O}{\|}}{C}—NH_2$$

Arrows 1, 2, 3 point to the three bonds (R1-R2, R2-R3, R3-NH).

| Family # | R₁ | R2 | R3 | n | 1 | 2 | 3 |
|---|---|---|---|---|---|---|---|
| 6 | hexanoyl | F | I | 5 | ψ | pb | pb |
|  | heptanoyl | F | I | 5 | ψ | pb | pb |
|  | pentanoyl | F | I | 5 | ψ | pb | pb |
|  | butanoyl | F | I | 5 | ψ | pb | pb |
|  | propanoyl | F | I | 5 | ψ | pb | pb |
|  | acetanoyl | F | I | 5 | ψ | pb | pb |
|  | isopropanoyl | F | I | 5 | ψ | pb | pb |
|  | tert-butanoyl | F | I | 5 | ψ | pb | pb |
|  | isobutanoyl | F | I | 5 | ψ | pb | pb |
|  | benzoyl | F | I | 5 | ψ | pb | pb |
| 7 | hexanoyl | F | I | 5 | ψ | pb | ψ |
|  | heptanoyl | F | I | 5 | ψ | pb | ψ |
|  | pentanoyl | F | I | 5 | ψ | pb | ψ |
|  | butanoyl | F | I | 5 | ψ | pb | ψ |
|  | propanoyl | F | I | 5 | ψ | pb | ψ |
|  | acetanoyl | F | I | 5 | ψ | pb | ψ |
|  | isopropanoyl | F | I | 5 | ψ | pb | ψ |
|  | tert-butanoyl | F | I | 5 | ψ | pb | ψ |
|  | isobutanoyl | F | I | 5 | ψ | pb | ψ |
|  | benzoyl | F | I | 5 | ψ | pb | ψ |
| 8 | hexanoyl | F | I | 5 | pb | pb | ψ |
|  | heptanoyl | F | I | 5 | pb | pb | ψ |
|  | pentanoyl | F | I | 5 | pb | pb | ψ |
|  | butanoyl | F | I | 5 | pb | pb | ψ |
|  | propanoyl | F | I | 5 | pb | pb | ψ |
|  | acetanoyl | F | I | 5 | pb | pb | ψ |
|  | isopropanoyl | F | I | 5 | pb | pb | ψ |
|  | tert-butanoyl | F | I | 5 | pb | pb | ψ |
|  | isobutanoyl | F | I | 5 | pb | pb | ψ |
|  | benzoyl | F | I | 5 | pb | pb | ψ |
| 9 | hexanoyl | C | I | 5 | pb | pb | pb |
|  | heptanoyl | C | I | 5 | pb | pb | pb |
|  | pentanoyl | C | I | 5 | pb | pb | pb |
|  | butanoyl | C | I | 5 | pb | pb | pb |
|  | propanoyl | C | I | 5 | pb | pb | pb |
|  | acetanoyl | C | I | 5 | pb | pb | pb |
|  | isopropanoyl | C | I | 5 | pb | pb | pb |
|  | tert-butanoyl | C | I | 5 | pb | pb | pb |
|  | isobutanoyl | C | I | 5 | pb | pb | pb |
|  | benzoyl | C | I | 5 | pb | pb | pb |
| 10 | hexanoyl | C | I | 5 | ψ | pb | pb |
|  | heptanoyl | C | I | 5 | ψ | pb | pb |
|  | pentanoyl | C | I | 5 | ψ | pb | pb |
|  | butanoyl | C | I | 5 | ψ | pb | pb |
|  | propanoyl | C | I | 5 | ψ | pb | pb |
|  | acetanoyl | C | I | 5 | ψ | pb | pb |
|  | isopropanoyl | C | I | 5 | ψ | pb | pb |
|  | tert-butanoyl | C | I | 5 | ψ | pb | pb |
|  | isobutanoyl | C | I | 5 | ψ | pb | pb |
|  | benzoyl | C | I | 5 | ψ | pb | pb |
| 11 | hexanoyl | C | I | 5 | ψ | pb | ψ |
|  | heptanoyl | C | I | 5 | ψ | pb | ψ |
|  | pentanoyl | C | I | 5 | ψ | pb | ψ |
|  | butanoyl | C | I | 5 | ψ | pb | ψ |
|  | propanoyl | C | I | 5 | ψ | pb | ψ |
|  | acetanoyl | C | I | 5 | ψ | pb | ψ |
|  | isopropanoyl | C | I | 5 | ψ | pb | ψ |
|  | tert-butanoyl | C | I | 5 | ψ | pb | ψ |
|  | isobutanoyl | C | I | 5 | ψ | pb | ψ |
|  | benzoyl | C | I | 5 | ψ | pb | ψ |
| 12 | hexanoyl | C | I | 5 | pb | pb | ψ |
|  | heptanoyl | C | I | 5 | pb | pb | ψ |
|  | pentanoyl | C | I | 5 | pb | pb | ψ |
|  | butanoyl | C | I | 5 | pb | pb | ψ |
|  | propanoyl | C | I | 5 | pb | pb | ψ |
|  | acetanoyl | C | I | 5 | pb | pb | ψ |
|  | isopropanoyl | C | I | 5 | pb | pb | ψ |
|  | tert-butanoyl | C | I | 5 | pb | pb | ψ |
|  | isobutanoyl | C | I | 5 | pb | pb | ψ |
|  | benzoyl | C | I | 5 | pb | pb | ψ |
| 13-16 | Same pattern as families 1-4 with R2 = S | | | | | | |
| 17-20 | Same pattern as families 1-4 with R2 = T | | | | | | |
| 21-24 | Same pattern as families 1-4 with R2 = D | | | | | | |
| 25-28 | Same pattern as families 1-4 with R2 = E | | | | | | |
| 29-32 | Same pattern as families 1-4 with R2 = Y, R3 = V | | | | | | |
| 33-36 | Same pattern as families 1-4 with R2 = F, R3 = V | | | | | | |
| 37-40 | Same pattern as families 1-4 with R2 = C, R3 = V | | | | | | |
| 41-44 | Same pattern as families 1-4 with R2 = S, R3 = V | | | | | | |
| 45-48 | Same pattern as families 1-4 with R2 = T, R3 = V | | | | | | |
| 49-52 | Same pattern as families 1-4 with R2 = D, R3 = V | | | | | | |
| 53-56 | Same pattern as families 1-4 with R2 = E, R3 = V | | | | | | |
| 57-85 | Same pattern as families 29-56 with R3 = L | | | | | | |
| 86-170 | Same pattern as families 1-85 with n = 3 | | | | | | |
| 171-256 | Same pattern as families 1-85 with n = 4 | | | | | | |
| 257-341 | Same pattern as families 1-85 with n = 6 | | | | | | |
| 342 | D-norleucine | Y | I | 5 | pb | pb | pb |
|  | D-norleucine | F | I | 5 | pb | pb | pb |
|  | D-norleucine | C | I | 5 | pb | pb | pb |
|  | D-norleucine | S | I | 5 | pb | pb | pb |
|  | D-norleucine | T | I | 5 | pb | pb | pb |
|  | D-norleucine | D | I | 5 | pb | pb | pb |
|  | D-norleucine | E | I | 5 | pb | pb | pb |
|  | D-norleucine | G | I | 5 | pb | pb | pb |
| 343 | D-norleucine | Y | I | 5 | pb | pb | ψ |
|  | D-norleucine | F | I | 5 | pb | pb | ψ |
|  | D-norleucine | C | I | 5 | pb | pb | ψ |
|  | D-norleucine | S | I | 5 | pb | pb | ψ |
|  | D-norleucine | T | I | 5 | pb | pb | ψ |
|  | D-norleucine | D | I | 5 | pb | pb | ψ |
|  | D-norleucine | E | I | 5 | pb | pb | ψ |
|  | D-norleucine | G | I | 5 | pb | pb | ψ |
| 344 | D-norleucine | Y | I | 5 | ψ | pb | pb |
|  | D-norleucine | F | I | 5 | ψ | pb | pb |
|  | D-norleucine | C | I | 5 | ψ | pb | pb |
|  | D-norleucine | S | I | 5 | ψ | pb | pb |
|  | D-norleucine | T | I | 5 | ψ | pb | pb |
|  | D-norleucine | D | I | 5 | ψ | pb | pb |
|  | D-norleucine | E | I | 5 | ψ | pb | pb |
|  | D-norleucine | G | I | 5 | ψ | pb | pb |
| 345 | D-norleucine | Y | I | 5 | ψ | pb | ψ |
|  | D-norleucine | F | I | 5 | ψ | pb | ψ |
|  | D-norleucine | C | I | 5 | ψ | pb | ψ |
|  | D-norleucine | S | I | 5 | ψ | pb | ψ |
|  | D-norleucine | T | I | 5 | ψ | pb | ψ |
|  | D-norleucine | D | I | 5 | ψ | pb | ψ |
|  | D-norleucine | E | I | 5 | ψ | pb | ψ |
|  | D-norleucine | G | I | 5 | ψ | pb | ψ |
| 346-349 | Same pattern as families 342-345 with R3 = V | | | | | | |
| 350-353 | Same pattern as families 342-345 with R3 = L | | | | | | |
| 354-365 | Same pattern as families 342-353 with R1 = D norvaline | | | | | | |
| 366-377 | Same pattern as families 342-345 with R3 = D-lysine | | | | | | |
| 378-389 | Same pattern as families 342-345 with R3 = D-arginine | | | | | | |
| 390-401 | Same pattern as families 342-345 with R3 = D S-methyl cysteine | | | | | | |
| 402-457 | Same pattern as families 342-401 with n = 3 | | | | | | |
| 458-513 | Same pattern as families 342-401 with n = 4 | | | | | | |
| 514-569 | Same pattern as families 342-401 with n = 6 | | | | | | |

Arrows 1-3 may be
pb = peptide bond;
ψ = reduced peptide bond ($CH_2—NH_2$)

Alternatively, the analogs or growth factor mimics of the present invention may also be represented as comprised of four elements joined by covalent peptide or reduced peptide bonds, as follows:

I-II-III-IV where
I=an acid such as heptanoic, hexanoic, pentanoic, butyric, proprionic, acetic, benzoic, or substituted benzoic acid, and isoforms thereof; or D or L norleucine, lysine, arginine, norvaline, ornithine, or S-benzyl cysteine
II=a D or L cysteine, phenylalanine, aspartic acid, glutamic acid, serine, tyrosine, glycine, homocysteine, homoserine or homophenylalanine amino acid residue;
III=a D or L isoleucine, leucine, or valine amino acid residue; and
IV=amino-hexanoic, amino-pentanoic or amino butyric acid; wherein elements I, II, III and IV are joined by peptide or reduced peptide bonds.

In one embodiment, the analog is: hexanoic-tyrosine-isoleucine-(6)-amino-hexanoic amide. Using Formula I as a generic formula, for this particular analog, R1=hexanoyl; R2 is Tyr; R3 is Ile; and n=5. Alternatively, using the I-II-III-IV nomenclature, in this embodiment, I=hexanoic acid, II=Tyr; III=Ile; and IV=hexanoic amide.

Embodiments of the invention involve providing one or more HGF mimics to a subject in need thereof. Exemplary subjects or patients which might benefit from receiving therapy such as administration of the one or more HGF mimics described herein are generally mammals, and usually humans, although this need not always be the case, since veterinary and research related applications of the technology are also contemplated. Generally a suitable subject or patient in need of therapy is identified by, for example, a health care professional or professionals using known tests, measurements or criteria. For example, in the treatment for dementia, a subjects already having symptoms of dementia, or being at risk of developing symptoms of dementia will be identified. Similar identification processes will be followed for other diseases and/or disorders (e.g., cancer therapy, other cognitive dysfunction therapies, etc.). A suitable treatment protocol is then developed based on the patient, the disease and/or disorder and its stage of development, and the HGF mimic and its dosage and delivery format, as well as other relevant factors. The subject then receives treatment with HGF mimic. Embodiments of the invention also comprise one or more steps related to monitoring the effects or outcome of administration in order to evaluate the treatment protocol and/or to adjust the protocol as required or in a manner that is likely to provide more benefit, e.g. by increasing or decreasing doses of medication, or by changing the particular type of mimic that is administered, or by changing the frequency of dosing or the route of administration, etc. With particular reference to the embodiment of providing cognitive enhancement for example, while in some cases the improvement in cognition (or the prevention of loss of cognition) that occurs may be complete, e.g. the functioning of the patient returns to or remains normal (as assessed in comparison to suitable control subjects or standardized values obtained therefrom), this need not always be the case. Those of skill in the art will recognize that even a lower level of improvement in cognition may be highly beneficial to the patient, as may be the slowing of the progression of a disease, as opposed to a complete cure.

The methods of the invention involve administering compositions comprising the HGF mimics disclosed herein to a patient in need thereof. The present invention thus also provides compositions which comprise the HGF analogs/mimics as described herein, usually together with a pharmacologically suitable carrier or diluent. In some embodiments, one substantially purified HGF mimic is present in a composition; in other embodiments more than one HGF mimic is present, each HGF mimic being substantially purified prior to being mixed in the composition. The HGF mimics may be in the form of pharmaceutically acceptable salts, e.g. acid salts such as HCl, KCl, phosphate, or organic salts such as ammonium, etc. The preparation of pharmacologically suitable compositions for use as medicaments is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of HGF mimic in the formulations may vary. However, in general, the amount in the formulations will be from about 1% to about 99%.

The HGF mimic compositions (preparations) of the present invention may be administered by any of the many suitable means which are well known to those of skill in the art, including but not limited to: by injection, inhalation, orally, intravaginally, intranasally, by ingestion of a food or product containing the mimic, topically, as eye drops, via sprays, etc. In preferred embodiments, the mode of administration is orally or by injection. In addition, the compositions may be administered in conjunction with other treatment modalities such as other agents which are used to treat, for example, dementia or the conditions which cause dementia in the patient, examples of which include but are not limited to the administration of anti-depressants and psychoactive drugs, administration of dopamine and similar agents. Similarly, in cancer treatment modalities, the HGF mimics may be administered together with analgesics and other suitable drugs. Thus, in embodiments of the invention, one or more HGF mimics may be used in combination with one or more different bioactive drugs.

The amount of HGF inhibitor that is administered may be in the range of from about 0.1 to about 1,000 mg/kg, an preferably in the range of from about 1 to about 100 mg/kg, although as one of skill in the art will recognize, the precise amount may vary depending on one or more attributes of the drug recipient, including but not limited to: weight, overall health, gender, age, nationality, genetic history, other conditions being treated, etc., and larger or smaller doses are within the practice of this invention. Dosing may also take place periodically over a period of time, and the dosage may change (increase or decrease) with time.

The HGF mimics of the invention may be used to treat a variety of cognitive function disorders (cognitive dysfunction) as well as other disorders that are related to HGF activity or lack thereof. "Cognitive function" or "cognition" as used herein refers to a range of high-level brain functions, including but not limited to: the ability to learn and remember information; the ability to organize, plan, and problem-solve; the ability to focus, maintain, and shift attention as necessary; and to understand and use language; the ability to accurately perceive the environment; the ability to perform calculations. Such functions include but are not limited to memory (e.g. acquiring, retaining, and retrieving new information); attention and concentration (particularly divided attention); information processing (e.g. dealing with information gathered by the five senses); executive functions (e.g. planning and prioritizing); visuospatial functions (e.g. visual perception and constructional abilities); verbal fluency and speech (e.g. word-finding); general intellect (e.g. "intelligence"); long-term (remote) memory; conversational skills; reading comprehension; etc. Conversely, by "cognitive dysfunction" we mean the loss of such abilities. Losses may be measured, detected and/or diagnosed in any of the many ways known to those of ordinary skill in the art. Such methods include but are not limited to: the use of standardized testing administered by a professional (puzzles, word games or problems, etc.); by self-reporting and/or the reports of caretakers, friends and family members of an afflicted individual; by observation of the activities, life skills, habits and coping mechanisms of the individual by professional or lay persons; by the results of questionnaires administered to an afflicted individual; etc.

Such disorders may be caused, for example, by a decrease in synaptic connectivity and/or neuron density due to a variety of factors. In some embodiments, the loss is caused by a brain injury, e.g. traumatic brain injury. Traumatic brain injury, which is occurring at record levels as a result of wars and sporting activities, is characterized by reduced neuronal connectivity. Hence, the use of HGF mimetics represents a viable treatment option. Such brain injuries may be the result of an external trauma to the brain, e.g. caused by a high impact accident (e.g. a car accident, a fall, etc.), a shooting incident, a sports injury (e.g. caused by impact to the head such a boxers and football players experience); injuries received in combat, etc. Alternatively, such injuries may be the result of internal brain trauma, e.g. as the result of stroke, aneurism, surgical procedure, tumor, etc. or other types of conditions which result in lack of oxygen to the brain or to sections of the brain; injuries due to inhalation of toxic gases; due to aging of the brain; to diseases and disorders which exert a deleterious effect on the nervous system and/or brain, such as multiple sclerosis, Parkinson's disease, Huntington's disease, brain disorders such as schizophrenia, etc.

As a specific example of a therapy contemplated by embodiments of the invention, the HGF mimics may be used for the treatment of dementia. By "dementia" we mean a serious loss of cognitive ability in a previously unimpaired person, beyond what might be expected from normal aging. It may be static, the result of a unique global brain injury, or progressive, resulting in long-term decline due to damage or disease in the body. Although dementia is far more common in the geriatric population, it may occur in any stage of adulthood. For the purposes of embodiments of this invention, the term "dementia" may include and/or be caused by e.g. Alzheimer's disease, vascular dementia, dementia with Lewy bodies, etc. or combinations of these. In other embodiments of the invention, Alzheimer's disease may be excluded from this definition. Other causes of dementia which may be treated as described herein include but are not limited to hypothyroidism and normal pressure hydrocephalus. Inherited forms of the diseases which cause or are associated with dementia that may treated as described herein include but are not limited to: frontotemporal lobar degeneration, Huntington's disease, vascular dementia, dementia pugilistica, etc. In younger populations, progressive cognitive disturbance may be caused by psychiatric illness, alcohol or other drug abuse, or metabolic disturbances. Certain genetic disorders can cause true neurodegenerative dementia in younger populations (e.g. 45 and under). These include familial Alzheimer's disease, SCA17 (dominant inheritance); adrenoleukodystrophy (X-linked); Gaucher's disease type 3, metachromatic leukodystrophy, Niemann-Pick disease type C, pantothenate kinase-associated neurodegeneration, Tay-Sachs disease and Wilson's disease. Vitamin deficiencies and chronic infections may also occasionally mimic degenerative dementia. These include deficiencies of vitamin B12, folate or niacin, and infective causes including cryptococcal meningitis, HIV, Lyme disease, progressive multifocal leukoencephalopathy, subacute sclerosing panencephalitis, syphilis and Whipple's disease. With respect to rapidly progressive dementia, Creutzfeldt-Jakob disease typically causes a dementia which worsens over weeks to months, being caused by prions. The common causes of slowly progressive dementia also sometimes present with rapid progression, e.g. Alzheimer's disease, dementia with Lewy bodies, and frontotemporal lobar degeneration (including corticobasal degeneration and progressive supranuclear palsy).

In addition, encephalopathy or delirium may develop relatively slowly and result in dementia. Possible causes include brain infection (viral encephalitis, subacute sclerosing panencephalitis, Whipple's disease) or inflammation (limbic encephalitis, Hashimoto's encephalopathy, cerebral vasculitis); tumors such as lymphoma or glioma; drug toxicity (e.g. anticonvulsant drugs); metabolic causes such as liver failure or kidney failure; and chronic subdural hematoma. The dementia that is treated according to methods of the present invention may also be the result of other conditions or illnesses. For example, there are many medical and neurological conditions in which dementia only occurs late in the illness, or as a minor feature. For example, a proportion of patients with Parkinson's disease develop dementia, Cognitive impairment also occurs in the Parkinson-plus syndromes of progressive supranuclear palsy and corticobasal degeneration (and the same underlying pathology may cause the clinical syndromes of frontotemporal lobar degeneration). Chronic inflammatory conditions of the brain may affect cognition in the long term, including Behçet's disease, multiple sclerosis, sarcoidosis, Sjögren's syndrome and systemic lupus erythematosus. In addition, inherited conditions may also cause dementia alongside other features include: Alexander disease, Canavan disease, cerebrotendinous xanthomatosis, fragile X-associated tremor/ataxia syndrome, glutaric aciduria type 1, Krabbe's disease, maple syrup urine disease, Niemann Pick disease type C, Kufs' disease, neuroacanthocytosis, organic acidemias, Pelizaeus-Merzbacher disease, urea cycle disorders, Sanfilippo syndrome type B, and spinocerebellar ataxia type 2.

In addition to treating dementia, the HGF mimics of the invention may be used for neuroprotection and/or to treat neurodegenerative diseases, some of which also involve dementia as described above. For neuroprotection, the HGF mimics may be administered propylactically, i.e. prior to a subject's encounter with or exposure to a potential neurohazard. For example, the mimics may be administered prior to exposure to a drug, chemical or medical procedure that is known or likely to cause neuronal damage. With respect to the treatment of neurodegenerative diseases, the general pro-survival anti-apoptotic activity of HGF supports the use of HGF mimetics for treating neurodegenerative diseases including but not limited to Parkinson's disease, Huntington's disease, and amyotrophic lateral sclerosis (ALS), etc.

In addition, the mimics may be used for the treatment of "depression", by which we mean major depressive disorder (MDD) (also known as recurrent depressive disorder, clinical depression, major depression, unipolar depression, or unipolar disorder) and also depression that is characteristic of bipolar disorder, etc. Depression is ultimately a disease in which neurons and synaptic contacts are lost in the hippocampus. The capacity of HGF to induce new synaptic connections and stimulate neurogenesis in the hippocampus supports the use of HGF mimetics for the treatment of depression.

In addition, the cognitive abilities of persons afflicted with certain genetic predispositions to cognitive dysfunction may also be increased, e.g. persons with genetic disorders such as Down's syndrome, lack of proper brain development e.g. due to lack of oxygen before or during birth, various congenital disorders which interfere with brain development, etc.

As demonstrated in the Examples below, the HGF mimics can inhibit the HGF/Met system, and therefore can be used as anti-cancer agents. The HGF mimics may be used to attenuate malignant and metastatic transformations.

The HGF mimics have application in the therapy of Fibrotic Disease. Hepatic, renal, cardiac, and pulmonary fibrosis is a growing problem in our aging population. Unfortunately, the degradation of function that accompanies fibrotic changes is difficult to treat. The dramatic ability of HGF to inhibit or reverse tissue fibrosis suggests that orally-active HGF mimics provides a therapeutic option.

The HGF mimics have application in the therapy of Peripheral Vascular Disease: Lower Extremity Arterial Disease. Vascular disease resulting in poor perfusion is a common sequel of diabetes, obesity, and atherosclerosis. One treatment option is the induction of new collateral vessels in the effected organs and tissues. The potent angiogenic activity of HGF and HGF mimics can provide a clinical utility for the treatment of vascular insufficiency.

HGF mimics may also be used for Wound Healing. Defective wound healing is a hallmark of diabetics and burn victims. The ability of HGF to promote wound healing because of its angiogenic and mitogenic activities supports the use of HGF mimics to enhance the wound healing process. Data indicates that several HGF mimics are effective wound repair enhancers in both normal and diabetic individuals.

Without being bound by theory, it is believed that the likely mechanism underlying this marked pro-cognitive activity is augmented synaptic connectivity. This is likely due to an increase in miniature synaptic activity brought about by increasing dendritic spine densities and altering the morphological phenotype of postsynaptic spines.

Treatment of Dementia, Including Alzheimer's Disease (AD)

In one aspect, the HGF mimics described herein are used to treat dementia, e.g. to treat one or more symptoms of dementia. In other words, the mimics are used to alleviate (e.g. decrease, ameliorate, lessen, slow developemetn of, or even eliminate) symptoms of dementia. Types of dementia that may be treated as described herein include but are not limited to Alzheimer's Disease (AD), vascular dementia, dementia with Lewy bodies, mixed dementia, etc. Symptoms of dementia that may be treated include but are not limited to: memory loss, difficulty communicating, difficulty with complex tasks, difficulty with planning and organizing, difficulty with coordination and motor functions, problems with disorientation (such as getting lost), personality changes, inability to reason, inappropriate behavior, paranoia, agitation, hallucinations, etc.

In one embodiment, the invention provides methods of treating diseases and/or pathology caused by or characterized by the development or presence of Lewy bodies. The methods involve the administration of one or more HGF mimics of the invention, in an amount sufficient to treat, ameliorate, slow progression of, etc. disease symptoms.

In some aspects, the invention provides methods of treating dementia patients at various stages of dementia, and/or of slowing and/or preventing the progression of dementia to later stages of dementia, or even or reversing the "staging" from advanced to moderate or early, or from moderate to early, stage. For example, the quality of life of a subject can be greatly improved even though symptoms are not entirely removed, if more severe symptoms can be avoided. By "stages of dementia" we mean, for example: Early Stage Dementia (Mild Cognitive Impairment), which may be characterized by language difficulties (vocabulary recall, shrinking vocabulary, fluency, etc.); by loss or impairment of executive functions (such as attentiveness, planning, flexibility, abstract thinking, etc.); sematic memory loss (e.g. loss of meanings, understandings, and other concept-based knowledge); development of apathy; movement problems; etc. Moderate Stage Dementia is characterized by, for example, short term memory loss; long-term memory problems; irritability; aggression; delusion, and the like. Advanced Stage Dementia is characterized by, for example, mobility deterioration; severe apathy; etc. Use of the HGF mimics described herein results in cessation of progression of the disease from one stage to the next more severe stage, and may result in reversal from a severe stage to a less severe stage.

If the dementia is Alzheimer's disease, any of the seven commonly recognized stages thereof may be treated, symptoms thereof reversed or arrested without progression to a more severe stage, and/or the progression to more severe stages may be slowed. Recognized stages include: Stage 1: No impairment (normal function); Stage 2: very mild cognitive decline (may be normal age-related changes or earliest signs of Alzheimer's disease); Stage 3: mild cognitive decline (early-stage Alzheimer's can be diagnosed in some, but not all, individuals with these symptoms); Stage 4: moderate cognitive decline (mild or early-stage Alzheimer's disease); Stage 5: moderately severe cognitive decline (moderate or mid-stage Alzheimer's disease); Stage 6: severe cognitive decline (moderately severe or mid-stage Alzheimer's disease); Stage 7: very severe cognitive decline (severe or late-stage Alzheimer's disease).

The HGF mimics may be administered together with one or more additional treatments for dementia, including but not limited to: administration of cholinesterase inhibitors, memantine, etc.

Treatment of Parkinson's Disease

In one aspect, the HGF mimics of the invention are used to treat Parkinson's disease (PD), e.g. to treat one or more symptoms of PD. PD is well know to affect movement, producing motor symptoms, and also to cause non-motor symptoms, which include autonomic dysfunction, neuropsychiatric problems (mood, cognition, behavior or thought alterations, personality changes, etc.), and sensory and sleep difficulties. Particular symptoms that can be treated (e.g. prevented, restored, alleviated, lessened, decreased, or in some cases eliminated). In other cases, the progress of the disease, e.g. the progress of the development of one or more symptoms, is slowed or arrested. In such cases, the subject still technically has PD, but the quality of life of the subject is significantly improved because the progression of symptoms is slowed, or even stopped (arrested) at an earlier stage than would be possible without administration of the HGF mimic(s), e.g. symptoms may be relegated to being an "annoyance" without being debilitating. Thus, the development of severe and debilitating symptoms may be avoided. PD symptoms that are treated include but are not limited to the so-called "Parkinsonian gait". By "gait" we mean a subject's manner of walking or moving on foot, which is generally characterized by a particular sequence of foot and/or leg movements. Other PD symptoms that can be treated include but are not limited to: tremor or shaking (including so-called "pill-rolling" movements), rigidity, slowness of movement, and postural instability; bradykinesia (slowness of movement, including difficulty planning, initiating and executing movement, as well as hindrance of the performance of sequential and simultaneous movement); rigidity, i.e. stiffness and resistance to limb movement caused by increased muscle tone and/or an excessive and continuous contraction of muscles, which may be uniform (lead-pipe rigidity) or ratchety (cogwheel rigidity), and which may be associated with joint pain; postural instability, characterized by impaired balance and frequent falls, and secondarily to bone fractures; etc. Other recognized motor signs and symptoms include gait and posture disturbances such as festination (rapid shuffling steps and a forward-flexed posture when walking), speech and swallowing disturbances including voice disorders, mask-like face expression or small handwriting, although the range of possible motor problems that can appear is large. Further symptoms that can be treated include: neuropsychiatric disturbances which can range from mild to severe, including disorders of speech, cognition (e.g. decline of cognitive abilities), mood, behaviour, and thought (e.g. executive dysfunction, which can include problems with planning, cognitive flexibility, abstract thinking, rule acquisition, initiating appropriate actions and inhibiting inappropriate actions, and selecting relevant sensory information, fluctuations in attention and slowed cognitive speed, memory (especially in recalling learned information), visuospatial difficulties e.g. facial recognition and perception of the orientation of drawn lines; dementia; etc. In addition, other symptoms that can be treated include behavior and mood alterations (e.g, depression, apathy, anxiety, etc.) which may manifest as decreased facial expression, decreased movement, a state of indifference, and quiet speech; Other impairments that are treated include: sleep problems (e.g. daytime drowsiness, disturbances in REM sleep, insomnia, etc.; orthostatic hypotension (low blood pressure upon standing); oily skin; excessive sweating; urinary incontinence; altered sexual function; constipation and gastric dysmotility; various eye and vision abnormalities such as decreased blink rate, dry eyes, deficient ocular pursuit (eye tracking) and saccadic movements (fast automatic movements of both eyes in the same direction), difficulties in directing gaze upward, and blurred or double vision; changes in perception including an impaired sense of smell, sensation of pain and paresthesia (skin tingling and numbness, among others. Use of the present HGF mimics also advantageously avoid the development of disorders of impulse control behaviors (such as medication overuse and craving, binge eating, hypersexuality, or pathological gambling) and various psychotic symptoms (e.g. hallucinations, delusions, etc.) that can appear in PD and are related to the medications used to manage the disease.

In one aspect, the invention provides methods of preventing or treating muscular weakness in a patient with Parkinson's disease and/or of improving or restoring muscular strength of a patient with Parkinson's disease, by administering one or more hepatocyte growth factor mimics as described herein. Muscular strength typically refers to the amount of force that muscles can exert against some form of resistance, e.g. in a single effort, and may also be known as physical strength. Muscular strength is utilized e.g. when lifting things, standing up from a sitting position, etc., and an improvement in muscular strength due to treatment with the HGF mimics described herein confers many benefits on PD patients.

For each PD treatment method described herein the HGF mimics may be administered together with one or more additional treatments for PD, including but not limited to: deep brain stimulation, administration of levadopa (L-dopa), etc.

The foregoing Examples are provided in order to illustrate various embodiments of the invention, but should not be interpreted as limiting the invention in any way.

EXAMPLES

Example 1

Regulation of Synaptogenesis by Dihexa and Nle1-AngIV

The tetrapeptide (Nle1-YIH) and tripeptide (Nle 1-YI) fragments of the Nle1-AngIV analog of AngIV were previously found to be the smallest active fragments capable of overcoming scopolamine-induced cognitive dysfunction in a spatial learning task. Using the tripeptide as a new template, additional active analogues were synthesized with improved metabolic stability, blood brain barrier permeability, and oral activity. In this Example, we show the characterization of the novel, orally active, angiotensin IV analogue Dihexa.

Materials and Methods
Animals and Surgery.

Male Sprague-Dawley rats (Taconic derived) weighing 390-450 g were maintained with free access to water and food (Harland Tekland F6 rodent diet, Madison, Wis.) except the night prior to surgery when food was removed. Each animal was anesthetized with Ketamine hydrochloride plus Xylazine (100 and 2 mg/kg im. respectively; Phoenix Scientific; St. Joseph, Mo., and Moby; Shawnee, Kans.). An intracerebroventricular (icv) guide cannula (PE-60, Clay Adams; Parsippany, N.Y.) was stereotaxically positioned (Model 900, David Kopf Instruments; Tujunga, Calif.) in the right hemisphere using flat skull coordinates 1.0 mm posterior and 1.5 mm lateral to bregma (refer to Wright et al. 1985). The guide cannula measured 2.5 cm in overall length and was prepared with a heat bulge placed 2.5 mm from its beveled tip, thus acting as a stop to control the depth of penetration. Once in position, the cannula was secured to the skull with two stainless-steel screws and dental cement. Post-operatively the animals were housed individually in an American Accreditation for Laboratory Animal Care-approved vivarium maintained at 22±1° C. on a 12-h alternating light/dark cycle initiated at 06:00 h. All animals were hand gentled for 5 min per day during the 5-6 days of post-surgical recovery. Histological verification of cannula placement was accomplished by the injection of 5 µl fast-green dye via the guide cannula following the completion of behavioral testing. Correct cannula placement was evident in all rats utilized in this study.

Behavioral Testing.

The water maze consisted of a circular tank painted black (diameter: 1.6 m; height: 0.6 m), filled to a depth of 26 cm with 26-28° C. water. A black circular platform (diameter: 12 cm; height: 24 cm) was placed 30 cm from the wall and submerged 2 cm below the water surface. The maze was operationally sectioned into four equal quadrants designated NW, NE, SW, and SE. For each rat the location of the platform was randomly assigned to one of the quadrants and remained fixed throughout the duration of training. Entry points were at the quadrant corners (i.e. N, S, E, and W) and were pseudorandomly assigned such that each trial began at a different entry point than the preceding trial. Three of the four testing room walls were covered with extra-maze spatial cues consisting of different shapes (circles, squares, triangles) and colors. The swimming path of the animals was recorded using a computerized video tracking system (Chromotrack; San Diego Instruments, CA). The computer displayed total swim latency and swim distance. Swim speed was determined from these values.

Each member of the treatment groups in the scopolamine studies received an icv injection of scopolamine hydrobromide (70 nmol in 2 µl aCSF over a duration of 20 s) 30 min prior to testing followed by Dihexa 10 min prior to testing. Control groups received scopolamine or aCSF 20 min prior to testing followed by aCSF 10 min prior testing. The behavioral testing protocol has been described previously in detail (Wright et al. 1999). The rats in the aged rat study on received Dihexa of aCSF (control group).Briefly, acquisition trials were conducted on 8 consecutive days with 5 trials/day. On the first day of training the animal was placed on the platform for 30 s prior to the first trial. Trials commenced with the placement of the rat facing the wall of the maze at one of the assigned entry points. The rat was allowed a maximum of 120 s to locate the platform. Once the animal located the platform it was permitted a 30 s rest period on the platform. If the rat did not find the platform, the experimenter placed the animal on the platform for the 30 s rest period. The next trial commenced immediately following the rest period.

Following day 8 of acquisition training, one additional trial was conducted during which the platform was removed (probe trial). The animal was required to swim the entire 120 s to determine the persistence of the learned response. Total time spent within the target quadrant where the platform had been located during acquisition and the number of crossings of that quadrant was recorded. Upon completion of each daily set of trials the animal was towel-dried and placed under a 100 watt lamp for 10-15 min and then returned to its home cage.

Hippocampal Cell Culture Preparation.

Hippocampal neurons ($2 \times 10^5$ cells per square cm) were cultured from P1 Sprague Dawley rats on plates coated with poly-L-lysine from Sigma (St. Louis, Mo.; molecular weight 300,000). Hippocampal neurons were maintained in Neurobasal A media from Invitrogen (Carlsbad, Calif.) supplemented with B27 from Invitrogen, 0.5 mM L-glutamine, and 5 mM cytosine-D-arabinofuranoside from Sigma added at 2 days in vitro. Hippocampal neurons were then cultured a further 3-7 days, at which time they were either transfected or treated with various pharmacological reagents as described in (Wayman, Davare et al. 2008).

Transfection.

Neurons were transfected with mRFP-β-actin on day in vitro 6 (DIVE) using LipofectAMINE™ 2000 (Invitrogen) according to the manufacturer's protocol. This protocol yielded the desired 3-5% transfection efficiency thus enabling the visualization of individual neurons. Higher efficiencies obscured the dendritic arbor of individual neurons. Expression of fluorescently tagged actin allowed clear visualization of dendritic spines, as dendritic spines are enriched in actin. On DIV7 the cells were treated with vehicle ($H_2O$) or peptides (as described in the text) added to media. On DIV12 the neurons were fixed (4% paraformaldehyde, 3% sucrose, 60 mM PIPES, 25 mM HEPES, 5 mM EGTA, 1 mM $MgCl_2$, pH 7.4) for 20 min at room temperature and mounted. Slides were dried for at least 20 hours at 4° C. and fluorescent images were obtained with Slidebook 4.2 Digital Microscopy Software driving an Olympus IX81 inverted confocal microscope with a 60× oil immersion lens, NA 1.4 and resolution 0.280 µm Dendritic spine density was measured on primary and secondary dendrites at a distance of at least 150 µm from the soma. Five 50 µm long segments of dendrite from at least 10 neurons per data point were analyzed for each data point reported. Each experiment was repeated at least three times using independent culture preparations. Dendrite length was determined using the National Institutes of Health's Image J 1.41o program (NIH, Bethesda, Md.) and the neurite tracing program Neuron J (Meijering, Jacob et al. 2004) Spines were manually counted.

Organotypic Hippocampal Slice Culture Preparation and Transfection.

Hippocampi from P4 Sprague Dawley rats were cultured as previously described (Wayman, hnpey et al. 2006). Briefly, 400 µm slices were cultured on (Milipore, Billerica, Mass.) for 3 days after which they were biolistically transfected with tomato fluorescent protein (TFP) using a Helios Gen Gun (BioRad, Hercules, Calif.), according to the manufacturer's protocol, to visualize dendritic arbors. Following a 24 hour recovery period slices were stimulated with vehicle ($H_2O$), 1 pM Nle1-AngIV or Dihexa for 2 days. Slices were fixed and mounted. Hippocampal CA1 neuronal processes were imaged and measured as described above.

Immunocytochemistry.

Transfected neurons were treated, fixed and stained. Briefly, cells were permeablized with 0.1% Triton X-100 detergent (Bio-Rad; Hercules, Calif.) for 10 minutes. An 8% bovine serum albumin (Intergen Company; Burlington, Mass.) in PBS was used to prevent non-specific binding for one hour at R.T.; Primary antibody incubations were at a 1:2500 dilution (see below) in 1% BSA in PBS at 4° C. overnight. Secondary antibody, 1:3000 Alexafluor 488 goat-anti-mouse (Invitrogen: Carlsbad, Calif.) was applied for two hours at room temperature. Coverslips were mounted with ProLong Gold anti-fade reagent (Invitrogen; Carlsbad, Calif.) and all washes were done with PBS. Imaging and analysis were performed as described above. For presynaptic excitatory transmission the VGLUT1 (Synaptic Systems, Goettingen, Germany) marker (Balschun, Moechars et al.) was employed and for general presynaptic transmission synapsin1 (Synaptic Systems, Goettingen, Germany) (Ferreira and Rapoport 2002) was applied. A postsynaptic function was established by PSD-95 (Milipore, Billerica, Mass.) (El-Husseini, Schnell et al. 2000). In each instance the total number of spines was counted for the treatment groups, control, Nle1-AngIV and Dihexa, to ensure an active phenotype. The total number of actin enriched spines adjacent to VGLUT1 or Synapsin were counted and converted to a percentage as the percent correlation of treatment-induced spines to presynaptic markers is a strong indicator of ability to transmit excitatory signals. In our application the number of correlations consisted of red fluorescent-tagged actin spines against green PSD-95 immunopositive puncta which, when merged, resulted in an orange spine.

Whole-Cell Recordings.

Patch-clamp experiments were performed on mRFP-β-actin transfected cultured hippocampal neurons (vehicle control) and on transfected hippocampal neurons with 1 pM Nle1-AngIV or Dihexa 5 day pretreatment. Recordings were taken from neurons that were pyramidal-like in shape (~20 µm cell bodies and asymmetric dendrite distribution). The time after transfection was 6 days. The culture medium was exchanged by an extracellular solution containing (in mM) 140 NaCl, 2.5 KCl, 1 $MgCl_2$, 3 $CaCl_2$, 25 glucose, and 5 HEPES; pH was adjusted to 7.3 with KOH; osmolality was adjusted to 310 mOsm. Cultures were allowed to equilibrate in a recording chamber mounted on inverted microscope (IX-71; Olympus optical, Tokyo) for 30 min before recording.

Transfected cells were visualized with fluorescence (Olympus optical). Recording pipettes were pulled (P-97 Flaming/Brown micropipette puller; Sutter Instrument, Novato, Calif.) from standard-wall borosilicate glass without filament (OD=1.5 mm; Sutter Instrument). The pipette-to-bath DC resistance of patch electrodes ranged from 4.0 to 5.2 MΩ, and were filled with a internal solution of the following composition (in mM): 25 CsCl, 100 CsCH$_3$O$_3$S, 10 phosphocreatine, 0.4 EGTA, 10 HEPES, 2 MgCl$_2$, 0.4 Mg-ATP, and 0.04 Na-GTP; pH was adjusted to 7.2 with CsOH; osmolality was adjusted to 296-300 mOsm. Miniature EPSCs (mEPSCs) were isolated pharmacologically by blocking GABA receptor chloride channels with picrotoxin (100 μM; Sigma), blocking glycine receptors with strychnine (1 μM; Sigma), and blocking action potential generation with tetrodotoxin (TTX, 500 nM; Tocris). Recordings were obtained using a Multiclamp 700B amplifier (Molecular Devices, Sunnyvale, Calif.). Analog signals were low-pass Bessel filtered at 2 kHz, digitized at 10 kHz through a Digidata 1440A interface (Molecular Devices), and stored in a computer using Clampex 10.2 software (Molecular Devices). The membrane potential was held at −70 mV at room temperature (25° C.) during a period of 0.5-2 h after removal of the culture from the incubator. Liquid junction potentials were not corrected. Data analysis was performed using Clampfit 10.2 software (Molecular Devices), and Mini-Analysis 6.0 software (Synaptosoft Inc.; Fort Lee, N.J.). The criteria for successful recording included the electrical resistance of the seal between the outside surface of the recording pipette and the attached cell >2 GΩ, neuron input resistance >240 MΩ. The mEPSCs had a 5-min recording time.

Results

Figure 1B:
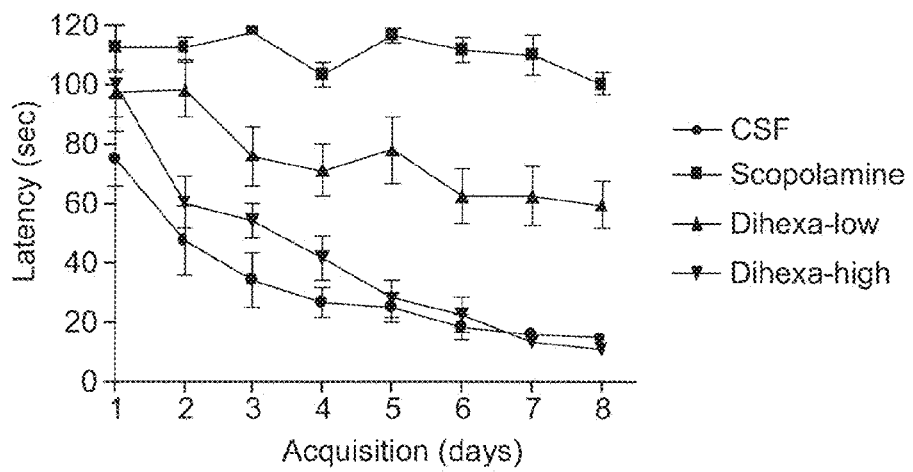
Figure 1C:
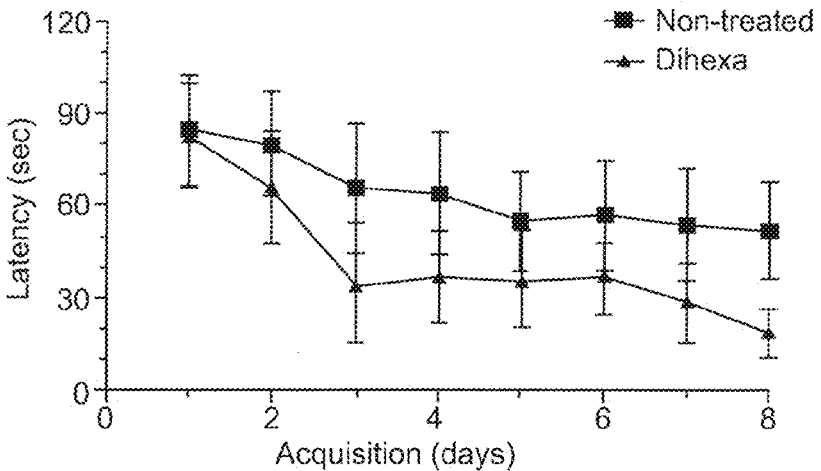

Nle1-AngIV has long been known to be a potent cognitive enhancing agent but is limited in terms of clinical utility by its metabolic instability ($t_{1/2}$=1.40 minutes in rat serum). In order to exploit the pro-cognitive properties of AngIV like molecules more metabolically stable analogs needed to be developed. As part of this development process Dihexa (N-hexanoic-Tyr-Ile-(6)-aminohexanoic amide) was synthesized and characterized ($t_{1/2}$=330 minutes in rat serum). To determine if the stabilized analog, Dihexa still possessed pro-cognitive/anti-dementia activity it was tested in two dementia models—the scolpamine amnesia and the aged rat models. These studies demonstrated that Dihexa was able to reverse the cognitive deficits observed in both models. Dihexa delivered either intracerebroventricularly or orally by gavage improved water maze performance reaching performance levels seen in young healthy rats. In FIG. 1A Dihexa delivered at 100 pmoles (n=8, p<0.01) but not 10 pmoles reversed scopolamine-dependent learning deficits as evidenced by an escape latency equivalent to non-scopolamine treated controls. Similar results were seen when Dihexa was delivered orally (FIG. 1B) at both low (1.25 mg/kg/day) and high (2 mg/kg/day). The high dose group's performance was no different than controls (n=8, p<0.01). Randomly grouped aged rats (20-24 weeks) included both sexes were similarly treated with oral Dihexa over the 8 day test period (n=8) and compared to untreated controls (FIG. 1C). The results indicate that the treated rats preformed significantly better in the water maze than untreated rats. (p<0.05).

Figure 2A:
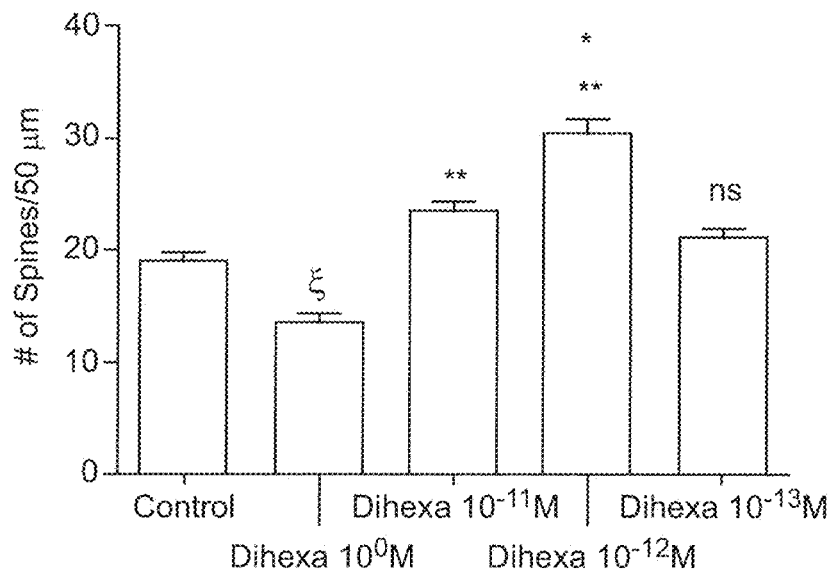
FIGS. 2A and B. Dihexa and $Nle^1$-AngIV dose-dependently stimulate spinogenesis. A) Dihexa and B) $Nle^1$-AngIV increase spine density in mRFP-β-actin transfected hippocampal neurons in a dose-dependent manner. Neurons were stimulated with Dihexa or $Nle^1$-AngIV over a 5 day period at a wide range of concentrations. Data obtained from separate cultures; cultures were 12 days old at time of fixing. The number of dendritic spines on representative 50 μm dendrite segments were hand counted. =p<0.05 and *=p<0.001; n=50; mean±S.E.M.; ξ=significantly different from control.
Figure 2B:
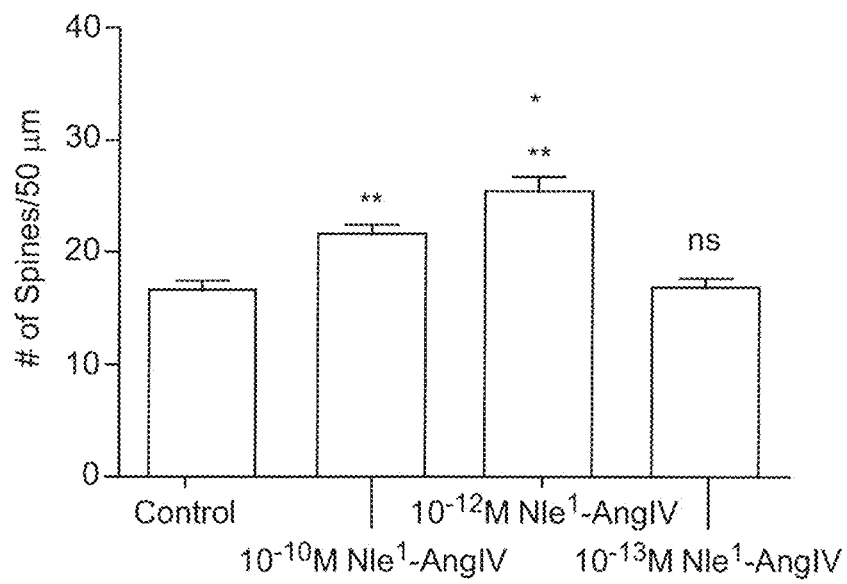

One hypothesis that was put forward to explain the pro-cognitive effects of Nle1-AngIV and Dihexa was that they were acting as hepatocyte growth factor mimetics and as such may be supporting he expansion of neuronal connectivity by inducing the growth of dendritic spines and the establishment of numerous new synapses. To determine the influence of Dihexa on spinogenesis and synaptogenesis in high density mRFP-β-actin transfected hippocampal neuronal cultures was assayed. Actin-enriched spines increased in response to Dihexa and Nle1-AngIV treatment in a dose-dependent manner (FIGS. 2A and B). An apparent ceiling effect was produced by $10^{-12}$ M Dihexa application (mean±S.E.M.; 30 spines per 50 μm dendrite length vs. 19 for control; ***=P<0.001; n=50 and 100 respectively) while the results of a $10^{-13}$ M dose were not significantly different from control treated neurons (mean±S.E.M.; 21 spines per 50 μm dendrite for both groups vs. 19 for control; *=P<0.05; n=95 and 100 respectively). They were however statistically different from the $10^{-12}$ M Dihexa dose. Neurons receiving a $10^{-10}$ M dose of Dihexa had fewer spines than vehicle treated neurons (Mean±S.E.M.; 11 spines per 50 μm dendrite length vs. 19 for control; #=P<0.01; n=50 and 100 respectively). Nle1-AngIV similarly induced a dose-dependent increase is spine density with a marked difference in the $10^{-10}$ M dose which promoted spinogenesis (mean±S.E.M.; 22 spines per 50 μm dendrite length vs. 17 for control; =P<0.01; n=50). Maximal increases in spine density were again observed following treatment with a $10^{-12}$ M dose (mean±S.E.M.; 25 and 26 spines per 50 μm dendrite length respectively vs. 17 for control; =P<0.01; n=50). The $10^{-13}$ M dose of Nle1-AngIV also had no effect on basal spine numbers (mean±S.E.M.; 17 spines per 50 μm dendrite length vs. 17 for control; **=P<0.01; n=50).

The effects of a long-term application (5 days) of the AT4 agonists Dihexa and Nle1-AngIV were compared to an acute application of the agonists (30 minutes) at the biologically effective dose of $10^{-12}$ M (FIG. 3A-E). The results revealed a near 3-fold increase in the number of spines stimulated by Dihexa and greater than 2-fold increase for Nle1-AngIV stimulated spines following a 5 day treatment (FIG. 3D). Both treatment groups differed significantly from the vehicle control group for which the average number of spines per 50 μm dendrite length was 15. The average number of spines for the Dihexa and Nle1-AngIV treated groups was 41 and 32 spines per 50 μM dendrite lengths, respectively (mean±S.E.M., n=200; *=P<0.001 by one-way ANOVA and Tukey post hoc test). The behavioral data (data not shown) suggest a quick mechanism of action is taking place during acquisition of the spatial memory task. Therefore the ability of both Dihexa and Nle1-AngIV to promote spinogenesis was measured by an acute 30 minute application on the final day of culturing (FIG. 3E). The acute 30 minute application of Dihexa and Nle1-AngIV, on the 12th day in vitro (DIV 12) reveals a significant increase in spines compared to 30 minute vehicle treated neurons (Dihexa mean spine numbers per 50 μm dendrite length=23.9±S.E.M.; Nle1-AngIV mean spine numbers=2.6±S.E.M.; mean spine numbers for vehicle control treated neurons=17.4±S.E.M.; n=60; *=p<0.0001 by one-way ANOVA followed by Tukey post-hoc test).

Figure 4:
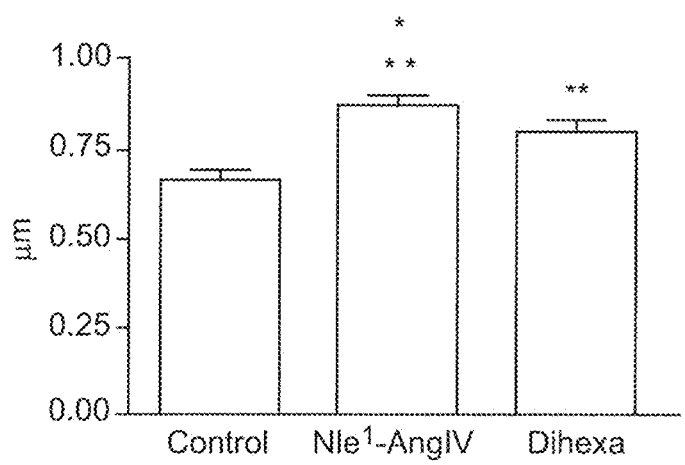
FIG. 4. Nle1-AngIV and Dihexa increase spine head width. The width of the spine head was measured as an indication of synaptic strength. Spine heads with a greater surface area can accommodate more neurotransmitter receptors and are more likely to form functional synapses. The AngIV analogue treatment-induced increase in spine head width suggests facilitated neurotransmission. ***=p<0.001; mean±S.E.M.; n=100.

Strong correlations exist between spine size, persistence of spines, number of AMPA-receptors and synaptic efficacy. A correlation between the existence of long-term memories to spine volume has also been suggested (Kasai, Fukuda et al., 2001; Yasumatsu, Matsuzaki et al. 2008). With these considerations in mind spine head size measurements were taken. Results indicate that $10^{-12}$ M doses of Dihexa and Nle1-AngIV increased spine head width (FIG. 4). Average spine head width for Nle1-AngIV=0.87 μm (*=p<0.001; mean±S.E.M.) and Dihexa=0.80 μm (=P<0.01; mean±S.E.M.) respectively compared to control head size (0.67 μm).

Dihexa and Nle1-AngIV Mediate Synaptogenesis

To quantify synaptic transmission, mRFP-β-actin transfected neurons were immuno-stained against synaptic markers. Hippocampal neurons were stimulated for 5 days in vitro with $10^{-12}$ M Dihexa or Nle1-AngIV (FIG. 5A-F). Nle1-AngIV and Dihexa's neurotransmitter patterns were probed for excitatory synaptic transmission by staining against the glutamatergic presynaptic marker Vesicular Glutamate Transporter 1 (VGLUT1) (Balschun, Moechars et al. 2010). The universal presynaptic marker Synapsin was employed to measure juxtaposition of the newly formed spines with presynaptic boutons (Ferreira and Rapoport 2002). PSD-95 served as a marker for the postsynaptic density (El Husseini, Schnell et al. 2000).

Figure 5A:
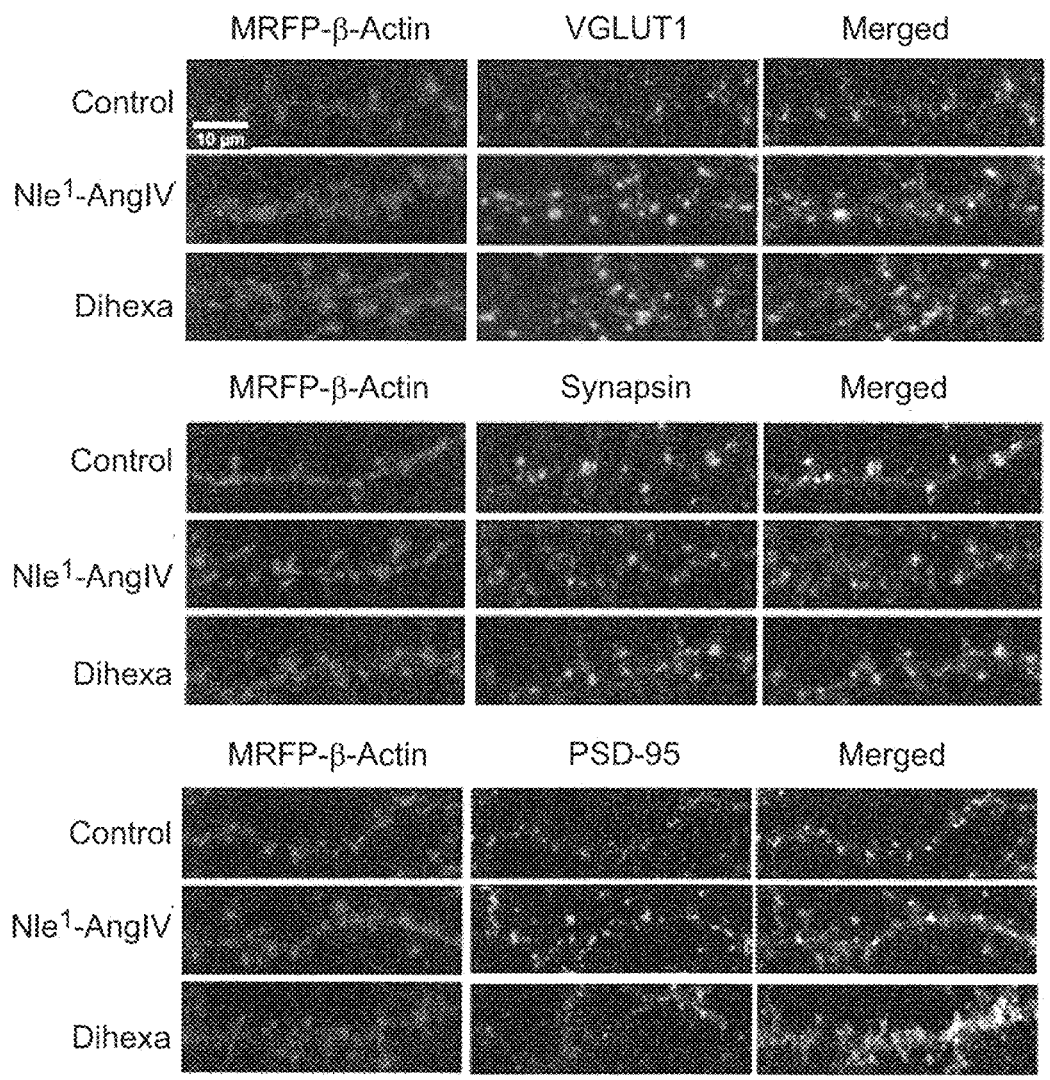
FIG. 5A-G. A) Neurotransmitter patterns for Nle1-AngIV and Dihexa stimulated neurons. Dihexa and Nle1-AngIV treated neurons were immunostained for the universal presynaptic marker synapsin and the glutamatergic presynaptic marker VGLUT1 and the postsynaptic marker PSD-95. The percent correlation between the postsynaptic spines and presynaptic puncta were measured as an indication of functional synapses. B) Bar graph representing the percent correlation of treatment-induced postsynaptic spines to the general presynaptic marker Synapsin. No significant differences between the stimulated neurons and vehicle control treated neurons were observed (P>0.05; mean±S.E.M.; n=25) suggesting a majority of the presynaptic input is glutamatergic. C) Bar graph representing an increase in the number of spines following treatment with vehicle, Nle1-AngIV or Dihexa, ensuring an active phenotype (*=P<0.001; mean±S.E.M.; n=25). D) Bar graph representing the percent correlation of treatment-induced postsynaptic spines to the glutamatergic presynaptic marker VGLUT1. A high percent correlation between the presynaptic marker and the postsynaptic spines suggests that functional connections are formed (P>0.05; mean±S.E.M.; n 25). E) Bar graph representing an increase in the number of spines following treatment with vehicle, Nle1-AngIV or Dihexa. This ensures an active phenotype in the neurons (*=P<0.001; mean±S.E.M.; n=25). F) Bar graph representing the percent correlation of treatment-induced postsynaptic spines to the postsynaptic marker PSD-95. No significant differences (P>0.05; mean±S.E.M.; n=25) between the postsynaptic marker PSD-95 and the postsynaptic spines suggest that the newly formed spines have a functional postsynaptic element. G) Bar graph representing an increase in the number of spines following treatment with vehicle, Nle1-AngIV or Dihexa, ensuring health of the neurons (***=P<0.001; mean±S.E.M.; n=25).
Figure 5B:
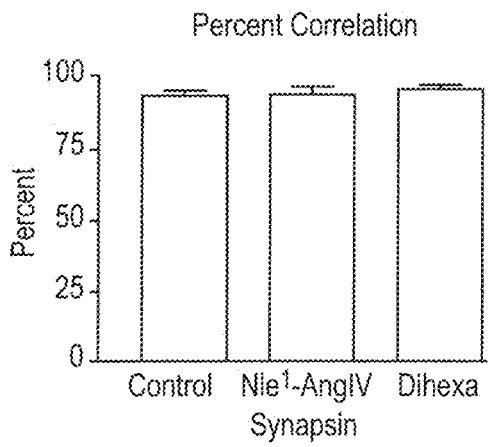
Figure 5C:
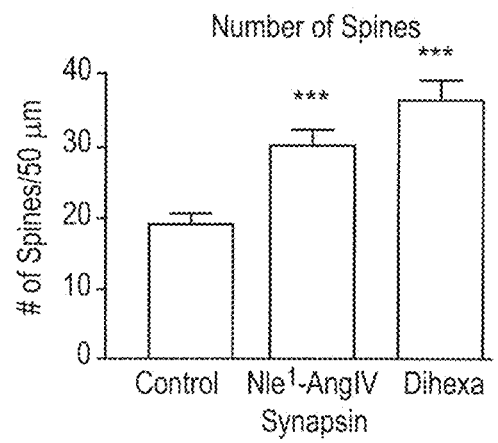
Figure 5D:
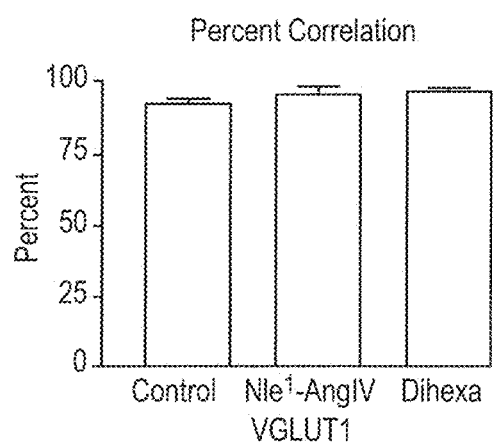
Figure 5E:
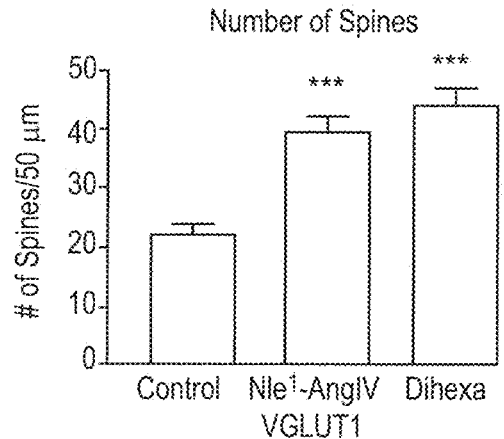
Figure 5F:
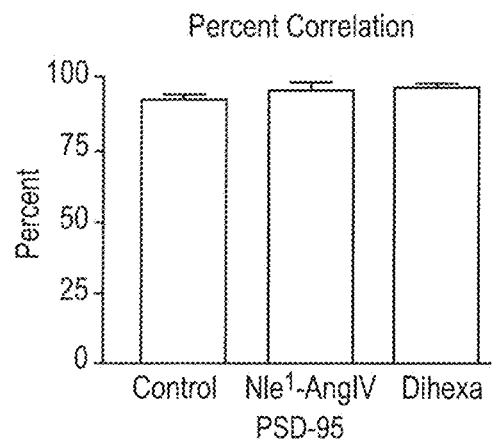
Figure 5G:
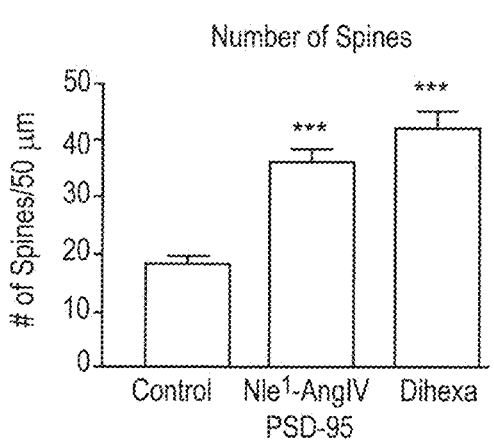

Dihexa and Nle1-AngIV treated neurons significantly augmented spinogenesis; mean spine numbers per 50 µm dendrite length for Nle1-AngIV=39.4; mean spine numbers per 50 µm dendrite length for Dihexa=44.2; mean spine numbers per 50 µm dendrite length for vehicle treated neurons=23.1 (mean±S.E.M., ***=P<0.001) (FIGS. 3B, D and F and Table 4). The percent correlation for the newly formed spines to the synaptic markers was calculated as a measure for the formation of functional synapses. Dihexa and Nle1-AngIV treatment-induced spines did not differ from control treated neurons in percent correlation to VGLUT1, Synapsin or PSD-95 (P>0.05) (FIGS. 5A, C and E and Table 4).

TABLE 4

Summary of the percent correlation to markers of synaptic components and the number of spines induced by Dihexa and Nle1-AngIV treatment.

| Treatment | Control | Nle1-AngIV | Dihexa |
|---|---|---|---|
| Number of spines/50 µm | 22 | 39 | 44 |
| % Correlation VGLUT1 | 95.2 | 95.1 | 94.4 |
| Number of spines/50 µm | 19 | 31 | 37 |
| % Correlation Synapsin | 93.4 | 94.2 | 96.3 |
| Number of spines/50 µm | 18 | 36 | 43 |
| % Correlation PSD-95 | 98.03 | 97.38 | 98.71 |

The total number of spines for each treatment group is indicated as the number of spines per 50 µm dendrite length. The percent correlation of the presynaptic marker Synapsin, the glutamatergic presynaptic marker VGLUT1 or the postsynaptic component PSD-95 is reported directly below.
N = 25 for each treatment group.

Figure 6A:
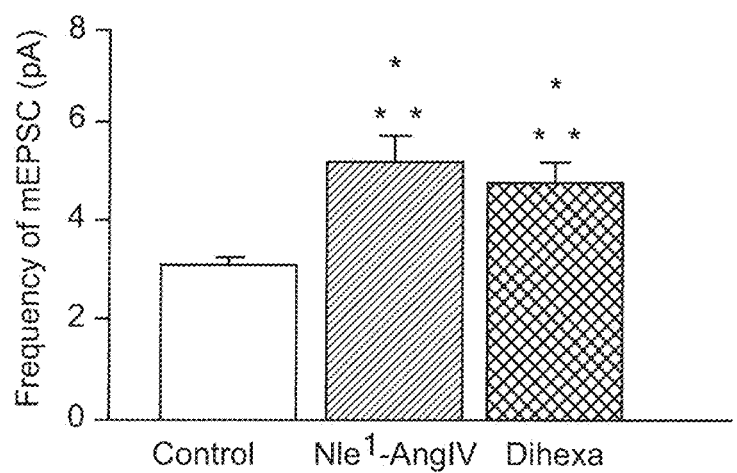
FIGS. 6A and B. Mini-excitatory postsynaptic currents (mEPSCs) in dissociated hippocampal neurons. Nle1-AngIV and Dihexa treatment increase the frequency of mini-excitatory postsynaptic currents (mEPSCs). Recordings were done on dissociated hippocampal neurons treated with vehicle, $10^{-12}$ M Nle1-AngIV or Dihexa for 5 days prior to recording. The currents recorded were spontaneous bursts of AMPA-mediated synaptic transmission in the absence of action potentials carried in the presence of strychnine, picrotoxin and tetrodotoxin. A) Representative traces of mEPSC recordings from Nle1-AngIV or Dihexa treated hippocampal neurons. B) Bar graph representing the increase in AMPA-mediated frequencies from Nle1-AngIV or Dihexa treated hippocampal neurons. The increased frequencies indicate that spines induced by Nle1-AngIV or Dihexa support functional synapses. ***=p<0.001; ±S.E.M.; n=25.
Figure 6B:
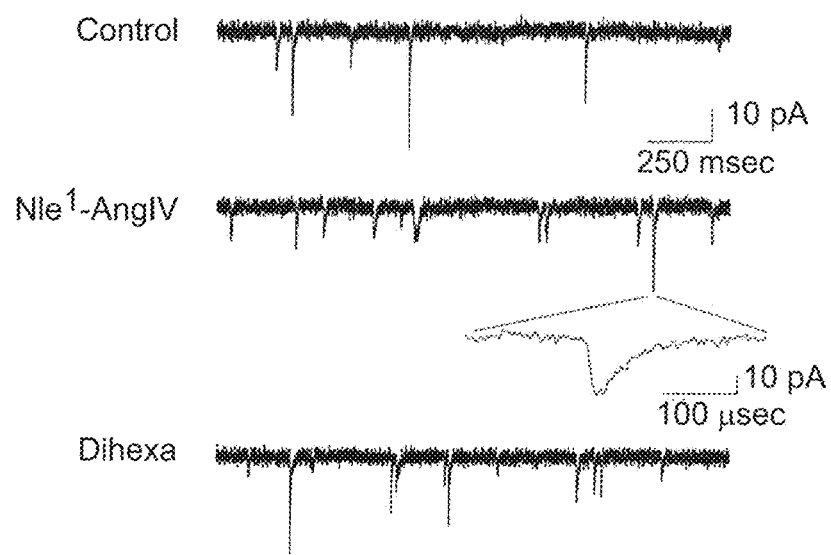

The above results suggest that the newly formed dendritic spines produced by Dihexa and Nle1-AngIV treatment are creating functional synapses. To further support this conclusion, mini postsynaptic excitatory currents (mEPSCs), the frequency of which corresponds to the number of functional synapses were recorded from mRFP-β-actin transfected hippocampal neurons. A near two-fold increase in the AMPA-mediated currents was measured following treatment with 10-12 M Nle1-AngIV and Dihexa (FIGS. 6A and B). The mean frequency of AMPA-mediated mEPSCs recorded from vehicle treated neurons was 3.06±0.23 Hz from 33 cells. Nle1-AngIV induced a 1.7 fold increase over percent control frequency (5.27±0.43 Hz from 25 cells; Mean±S.E.M.; *=P<0.001 vs. control group and Dihexa produced a 1.6 fold increase (4.82±0.34 Hz from 29 cells; * P<0.001 vs. control group confirming an amplification of functional synapses. No differences in amplitude, rise- or decay-times were observed (data not shown) which suggests that the individual properties of the synapse were not altered.

Figure 7A:
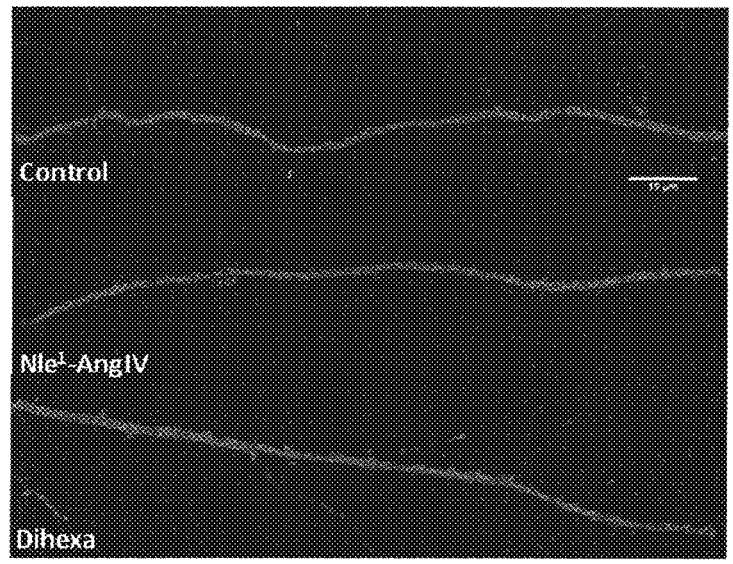
FIGS. 7A and B. Evaluation of Nle1-AngIV- and Dihexa-dependent spinogenesis in CA1 hippocampal neurons from rat organotypic hippocampal slice cultures. Nle1-AngIV- and Dihexa were found to support spinogenesis in CA1 hippocampal neurons. Organotypic hippocampal slice cultures (400 µm thicknesses), representing a more intact environment, were biolistically transfected with the soluble red fluorescent protein Tomato. CA1 hippocampal neurons were selected for evaluation because of their known plastic response during learning. Slices were obtained from postnatal day 5 rats. A) Representative images of CA1 neuronal dendrites from Tomato transfected hippocampal slices. Images represent a 2 day treatment with 10-12 M Nle1-AngIV or Dihexa. B) Treatment-induced spinogenesis is observed in CA1 pyramidal hippocampal neurons. Spine numbers measured for control slices were 7 per 50 µm dendrite length vs. 11 spines per 50 µm dendrite length for both Nle1-AngIV and Dihexa treated neurons; Mean±S.E.M., n=17; **=P<0.01 Statistical significance by one-way ANOVA followed by Tukey Multiple Comparisons Test; Experiments were repeated at least three times.

To further assess the physiological significance of the spine induction witnessed in dissociated neonatal hippocampal neurons the effects of Dihexa and Nle1-AngIV on spine formation in organotypic hippocampal slice cultures was evaluated. These preparations, while still neonatal in origin, represent a more intact and three dimensional environment than dissociated neurons. Hippocampal CA1 neurons, which have been functionally linked to hippocampal plasticity and learning/memory, could be easily identified based on morphology and were singled out for analysis. Dihexa and Nle1-AngIV significantly augmented spinogenesis in organotypic hippocampal slice cultures when compared to vehicle treated neurons. There were no differences in spine numbers between the Dihexa and Nle1-AngIV treatment groups (FIGS. 7A and B). Spine numbers measured for control slices were 7 per 50 µm dendrite length vs. 11 spines per 50 µm dendrite length for both Nle1-AngIV and Dihexa treated neurons; mean±S.E.M., n=13-20; **=P<0.01.

Discussion

In this study, Dihexa like Nle1-AngIV was a potent cognitive enhancer when given either ICV or orally. As predicted, Dihexa and Nle1-AngIV both promoted spinogenesis and enhance synaptogenesis in cultured rat hippocampal neurons. As expected of an angiotensin IV analogue, Dihexa exerted spine induction effects at sub-nano-molar concentrations with some spine formation by Dihexa and Nle1-AngIV occurring as early as 30 minutes after stimulation (FIG. 3D). The maximal effect, however, requires a significantly longer treatment period (FIG. 3C).

Spine head size measurements were taken as an indicator of synaptic potentiation. Larger spines with a greater surface area tend to have larger synapses, a larger PSD to recruit scaffolding proteins, and a greater number of glutamatergic receptive neurotransmitter receptors (Kennedy 1997). Although not different from one another (P>0.05), both Dihexa and Nle1-AngIV treatment groups exhibited large expansions in spine head size. Changes in spine morphology and numbers are proposed to be mechanisms for converting short-term synaptic changes into highly stable and long-lasting changes (Hering and Sheng 2001).

To evaluate the functional significance of these spine changes Nle1-AngIV and Dihexa stimulated hippocampal neurons were immunostained against the glutamatergic presynaptic marker VGLUT1 (Balschun, Moechars et al. 2010), the general presynaptic marker Synapsin (Ferreira and Rapoport 2002) and the postsynaptic marker PSD-95 (Kennedy 1997; Han and Kim 2008) to decipher neurotransmitter phenotypes. The high and unaltered correlation between VGLUT1, Synapsin, and PSD-95 in both treated and control dendrites suggests that the newly minted spines support functional synapses (FIG. 5 and Table 4) (Han and Kim 2008; Yasumatsu, Matsuzaki et al. 2008). Further, a near perfect correlation between mRFP-β-actin labeled spines and the general presynaptic marker Synapsin and VLGUT1 staining, which identifies excitatory glutamatergic synapses suggests that most AngIV-dependent effects on hippocampal spines were restricted to excitatory synapses. These findings correspond nicely with the findings of De Bundel et al. in which no effect on the inhibitory neurotransmitter GABA by native angiotensin IV was observed (De Bundel, Demaegdt et al. 2010).

The increase in mEPSC frequency observed by Dihexa and Nle1-AngIV treated preparations further supports that new spines form functional synapses (2; Hering and Sheng 2001;). The consistent strengthening of neurotransmission initiated by Dihexa and Nle1-AngIV could not be attributed to intrinsic fluctuations of neurotransmitter release or metabolic and mechanical influences (Yasumatsu, Matsuzaki et al. 2008). The data presented here suggest that Nle1-AngIV and Dihexa increase miniature synaptic activity by increasing dendritic spine densities and altering the morphological phenotype of postsynaptic spines in-vitro and may represent the mechanism that underlies facilitated learning observed AngIV analogues.

Figure 7B:
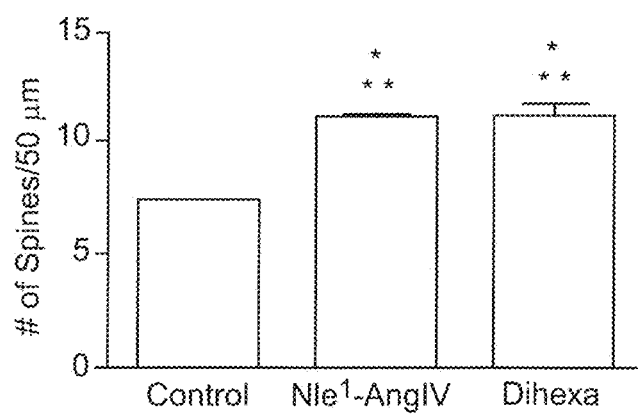

To bridge the adult behavioral data to the in vitro mechanistic theory, organotypic hippocampal slice cultures that maintain an environment representative of an intact hippocampus were employed and evaluated for treatment-induced spinogenesis. Application of $10^{-12}$ M Nle1-AngIV and Dihexa in ballistically transfected hippocampal slices significantly increase spine densities (FIG. 7) implying that such changes may in fact be occurring in the intact hippocampus.

Thus, Dihexa fits the criteria necessary for an effective anti-dementia drug: 1) it is orally active, as it survives passage through the gut and enters the brain; 2) it augments neuronal connectivity, a necessary property when faced with loss of neuronal connectivity; and 3) it is inexpensive to synthesize thus making it accessible to patients.

Example 2

The Target of AngIV Analogs is Hepatocyte Growth Factor

This Example shows that the novel angiotensin IV ligand Dihexa and its parent molecule Nle1-AngIV act through the HGF/c-Met receptor system.
Materials and Methods
Animals and Surgery Male Sprague-Dawley rats (Taconic derived) weighing 390-450 g were maintained with free access to water and food (Harland Tekland F6 rodent diet, Madison, Wis.) except the night prior to surgery when food was removed. Each animal was anesthetized with Ketamine hydrochloride plus Xylazine (100 and 2 mg/kg im. respectively; Phoenix Scientific; St. Joseph, Mo., and Moby; Shawnee, Kans.). An intracerebroventricular (icv) guide cannula (PE-60, Clay Adams; Parsippany, N.Y.) was stereotaxically positioned (Model 900, David Kopf Instruments; Tujunga, Calif.) in the right hemisphere using flat skull coordinates 1.0 mm posterior and 1.5 mm lateral to bregma (Wright et al., 1985). The guide cannula measured 2.5 cm in overall length and was prepared with a heat bulge placed 2.5 mm from its beveled tip, thus acting as a stop to control the depth of penetration. Once in position, the cannula was secured to the skull with two stainless-steel screws and dental cement. Post-operatively the animals were housed individually in an American Accreditation for Laboratory Animal Care-approved vivarium maintained at 22±1° C. on a 12-h alternating light/dark cycle initiated at 06:00 h. All animals were hand gentled for 5 min per day during the 5-6 days of post-surgical recovery.
Behavioral Testing The water maze consisted of a circular tank painted black (diameter: 1.6 m; height: 0.6 m), filled to a depth of 26 cm with 26-28° C. water. A black circular platform (diameter: 12 cm; height: 24 cm) was placed 30 cm from the wall and submerged 2 cm below the water surface. The maze was operationally sectioned into four equal quadrants designated NW, NE, SW, and SE. For each rat the location of the platform was randomly assigned to one of the quadrants and remained fixed throughout the duration of training. Entry points were at the quadrant corners (i.e. N, S, E, W) and were pseudo-randomly assigned such that each trial began at a different entry point than the preceding trial. Three of the four testing room walls were covered with extra-maze spatial cues consisting of different shapes (circles, squares, triangles) and colors. The swimming path of the animals was recorded using a computerized video tracking system (Chromotrack; San Diego Instruments, CA). The computer displayed total swim latency and swim distance. Swim speed was determined from these values.

Each member of the treatment groups received an icv injection of scopolamine hydrobromide (70 nmol in 2 μl aCSF over a duration of 20 s) 20 min prior to testing followed by Dihexa (300 pmol in 2 μl aCSF), Hinge (300 pmol in 2 μl aCSF), or Hinge+Dihexa (300 pmol in 4 μl aCSF) 5 min prior to testing. This scopolamine preparation is a generally accepted animal model of the spatial memory dysfunction that accompanies dementia (Fisher et al., 2003). Control groups received scopolamine or aCSF 20 min prior to testing followed by aCSF 5 min prior testing. The behavioral testing protocol has been described previously in detail (Wright et al., 1999). Briefly, acquisition trials were conducted on 8 consecutive days, 5 trials/day. On the first day of training the animal was placed on the pedestal for 30 s prior to the first trial. Trials commenced with the placement of the rat facing the wall of the maze at one of the assigned entry points. The rat was allowed a maximum of 120 s to locate the platform. Once the animal located the platform it was permitted a 30 s rest period on the platform.

If the rat did not find the platform, the experimenter placed the animal on the platform for the 30 s rest period. The next trial commenced immediately following the rest period. Upon completion of each daily set of trials the animal was towel-dried and placed under a 100 watt lamp for 10-15 min and then returned to its home cage.
Statistical Analyses One-way ANOVA was used to analyze the dendritic spine results and significant effects were analyzed by Tukey post-hoc test. Morris water maze data set mean latencies to find the platform during each daily block of five trials were calculated for each animal for each day of acquisition. One-way ANOVAs were used to compare group latencies on Days 1, 4, and 8 of training. Significant effects were analyzed by Newman-Keuls post-hoc test with a level of significance set at $P<0.05$.
Scattering Assay.

MDCK cells were grown to 100% confluency on the coverslips in six-well plates and washed twice with PBS. The confluent coverslips were then aseptically transferred to new six well plates containing 900 μl serum free DMEM. Norleual, Hinge peptide, and/or HGF (20 ng/ml) were added to appropriate wells. Control wells received PBS vehicle. Plates were incubated at 37° C. with 5% $CO_2$ for 48 hours. Media was removed and cells were fixed with methanol. Cells were stained with Diff-Quik Wright-Giemsa (Dade-Behring, Newark, Del.) and digital images were taken. Coverslips were removed with forceps and more digital images were captured. Pixel quantification of images was achieved using Image J and statistics were performed using Prism 5 and InStat v.3.05.
Dissociated Hippocampal Neuronal Cell Culture Preparation Hippocampal neurons ($2\times10^5$ cells per square centimeter) were cultured from P1-2 Sprague Dawley rats on plates coated with poly-L-lysine from Sigma (St. Louis, Mo.; molecular weight 300,000). Hippocampal neurons were maintained in Neurobasal A media from Invitrogen (Carlsbad, Calif.) supplemented with B27 from Invitrogen, 0.5 mM L-glutamine, and 5 mM cytosine-D-arabinofuranoside from Sigma added at 2 days in vitro. Hippocampal neurons were then cultured a further 3-7 days, at which time they were either transfected or treated with various pharmacological reagents as described in the text or figure legends.
Transfection of Dissociated Hippocampal Neuronal Cell Cultures Neurons were transfected with mRFP-β-actin on day in vitro 6 (DIVE) using LipofectAMINE™ 2000 (Invitrogen) according to the manufacturer's protocol. This protocol yielded the desired 3-5% transfection efficiency thus enabling the visualization of individual neurons. Higher efficiencies obscured the dendritic arbor of individual neurons. Expression of fluorescently tagged actin allowed clear visualization of dendritic spines, as dendritic spines are enriched in actin. On DIV7 the cells were treated with vehicle ($H_2O$) or peptides (as described in the text) added to media. On DIV 12 the neurons were fixed (4% paraformaldehyde, 3% sucrose, 60 mM PIPES, 25 mM HEPES, 5 mM EGTA, 1 mM $MgCl_2$, pH 7.4) for 20 min at room temperature and mounted. Slides were dried for at least 20 hours at 4° C. and fluorescent images were obtained with Slidebook 4.2 Digital Microscopy Software driving an Olympus IX81 inverted confocal microscope with a 60× oil immersion lens, NA 1.4 and resolution 0.280 μm Dendritic spine density was measured on primary and secondary dendrites at a distance of at least 150 μm from the soma. Five 50 μm long segments of dendrite from at least 10 neurons per data point were analyzed for each data point reported. Each experiment was repeated at least three times using independent culture preparations. Dendrite length was determined using the National institutes of Health's Image J 1.410 program (NIH, Bethesda, Md.) and the neurite tracing program Neuron J (Meijering, Jacob et al. 2004) Spines were manually counted.

Organotypic Hippocampal Slice Culture Preparation and Transfection

Hippocampi from P4 Sprague Dawley rats were cultured as previously described (Wayman, Impey et al. 2006). Briefly, 400 μm slices were cultured on (Milipore, Billerica, Mass.) for 3 days after which they were biolistically transfected with tomato fluorescent protein (TFP) using a Helios Gene Gun (BioRad, Hercules, Calif.), according to the manufacturer's protocol, to visualize dendritic arbors. Following a 24 hour recovery period slices were stimulated with 1 pM Nle1-AngIV or Dihexa for 2 days. Slices were fixed and mounted. Hippocampal CA1 neuronal processes were imaged and measured as described above.

Acute Hippocampal Slices

Adult Sprague-Dawley rats (250 g+) obtained from Harlan Laboratories (Ca, USA) were anesthetized with isofluorane (Vet One™, MWI, Meridian, Id., USA) and decapitated. The brain was rapidly removed and placed into ice-chilled artificial cerebrospinal fluid (aCSF) for approximately 30 s. Both hemispheres were separated by a mid-saggital cut and both hippocampi removed. Slices were sectioned cross- and length-wise (400 μm) to ensure penetrability of the drug, using a McIlwain tissue chopper (Brinkmann, Gomshall, UK) and transferred to a gassed (95% $O_2$/5% $CO_2$) incubation chamber containing aCSF for 90 minutes at room temperature. Slices were transferred to fresh tubes, aCSF was removed by careful suctioning and replaced with aCSF containing vehicle (aCSF+aCSF), 100 ng/ml with carrier free adult recombinant Hepatocyte Growth Factor (HGF) (R and D Systems, MN, USA) in aCSF, $10^{-10}$ M Hinge (Harding lab), 50 ng/ml in aCSF, $10^{-10}$ M Dihexa (Harding lab) in aCSF, $10^{-12}$ M Dihexa in aCSF or 50 ng/ml HGF+$10^{-12}$ M Dihexa in aCSF for 30 minutes at 37° C. with gentle rocking. aCSF was removed and the slices were lysed using RIPA buffer (Upstate/Milipore, Billerica, Mass.) and inhibitor Cocktails I and II (Sigma, St. Louis, Mo.), sonicated on ice and clarified by centrifugation for 30 minutes, 13,000 rpm at 4° C. The supernatant was removed from the pellet and stored at −80° C. or processed immediately for gel electrophoresis.

shRNA

A target sequence for c-Met was designed using RNAi central design program (see the website located at can.cshl.edu/). The target sequence GTGTCAGGAGGTGTTTGGAAAG (SEQ ID NO: 2) was inserted into pSUPER vector (Oligoengine, Seattle Wash.) which drives endogenous production of shRNA under the H1 promoter. The shRNA was transfected into cells using the lipofectamine method described above. Verification of receptor knockdown was done by creating a c-Met-6-Myc tagged gene product using the Gateway cloning system (Invitrogen). The Met protein coding sequence was cloned from rat whole brain cDNA using primers obtained from Integrated DNA Technologies, Inc. The amplified product was gel purified and a band corresponding to 190 kDa band excised and cloned into a PCAGGS-6-Myc destination vector (Gateway).

Gel Electrophoresis and Western Blotting

Protein concentration of the samples was quantified using the BCA method (Pierce, Rockford, Ill.) following the manufacturers protocol. Samples were added to SDS-PAGE buffer and boiled for 10 min. before loading onto a 4-12% Bis-Tris pre-cast gel (Invitrogen, Carlsbad, Calif.) for electrophoresis. Proteins were transferred onto PVDF membranes (Bio Rad, Hercules, Calif.) and blocked with AquaBlock™ (New England Biolabs, Ipswich, Mass.) for 1 hour at room temperature (RT). Primary antibody incubation was done in AquaBlock™ with rabbit anti-Met and anti-rabbit phospho-Met (Tyr1234/1235) (1:1000, Cell Signaling Technology, Danvers, Mass.) overnight at 4° C. Alternating washes were done with PBS and PBST. Secondary antibody (IRDye) (Rockland, Gilbertsville, Pa.) incubations were done in AquaBlock™ for one hour at RT. Blots were imaged using LI-COR Odyssey Infrared Imaging System (LI-COR Biosciences, Lincoln, Nebr.).

Immunocytochemistry

Transfected neurons were treated, fixed and stained as previously described in Chapter two. Briefly, cells were permeablized with 0.1% Triton X-100 detergent (Bio-Rad; Hercules, Calif.) for 10 minutes. An 8% bovine serum albumin (Intergen Company; Burlington, Mass.) in PBS was used to prevent non-specific binding for one hour at R.T.; Primary antibody incubations were at a 1:2500 dilution (see below) in 1% BSA in PBS at 4° C. overnight. Secondary antibody, 1:3000 Alexafluor 488 goat-anti-mouse (Invitrogen: Carlsbad, Calif.) was applied for two hours at room temperature. Coverslips were mounted with ProLong Gold anti-fade reagent (Invitrogen; Carlsbad, Calif.) and all washes were done with PBS. Imaging and analysis were performed as described above. For presynaptic excitatory transmission the VGLUT1 (Synaptic Systems, Goettingen, Germany) marker (Balschun, Moechars et al.) was employed and for general presynaptic transmission synapsin1 (Synaptic Systems, Goettingen, Germany) (Ferreira and Rapoport 2002) was applied. A postsynaptic function was established by PSD-95 (Milipore, Billerica, Mass.) (El-Husseini, Schnell et al. 2000). In each instance the total number of spines was counted for the treatment groups, control, Nle1-AngIV and Dihexa, to ensure an active phenotype. The total number of actin enriched spines (red) adjacent to VGLUT1 or Synapsin were counted and converted to a percentage as the percent correlation of treatment-induced spines to presynaptic markers is a strong indicator of ability to transmit excitatory signals. In our application the number of correlations consisted of red fluorescent-tagged actin spines against green PSD-95 immuno-positive puncta which, when merged, resulted in an orange spine.

Whole-Cell Recordings

Patch-clamp experiments were performed on mRFP-β-actin transfected cultured hippocampal neurons (vehicle control) and on transfected hippocampal neurons with 1 pM Hinge or Dihexa, or 10 ng/ml HGF (R&D Systems) 5 day pretreatment. Recordings were taken from neurons that were pyramidal-like in shape (~20 μm cell bodies and asymmetric dendrite distribution). The time after transfection was 6 days. The culture medium was exchanged by an extracellular solution containing (in mM) 140 NaCl, 2.5 KCl, 1 MgCl$_2$, 3 CaCl$_2$, 25 glucose, and 5 HEPES; pH was adjusted to 7.3 with KOH; osmolality was adjusted to 310 mOsm. Cultures were allowed to equilibrate in a recording chamber mounted on inverted microscope (IX-71; Olympus optical, Tokyo) for 30 min before recording. Transfected cells were visualized with fluorescence (Olympus optical). Recording pipettes were pulled (P-97 Flaming/Brown micropipette puller; Sutter Instrument, Novato, Calif.) from standard-wall borosilicate glass without filament (OD=1.5 mm; Sutter Instrument). The pipette-to-bath DC resistance of patch electrodes ranged from 4.0 to 5.2MΩ, and were filled with a internal solution of the following composition (in mM): 25 CsCl, 100 CsCH$_3$O$_3$S, 10 phosphocreatine, 0.4 EGTA, 10 HEPES, 2 MgCl$_2$, 0.4 Mg-ATP, and 0.04 Na-GTP; pH was adjusted to 7.2 with CsOH; osmolality was adjusted to 296-300 mOsm. Miniature EPSCs (mEPSCs) were isolated pharmacologically by blocking GABA receptor chloride channels with picrotoxin (100 µM; Sigma), blocking glycine receptors with strychnine (1 µM; Sigma), and blocking action potential generation with tetrodotoxin (TTX, 500 nM; Tocris). Recordings were obtained using a Multiclamp 700B amplifier (Molecular Devices, Sunnyvale, Calif.). Analog signals were low-pass Bessel filtered at 2 kHz, digitized at 10 kHz through a Digidata 1440A interface (Molecular Devices), and stored in a computer using Clampex 10.2 software (Molecular Devices). The membrane potential was held at −70 mV at room temperature (25° C.) during a period of 0.5-2 h after removal of the culture from the incubator. Liquid junction potentials were not corrected. Data analysis was performed using Clampfit 10.2 software (Molecular Devices), and Mini-Analysis 6.0 software (Synaptosoft Inc.; Fort Lee, N.J.). The criteria for successful recording included the electrical resistance of the seal between the outside surface of the recording pipette and the attached cell >2 GΩ, neuron input resistance >240 MΩ. The mEPSCs had a 5-min recording time.

Results

Hepatocyte Growth Factor Augments the Dendritic Architecture and Supports Synaptogenesis Dihexa and Nle1-AngIV have previously been shown to induce spinogenesis in mRFP-β-actin transfected hippocampal neurons (see Example 1); however the mechanism underlying this action was unknown. Because of the ability of Norleual, another AngIV analogue to block the action of HGF on c-Met we hypothesized that increases in spine density initiated by Dihexa and Nle1-AngIV are mediated by the HGF/c-Met system. As such, the effects of HGF on spinogenesis in dissociated hippocampal cultures were evaluated. Hippocampal neurons were transfected with mRFP-β-actin on day in vitro (DIV) 6 and stimulated with HGF for 5 days.

Figure 8:
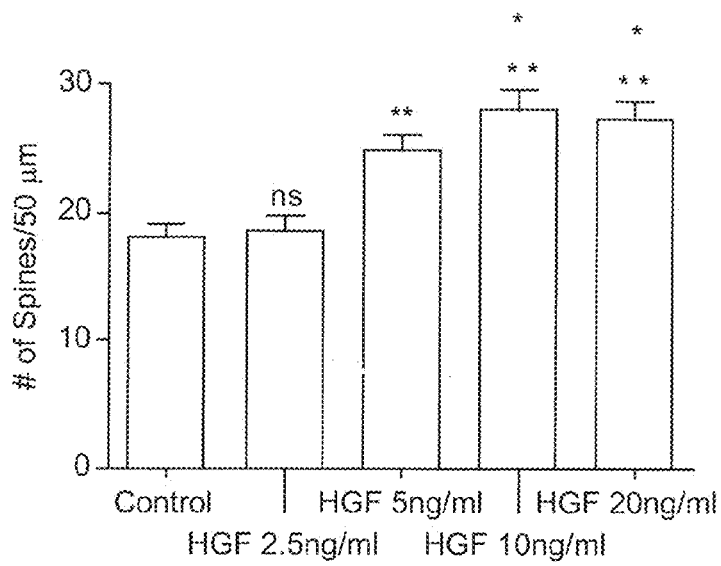
FIG. 8. HGF dose-dependently enhances spinogenesis. Effect of HGF on spinogenesis in dissociated hippocampal neurons. Dissociated hippocampal neurons from 1 or 2 day old rats were transfected with mRFP-β-actin and stimulated with HGF for 5 days. Treatment with 2.5 ng/ml HGF did not affect basal spine numbers and was considered sub-threshold. Doses of 5, 10 and 20 ng/ml significantly increased the number of spines per 50 µm dendrite lengths compared to vehicle control treated neurons. *** P<0.001; mean±S.E.M.; n=50 per treatment group.

A dose-dependent increase in spine numbers following HGF stimulation was observed with the lowest effective dose being 5 ng/ml dose (mean spine numbers=24.7; =p<0.01 vs. control; ns vs HGF 10 and 20 ng/ml). The most significant effects were produced by 10 and 20 ng/ml doses (mean spine numbers=27.5 and 27.0 respectively; n=50 per treatment group; *=p<0.001; df=4/245; F=13.5). A 2.5 ng/ml dose of HGF, however, had no effect on basal spine numbers (mean spine numbers=18.6 vs. control=18.0) (FIG. 8) and was therefore considered to be sub-threshold.

Figure 9A:
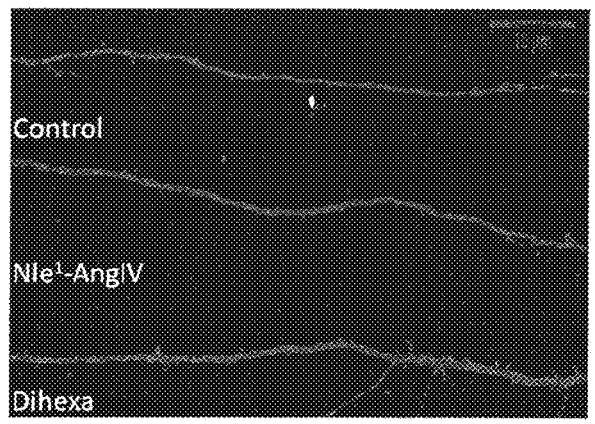
FIGS. 9A and B. Effects of Dihexa and HGF on spinogenesis in organotypic hippocampal slice cultures. Hippocampal slice cultures were biolistically transfected with the red soluble protein Tomato on DIV3 and stimulated with Dihexa or HGF on DIV5. Organotypic hippocampal slice cultures maintain a more intact perforant path and therefore represent a more intact environment. A) Representative images of CA1 neurons, the neuronal type in the hippocampus that exhibits learning associated synaptic plasticity. Hippocampal slices were stimulated with vehicle, $10^{-12}$ M Dihexa, or 10 ng/ml HGF for 2 days. B) Bar graph representing the number of spines per 50 µm dendrite length for each treatment group. Dihexa and HGF significantly increase the number of spines on CA1 hippocampal neurons compared to control treated neurons. ***=P<0.001; mean±S.E.M.; n=20 for control, 26 for Dihexa and 38 for HGF stimulated neurons.
Figure 9B:
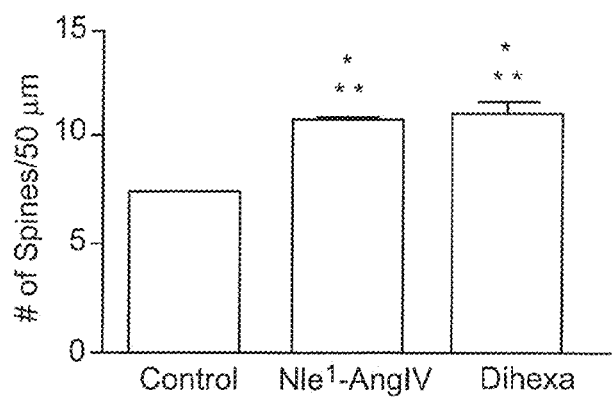

To evaluate the ability of HGF to augment spinogenesis in a more physiologically relevant environment, organotypic hippocampal slices were employed. Hippocampal slices which were biolistically transfected with the soluble red fluorescent protein Tomato were stimulated with 10 ng/ml HGF, $10^{-12}$ M Dihexa or vehicle for 48 hours. CA1 hippocampal neurons, which are known to undergo plastic changes in response to learning were easily singled out for analysis based on morphology. Dihexa and HGF significantly increased the number of spines per 50 µm dendrite length in the CA1 hippocampal neurons (mean spine numbers=15.0 and 18.5 respectively compared to mean control spine numbers=6.1; *=P<0.001 and =P<0.01 between treatment groups; df=2/81; F=41.5) (FIGS. 9A and B).

Figure 10A:
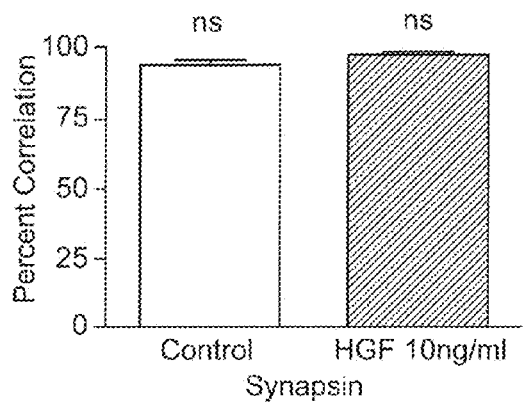
FIG. 10A-D. Effect of HGF treatment on synaptogenesis in dissociated hippocampal neurons. HGF treatment supports the formation of functional synapses as indicated by a high correlation between postsynaptic spines and markers of presynaptic active zones. A) Representative images of hippocampal neurons transfected with mRFP-β-actin on DIV6 and treated with 10 ng/ml of HGF or vehicle for 5 days in vitro. The neurons were stained for the general presynaptic marker Synapsin and glutamatergic presynaptic marker VGLUT1. B) Bar graph representing an active phenotype as indicated by a significant increase in the number of spines per 50 µm dendrite length following stimulation with HGF (10 ng/ml). Mean number of spines=33 vs. control= 23; ***=P<0.001 by one-way ANOVA and Tukey Multiple Comparisons Test; mean±S.E.M.; n=25). C) Percent correlation of actin-enriched postsynaptic spines (red) juxtaposed to the universal presynaptic marker Synapsin. A high percent correlation suggests functional synapses are formed. D) Percent correlation of actin-enriched spines juxtaposed to the glutamatergic presynaptic marker VGLUT1. A greater than 95% correlation suggests many of these inputs are glutamatergic.
Figure 10B:
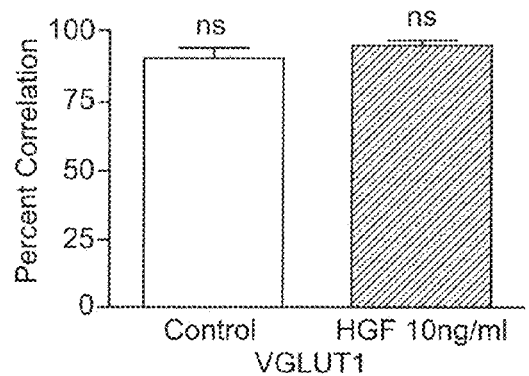
Figure 10C:
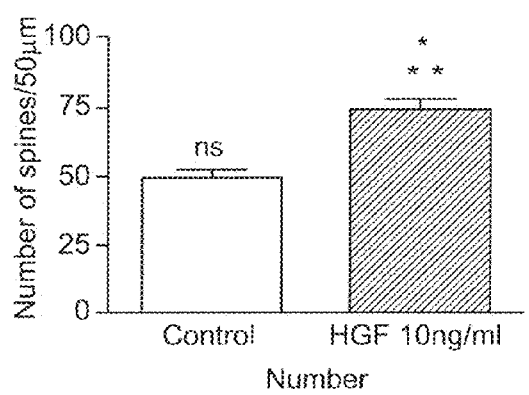
Figure 10D:
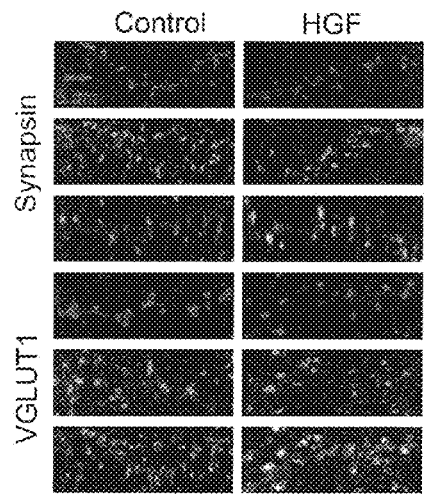

Previous studies in which neurons were treated with Dihexa and Nle1-AngIV indicated that most of dendritic spines that were induced co-localized with both pre- and postsynaptic markers indicated that these new spines supported functional synapses. In addition, the majority of synaptic input appeared to be glutamatergic. Because Dihexa, Nle1-AngIV, and HGF are proposed to all act through a common mechanism, the functional properties of HGF-induced spines was evaluated. mRFP-β-actin transfected hippocampal neurons were immunostained for a general marker of presynaptic active zones, synapsin (Ferreira and Rapoport; 2002) as well as a marker specific to glutamatergic synapses, Vesicular Glutamate Transporter 1 (VGLUT1) (Balschun, Moechars et al. 2010). HGF stimulation significantly augmented the number of postsynaptic spines (mean number of spines per 50 µm dendrite length for HGF=33 vs. 23 for control; ***=P<0.001; ±S.E.M. by one-way ANOVA) thus ensuring an active phenotype by HGF-treatment (FIGS. 10A and B). The number of postsynaptic spines adjacent to VGLUT1, or synapsin-positive puncta were counted and converted to a percentage of the total spines counted. For HGF-treated neurons (10 ng/ml) immunostained against Synapsin1 a 98% correlation between the presynaptic marker and postsynaptic actin-enriched spine was observed (FIG. 9C). A 95% correlation for VGLUT1 and postsynaptic spines indicated that spines induced by HGF were almost exclusively glutamatergic (FIG. 10D). The correlation between green puncta and red spines for vehicle treated neurons was similarly 94% for Synapsin and VGLUT1 (FIGS. 10C and D).

The above data suggest that spines produced in response to HGF-treatment form functional synapses. Furthermore, the high correlation with VGLUT1 suggests that many of these inputs are excitatory in nature. To further evaluate this conclusion, we measured the frequency of spontaneous AMPA-mediated mini-excitatory postsynaptic currents (mEPSCs) from neurons following HGF treatment and compared these data to those obtained for Dihexa, which had previously established to increase mEPSC frequency. Recordings were done on dissociated hippocampal neurons transfected with mRFP-β-actin and treated with $10^{-12}$ M Dihexa, 10 ng/ml HGF or an equivalent volume of vehicle for 5 days.

Figure 11:
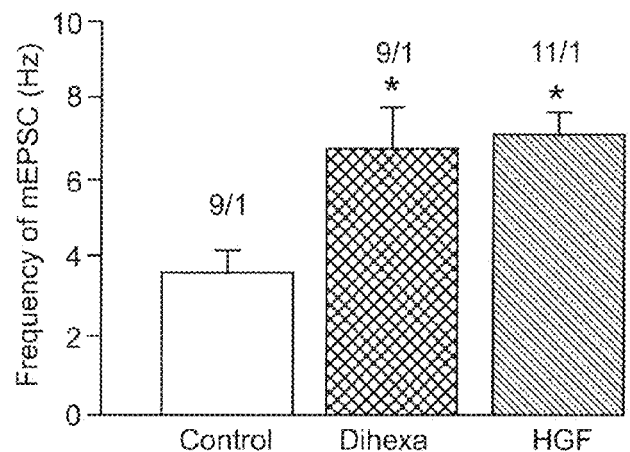
FIG. 11. Effect of Dihexa and HGF treatment on the frequency of mEPSCs in dissociated hippocampal neurons. Dissociated hippocampal neurons transfected with mRFP-β-actin were stimulated with $10^{-12}$ M Dihexa or 10 ng/ml for 5 days prior to recording mEPSCs. Neurons were treated with tetrodotoxin, picrotoxin, and strychnine to suppress action potential, GABA-dependent inhibition, and glycine-dependent inhibition. Treatment with both agonists significantly enhanced AMPA-mediated currents compared to vehicle treated neurons (** $P<0.002$; ±S.E.M. by one-way ANOVA followed by Newman-Keuls post hoc test; n=9, 9 and 11 respectively).

Both HGF (mean frequency=7.09±0.53; n=11) and Dihexa treatment (mean frequency=6.75±0.99; n=9) increased excitatory synaptic transmission nearly two-fold over control (mean frequency=3.55±0.60; n=9; **=P<0.002; mean±S.E.M. by one-way ANOVA followed by Newman-Keuls post hoc test) treated neurons (FIG. 11), confirming the supposition that HGF treatment supports increased synaptogenesis.

In order to ascertain whether angiotensin IV ligand actions are mediated by HGF/c-Met a synergy experiment was performed. Sub-threshold doses of HGF augmented with sub-threshold doses of Dihexa or Nle1-AngIV were previously shown to promote spinogenesis, suggesting a common mechanism of action. Dissociated hippocampal neurons transfected with mRFP-β-actin were stimulated for 5 days with sub-threshold concentrations of HGF and Dihexa (2.5 ng/ml+$10^{-13}$ M, respectively), biologically active doses of HGF (10 ng/ml), Dihexa or Nle1-AngIV ($10^{-12}$ M) or a combination of sub-threshold doses of 2.5 ng/ml HGF+$10^{-12}$ M Dihexa or 2.5 ng/ml HGF+$10^{-12}$ M Nle1-AngIV. The results are presented in FIGS. 12 A and B. Sub-threshold concentrations of HGF (2.5 ng/ml), Dihexa and Nle1-AngIV ($10^{-13}$ M) had no effect on basal spinogenesis and did not differ from control treated neurons (mean±S.E.M. spine numbers for control=17.4, HGF=16.5, Dihexa=17.1 and Nle1-AngIV=16.5 per 50 µm dendrite length; p>0.05). Biologically active doses of HGF (10 ng/ml), Dihexa and Nle1-AngIV ($10^{-12}$ M) produced a significant effect over control treated spines (mean±S.E.M. spine numbers for HGF=29.3, Dihexa=26.4 and Nle1-AngIV=29.8 per 50 µm dendrite). Combined sub-threshold doses of 2.5 ng/ml+$10^{-13}$ M Dihexa and 2.5 ng/ml+$10^{-13}$ M Nle1-AngIV phenocopied the effects of each agonist at its biologically active dose alone (mean±S.E.M. spine numbers for HGF+Dihexa are 28.8 and HGF+Nle1-AngIV are 26.2 per 50 µm dendrite length compared to control treated neurons=17.4; ***=p<0.001; mean±S.E.M.; by one-way ANOVA followed by Tukey post hoc test).

Figure 12A:
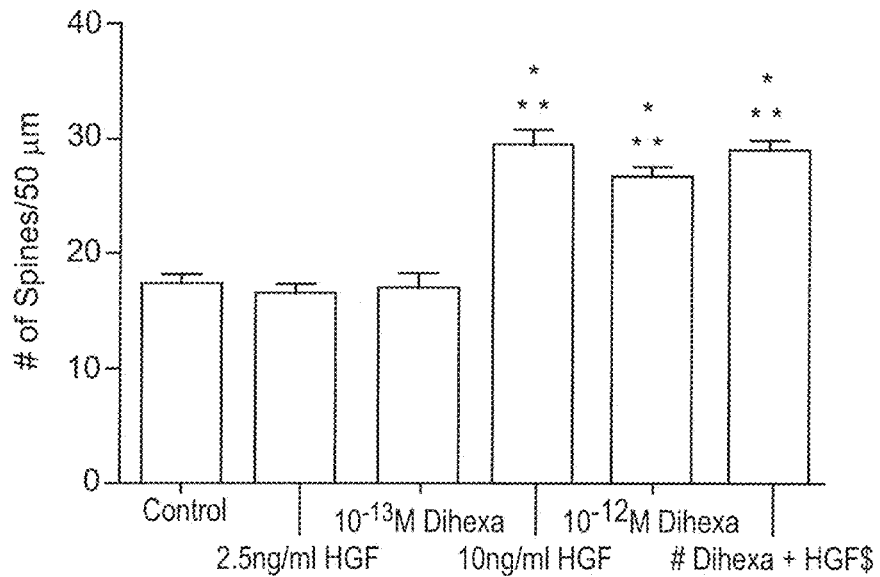
FIGS. 12A and B. Effect of maximal and sub-threshold doses of Angiotensin IV analogues and HGF on spinogenesis. A) Sub-threshold levels of HGF, Dihexa or Nle1-AngIV do not affect basal spine numbers. Combined sub-threshold levels of Dihexa ($10^{-13}$ M) and HGF (2.5 ng/ml) phenocopy the effects of Dihexa at its biologically effective dose alone; #=$10^{-13}$ M and $=2.5 ng/ml. B) A sub-threshold dose of the parent compound Nle1-Ang IV ($10^{-13}$ M) also does not affect basal spine levels. Combined sub-threshold levels of Dihexa ($10^{-13}$ M) and HGF (2.5 ng/ml) phenocopy the effects of Nle1-AngIV at its biologically effective dose alone; #=$10^{-13}$ M and $=2.5 ng/ml. The ability of combined agonists at sub-threshold doses to generate maximal responses suggests a commonality of receptor pathways. *** $P<0.001$; mean±S.E.M.; n=50.
Figure 13A:
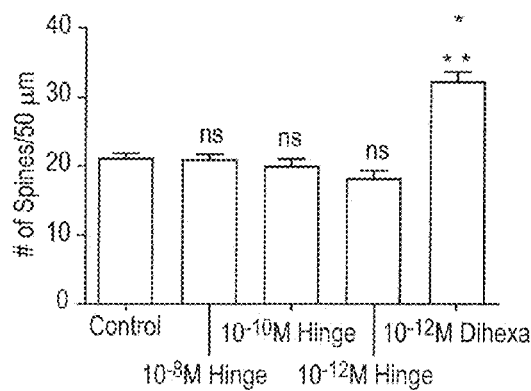
FIG. 13A-D. The effect of the novel HGF antagonist Hinge on angiotensin IV ligand- and HGF-mediated spinogenesis. A) The effects of the HGF antagonist Hinge ($10^{-12}$ M) on spinogenesis were evaluated. Hinge does not affect spinogenesis in neurons over a wide range of doses; Dihexa was included to ensure the neurons were responsive to treatment. B) Hinge inhibits HGF-induced spinogenesis C) Hinge inhibits Nle1-AngIV-induced spinogenesis D) Hinge inhibits Dihexa-induced spinogenesis. #=$10^{-12}$ M and $=10 ng/ml. The above data further indicate that the actions of Nle1-AngIV and Dihexa are mediated by the HGF/c-Met system. *** $P<0.001$; mean±S.E.M.; n=50.
Figure 13B:
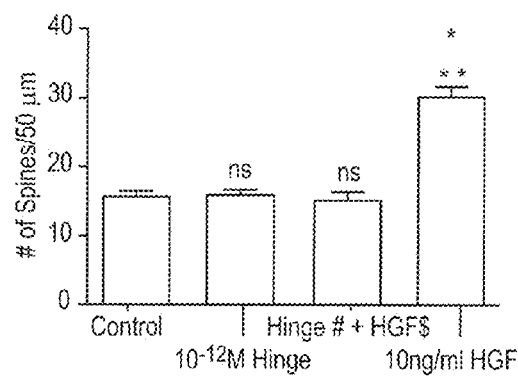
Figure 13C:
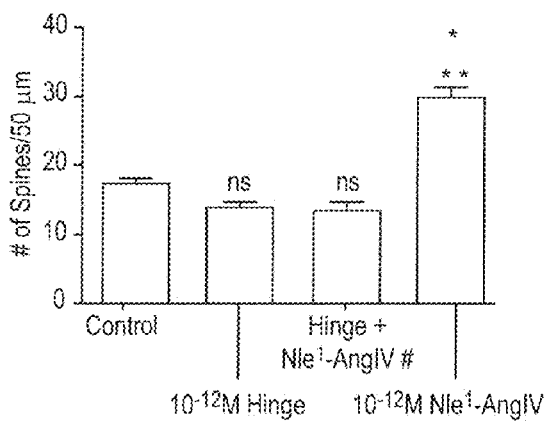
Figure 13D:
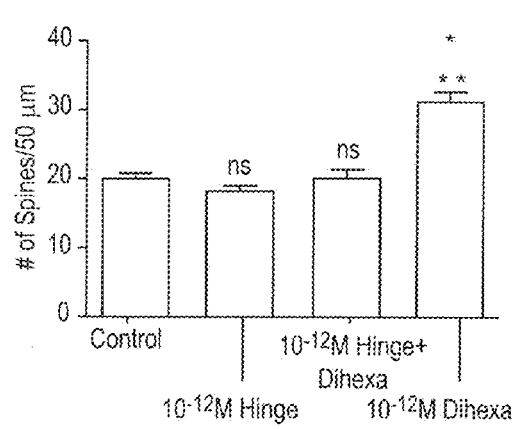

Seeking further substantiation for angiotensin IV ligand and HGF/c-Met mediated interactions, the novel HGF antagonist Hinge (DYIRNC, SEQ ID NO: 3) was utilized (Kawas et al., 20113 Hinge was confirmed as an HGF/c-Met receptor antagonist by its ability to inhibit scattering of Madin-Darby canine kidney (MDCK) cells, the gold standard for assessment of c-Met mediated activity. Cell scattering involves a loss of cell adhesion properties, cell migration and differentiation, the hallmarks of HGF and c-Met actions. Hinge was tested for its effects on dissociated hippocampal neurons and was found to have no effect on spinogenesis over a wide range of doses, thus indicating that Hinge and the HGF/c-Met system do not have a significant role in the basal spinogenesis seen in the cultured neurons (FIG. 13A). However, Hinge did effectively inhibit spine formation in neurons stimulated with 10 ng/ml HGF (FIG. 13B), $10^{-12}$ M Nle1-AngIV (FIG. 13C) or $10^{-12}$M Dihexa (FIG. 12D) further supporting the contention that these actions are mediated by the HGF/c-Met system.

Figure 14B:
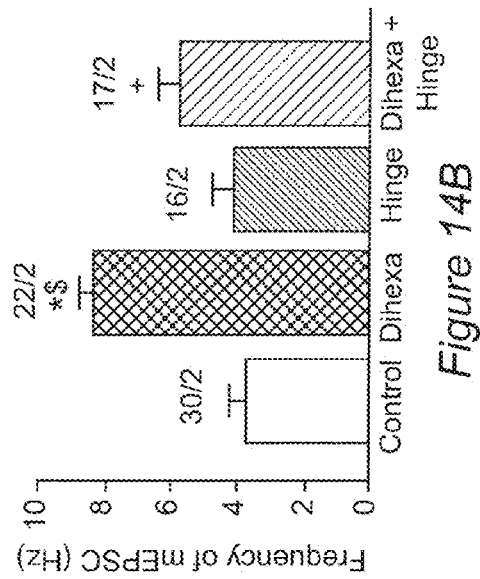
FIG. 14A-D. Effect of the HGF antagonist Hinge on HGF— and Dihexa-mediated enhancement of mEPSCs in dissociated hippocampal neurons. Dissociated hippocampal neurons were treated with Hinge ($10^{-12}$ M), HGF, Dihexa ($10^{-12}$ M) or HGF (10 ng/ml) for 5 days after at which time mEPSCs were recorded in the absence of action potentials. A) Representative traces of a Hinge treated neuron. B) Representative trace of a vehicle treated neuron. C) HGF significantly augments AMPA-mediated frequencies compared to control treated neurons. This effect is attenuated by Hinge while alone Hinge has no effect. D) Spontaneous AMPA-mediated frequencies are significantly increased following treatment with Dihexa and significantly reduced following pre-treatment with Hinge, which alone has no effect on baseline frequencies. * $P<0.001$; mean±S.E.M. by one way ANOVA followed by Newman-Keuls post hoc test.
Figure 14A:
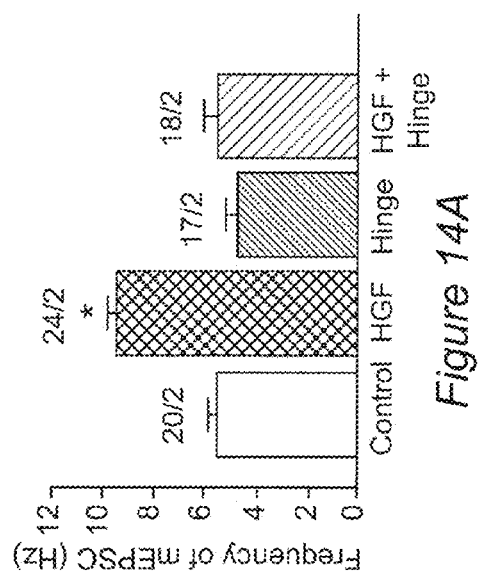
Figure 14D:
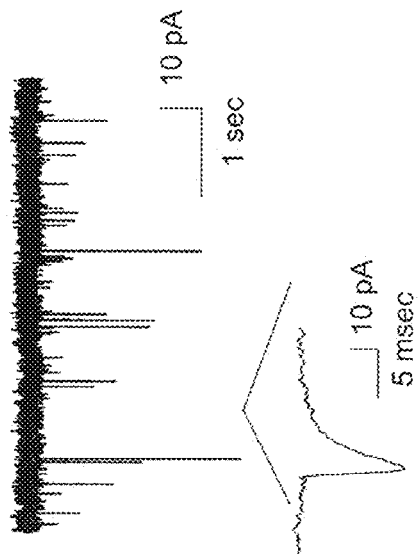
Figure 14C:
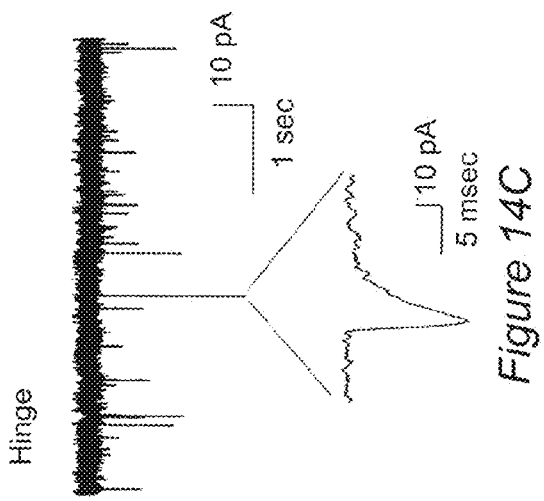

To assess the effects of Hinge on excitatory synaptic transmission mEPSCs were recorded form mRFP-β-actin transfected hippocampal neurons treated for 5 days with Hinge ($10^{-12}$ M), HGF (10 ng/ml), Dihexa ($10^{-12}$M), Hinge+HGF ($10^{-12}$M+10 ng/ml, respectively) or Hinge+Dihexa ($10^{-12}$ M each). Hinge alone does not affect synaptic transmission (mean frequency=4.51±0.47) compared to vehicle treated neurons (mean frequency=5.31±0.35; FIGS. 14A and B). HGF and Dihexa frequencies were significantly increased compared to both Hinge and vehicle treated neurons (mean frequency for HGF=9.66±0.20 and for Dihexa=8.25±0.56). However these effects are significantly attenuated by stimulation in the presence of Hinge (mean frequencies for HGF+Hinge=5.25±0.27 and Dihexa+Hinge=5.57±0.65; FIGS. 14A and B). These results suggest that the newly generated spines are forming functional synapses and while Hinge has no effect on synaptic transmission, it is its ability to inhibit spinogenesis that attenuates the AMPA-mediated frequencies.

Figure 15:
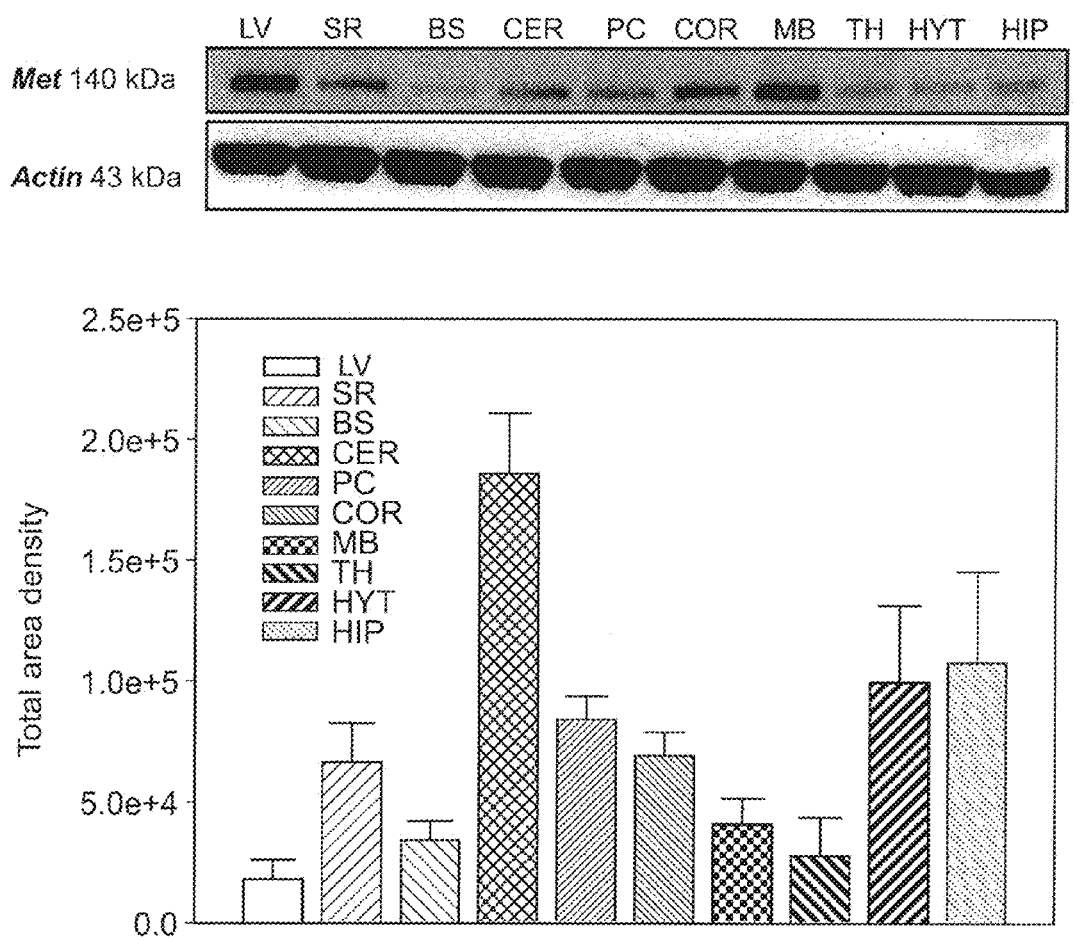
FIG. 15A-B. Distribution of c-Met protein in the adult rat brain. Gross brain regions were obtained from adult Sprague-Dawley rats and acutely frozen in liquid nitrogen. The samples were homogenized, separated by electrophoresis and immunoblotted for c-Met protein and actin. A) A representative Western blot of the samples probed against c-Met protein (bands are at 145 kDa) and actin serving as a loading control. Equal amounts of protein were loaded in each lane based on BCA protein determinations. B) The bar graph represents the amount of c-Met (unspecified units) in distinct brain regions of importance to cognition. The brain samples were compared to liver where HGF is produced.

The proposed angiotensin IV receptor HGF is the ligand for the tyrosine kinase receptor c-Met. Although the localization of c-Met and HGF mRNA in the brain has been well documented (Jung, Castren et al. 1994; Honda, Kagoshima et al. 1995; Thewke and Seeds 1996; Achim, Katyal et al. 1997) the presence and distribution of c-Met protein has not been examined. Therefore we probed several brain regions for the presence of c-Met but were unable to do so for HGF due to a lack of effective antibodies. High levels of c-Met protein were observed throughout most of the brain regions. Specifically, the highest signal of c-Met protein was seen in the hippocampus and appears to be greater than in the liver which is a major site of HGF production. A strong signal was also observed in the prefrontal cortex and midbrain, regions of importance to cognition, while neocortex had a somewhat attenuated signal the cerebellum produced the lowest signal (FIGS. 15 A and B).

Figure 16:
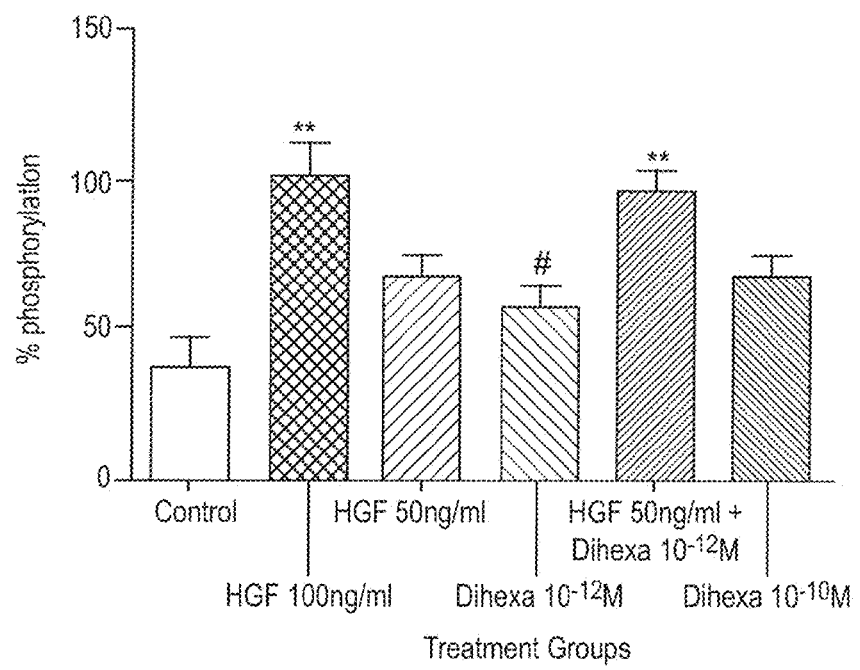
FIG. 16. Stimulation of c-Met phosphorylation by HGF and Dihexa in rat hippocampal slices. To test whether Dihexa could activate the c-Met receptor in the adult rat brain, hippocampal slices were acutely stimulated for 30 minutes with HGF, Dihexa or vehicle (aCSF). Receptor activation was measured by phosphorylation of the c-Met receptor by Western blot. Saturating doses of HGF (100 ng/ml) and Dihexa ($10^{-10}$ M) effectively augment c-Met phosphorylation in acutely stimulated adult hippocampal slices compared to vehicle treated slices. Sub-threshold doses of HGF (50 ng/ml) and Dihexa ($10^{-12}$ M) did not significantly increase c-Met receptor phosphorylation compared to control. However, combined sub-threshold doses of HGF and Dihexa phenocopied the saturating doses of HGF and Dihexa.
Figure 16:
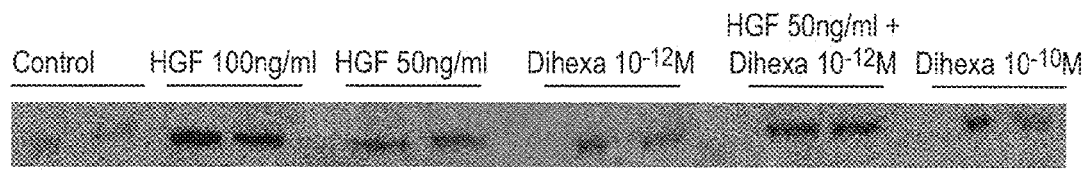
Figure 17:
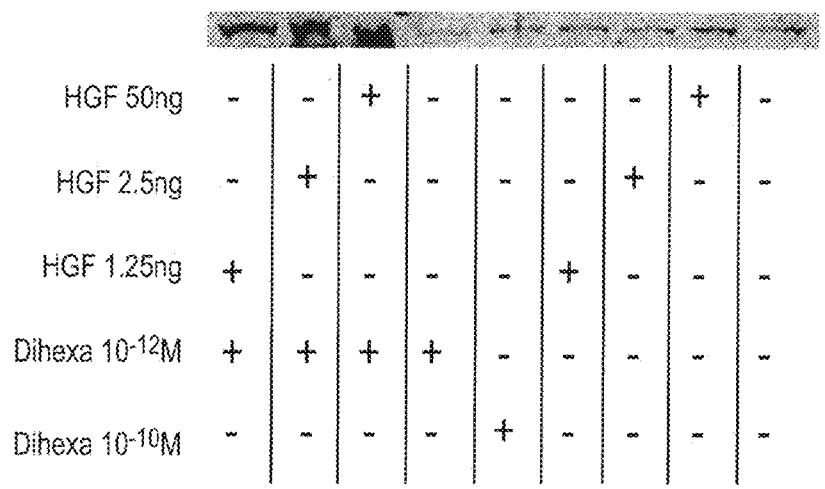
FIG. 17. Effect of the HGF mimetic, Dihexa, on c-Met activation. HEK 293 cells were treated with HGF+/−Dihexa at various doses, incubated at 37° C. for 30 minutes, and then analyzed for phosphorylated (activated) c-Met by immunoblotting. The results clearly demonstrate the ability of HGF and Dihexa to work synergistically to activate c-Met.
Figure 18:
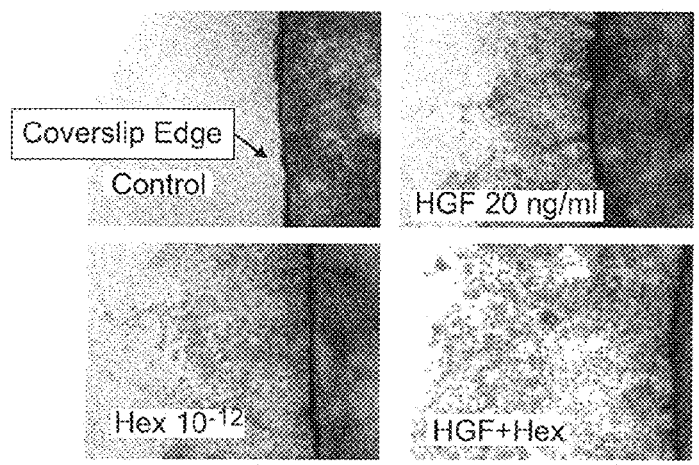
FIG. 18. Effect of the HGF mimetic, Dihexa, HGF-dependent cell scattering. Cell scattering was assessed in MDCK cells. Cells were grown to confluence on coverslips, which were then transferred to a clean plate. After treatment for four days, the number of cells that had scattered off the coverslip was quantitated. HEX=Dihexa at $10^{-10}$ M.

The apparent dependency of the actions of Dihexa on the HGF/c-Met system predicted that Dihexa in the presence of sub-threshold levels of HGF should be able to stimulate c-Met phosphorylation and activation. Therefore acute adult rat hippocampal slices were stimulated with HGF, Dihexa at saturating and non-saturating concentrations alone and in combination and probed for phospho-Met. Phosphorylation of the c-Met receptor indicates receptor activation. FIG. 16 shows phosphorylation of the c-Met receptor following a 30 minute treatment with vehicle and various concentrations HGF or Dihexa. Saturating doses of HGF (100 ng/ml) and Dihexa ($10^{-10}$ M) Dihexa both increased c-Met phosphorylation compared to control (aCSF) treated slices; (p<0.007). Non-saturating doses of HGF (50 ng/ml) and Dihexa ($10^{-12}$ M) were not statistically different from control treated slices (p>0.05) and therefore considered to be sub-threshold. The sub-threshold doses of HGF and Dihexa combined, however, appeared to produce an effect similar to the saturating doses of HGF and Dihexa (p<0.007). Thus dependent on the dose it appears that Dihexa is independently capable of activating the HGF/c-Met system in the adult rat brain alone as well as in conjunction with HGF. In concert with these findings Dihexa able to dramatically augment the ability of HGF to activate c-Met by phosphorylation in HEK293 cells (FIG. 17) and stimulate MDCK cell scattering (FIG. 18).

Figure 19:
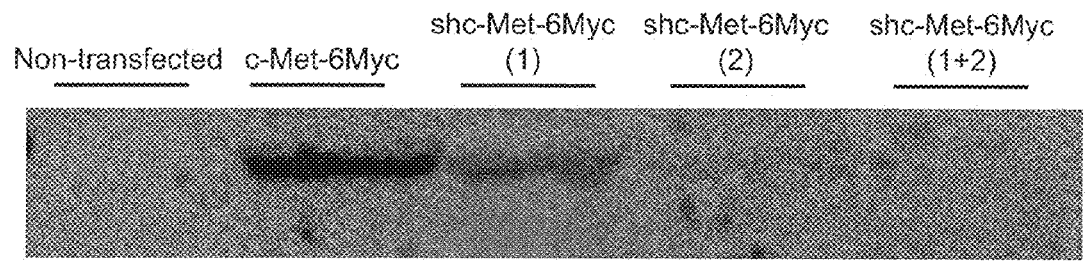
FIG. 19. Verification of c-Met receptor knockdown. Receptor knockdown was confirmed by transfecting HEK cells with mRFP-β-actin (untransfected), a 6Myc-tagged cMet gene product that served to verify presence of protein, shRNA (c-Met) sequences (only sh1 was employed for the knockdown experiment) and both shRNA's combined. The transfected cells were cultured for a further 24 hours then lysed with RIPA buffer and prepared for gel electrophoresis. The samples were probed against Myc by Western blot. Untransfected cells serving as the negative control showed no signal, the 6-Myc-tagged cMet gene product was the positive control and had a strong signal. Both the shMet1 and shMet2 sequences considerably attenuated the signal and combined did not have a signal indicating effective knock down of the receptor.

To irrefutably confirm that the AngIV analogues act via the HGF/c-met system an shRNA for c-Met was employed to knock-down the receptor. Dissociated hippocampal neurons were transfected with mRFP-β-actin and shMet RNA and receptor knock-down was allowed to take place for 48 hours prior to stimulating with 0.5 µg (per well) HGF (10 ng/ml), Dihexa or Nle1-AngIV (both at $10^{-12}$ M). Longer exposure appeared to be detrimental or toxic to the neurons. Effective c-Met receptor knock-down was verified by transfecting human embryonic kidney (HEK) cells with (0.1 µg) 6-Myc-tagged c-Met, (0.1 µg) shMet or mRFP-β-actin alone. Successful knockdown was continued by immunoblotting for Myc tagged c-met using an anti-Myc antibody (FIG. 19).

Figure 20:
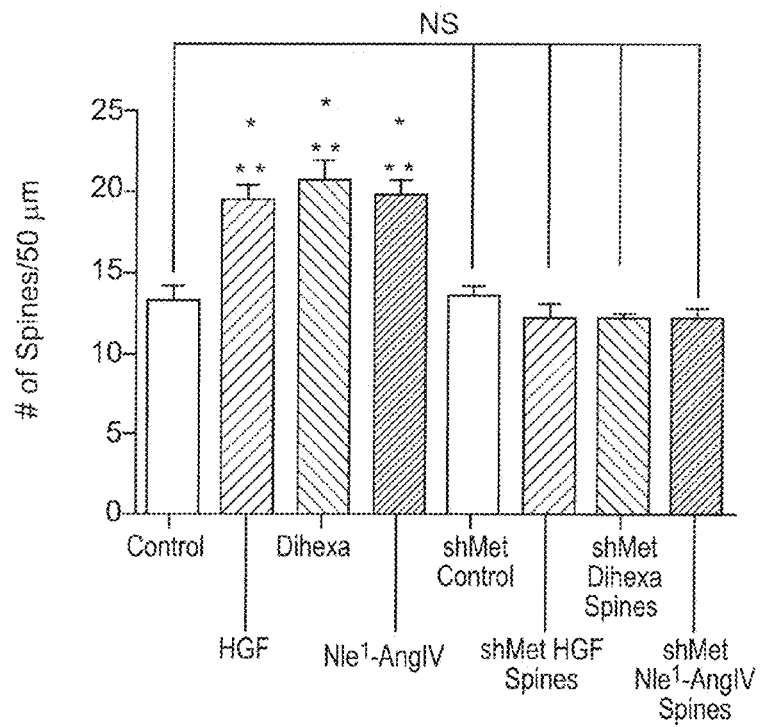
FIG. 20. Effect of c-Met knock-down on spinogenesis using a shRNA. The picture shows a Western blot probed for Myc. Hippocampal neurons transfected with mRFP-β-actin alone or with shMet to knock down the c-Met receptor were stimulated with HGF (10 ng/ml), Dihexa (10-12 M) or Nle1-AngIV (10-12 M) for 48 hours. Neurons transfected with mRFP-β-actin and stimulated with HGF, Dihexa or Nle1-AngIV significantly increased spinogenesis (* $P<0.05$; mean±S.E.M.; n=100). Those neurons transfected with mRFP-β-actin and shMet did not respond to stimulation with HGF, Dihexa or Nle1-AngIV treatment, confirming HGF and c-Met are the target ($P>0.05$; mean±S.E.M.; n=100).

Neurons transfected with mRFP-β-actin alone, serving as the control, were treated with 10 ng/ml HGF, $10^{-12}$ M Dihexa or Nle1-AngIV. A significant increase in the number of spines compared to control treated neurons was observed (mean spine numbers per 50 µm dendrite length=13.2 vs HGF=20.6; Dihexa=21.8 and Nle1-AngIV=20.0; p<0.05 by one-way ANOVA followed by Tukey post hoc test). Neurons transfected with mRFP-β-actin and shMet that were stimulated with 10 ng/ml HGF, $10^{-12}$ M Dihexa or Nle1-AngIV, did not differ from control in terms of spine numbers (mean spine numbers per 50 µm dendrite length=13.5 vs HGF=12.4; Dihexa=12.0 and Nle1-AngIV=12.1; p>0.05 by one-way ANOVA followed by Tukey post hoc test) as shown in FIG. 20. A scrambled RNA sequence was employed as the negative control and had no effect on basal or stimulated spinogenesis (data not shown). These results confirm that the effects of AngIV analogs are mediated by the HGF/c-Met system.

Figure 21:
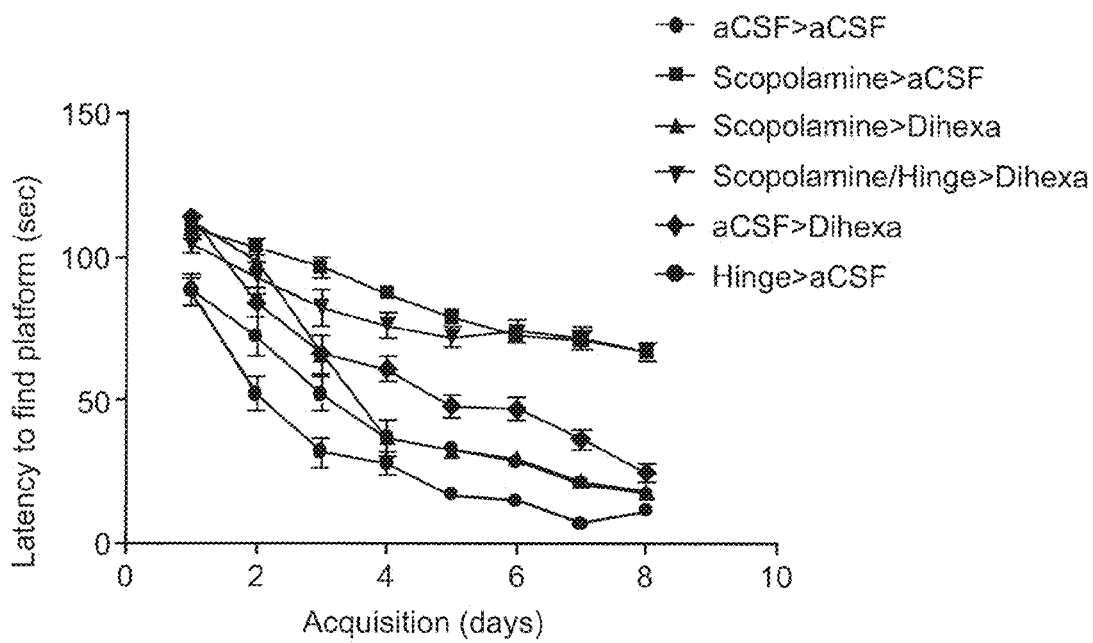
FIG. 21. HGF and c-Met have a function in spatial learning and memory. The latency to locate a submerged pedestal in the Morris water maze task of spatial learning and memory was tested on rats to ascertain the effects of HGF/c-Met on learning and memory. Rats received i.c.v. injections of amnestic drugs or HGF/c-Met receptor agonists. Rats treated with the scopolamine→scopolamine are unable to learn the task as measured by latency to escape. The group latencies for rats treated with aCSF→aCSF were significantly shorter than the scopolamine treated group on day one of training. Scopolamine→Dihexa treated rats and rats treated with Hinge→Hinge, while not significantly different from the scopolamine treated group on day one of training show rapid facilitation of the task. The group that received scopolamine+Hinge→Dihexa was not significantly different from the scopolamine treated animals and has long latencies to escape. Group latencies to locate a submerged pedestal in the Morris water maze task of spatial learning and memory. Hinge alone has no effect on learning; however Hinge in addition to scopolamine prevents facilitation of the task.

The Morris water maze, a hippocampal-dependent spatial learning task requiring rats to locate a pedestal hidden beneath the surface of the water by orienting themselves to extra-maze cues was employed to evaluate the impact of the HGF antagonist, Hinge, on the pro-cognitive effects of Dihexa. The groups tested included aCSF followed by aCSF, scopolamine (70 nM) followed by aCSF, scopolamine followed by Dihexa (300 pM), aCSF followed by Hinge (300 pM) and scopolamine+Hinge followed by Dihexa. FIG. 21 represents the mean latencies to find the hidden pedestal for days 1-8 of training in the water maze. None of the groups differed significantly in latency to find the pedestal on day one of training. Mean latencies for the vehicle control (aCSF→aCSF) group=89.3 s; the scopolamine treated group=114.7 s; the scopolamine+Hinge→Dihexa treated group latency=107.9 s; the Hinge group mean latency=111.1 s; and the scopolamine→Dihexa group=115.2 s. By the fourth day of training, considered to be a crucial day on which the most improvement in training and neural plasticity occurs (Meighan et al., 2006), the scopolamine group (mean latency to find the pedestal=102.4 s) and the scopolamine+Hinge→Dihexa group (mean latency=105.2 s) showed no signs of improvement compared to the vehicle control group (mean latency=43.0 s), the Hinge group (mean latency=78.3 s) and the scopolamine→Dihexa group (mean latency=63.0 s). On the final day of training when maximal learning has occurred (Meighan, Meighan et al. 2006) the mean latencies for the scopolamine group (mean latency to find the pedestal=84.8 s) and the scopolamine+Hinge→Dihexa group (mean latency=93.6 s) indicated little improvement in learning compared to the vehicle control group (mean latency=43.0 s), the Hinge group (mean latency=46.1 s) and the scopolamine→Dihexa group (mean latency 62.3 s). These results suggest that HGF and c-Met play an important role in hippocampal-dependent cognitive processes.

Discussion

The pro-cognitive effects of angiotensin IV analogues suggest that anti-dementia drugs based on this system can be developed. However, due to poor metabolic stability of angiotensin IV and many AngIV analogues, the inability of early analogues to penetrate the blood brain barrier, and the failure to identify the AT4 receptor, no pharmaceutical company has moved forward with their development. Dihexa, a novel angiotensin IV analogue synthesized by our laboratory, is stable and orally active and has thus overcome the major pharmacokinetic impediments preventing development. Dihexa has been proven to be stable in the blood for over 5 hours (not shown), survived passage through the gut to penetrate the blood brain barrier, and overcomes cognitive deficits in acute and chronic models of dementia (not shown). A general mechanism, established for facilitation of the water maze task, involves expansion of the dendritic arbor in the form of newly developed postsynaptic spines and accompanying synaptogenesis. The last remaining hurdle to development was the lack of a molecular mechanism.

Here we demonstrate that the actions of AngIV analogues are dependent on the HGF/c-Met system. Both systems appear to mediate similar physiological effects. It is known that the Angiotensin IV/AT4 system: has cerebroprotective effects, augments long term potentiation, has well established pro-cognitive effects, and is suspected to regulate neural stem cell development. The HGF/c-Met system also has pro-cognitive effects and is known to be involved in stem cell regulation. In addition to functional similarities there is sequence homology between angiotensin IV and the "hinge" linker region of HGF. This notion was further solidified by the observation that the well known AT4 antagonist, Norleual, is capable of blocking many HGF/c-Met regulated functions such as MDCK cell scattering.

Facilitation of the water maze task is effected by Dihexa and the parent angiotensin IV ligand, Nle1-AngIV, by augmentation of neurotransmission occurring through elaboration of the dendritic arbor. The hypothesized linkage between the action of AngIV analogues and the HGF/c-Met system predicted that like Dihexa and Nle1-AngIV HGF should be able to stimulate dendritic spine growth in dissociated hippocampal neurons. As predicted, HGF promoted a dose-dependent increase in spinogenesis (FIG. 7) in dissociated hippocampal neurons. The most effective concentration of HGF (10 ng/ml) was subsequently found to stimulate hippocampal neurons in organotypic hippocampal slice cultures which are more intact preparations similar to Dihexa (FIGS. 8A and B) further establishing a mechanistic link between Dihexa and HGF/c-Met. To evaluate the physiological relevance of these new spines and to determine the neurotransmitter signature of resident synapses, HGF treatment-induced spines labeled with mRFP-β-actin were immunostained for the universal presynaptic marker Synapsin that is located in the presynaptic active zones and the excitatory presynaptic marker VGLUT1 that is found at glutamatergic presynaptic synapses. The ratio of postsynaptic mRFP-β-actin labeled spines juxtaposed to Synapsin or VGLUT1 spines was not different from control treated neurons suggesting treatment-induced spines are forming functional synapses (FIG. 9A-D). Further validation of synaptogenesis was obtained by recording mEPSCs, spontaneous presynaptic bursts independent of action potentials, on HGF and Dihexa treated neurons. AMPA-mediated transmission was amplified in response to HGF and Dihexa treatment as shown by increased frequencies (FIG. 10).

Sub-threshold concentrations of Dihexa and HGF or Nle1-AngIV and HGF were used to stimulate hippocampal neurons in vitro to determine whether the angiotensin IV ligands Dihexa and Nle1-AngIV, and HGF affect the same signaling cascade or act on one receptor (c-Met). To determine whether Dihexa and Nle1-AngIV engage the same signaling cascade sub-threshold concentrations of AngIV ligands were combined with sub-threshold doses of HGF. While sub-threshold concentrations of each ligand alone did not alter basal spinogenesis, combined sub-threshold concentrations of $10^{-13}$ M Dihexa and 2.5 ng/ml HGF or $10^{-13}$ M Nle1-AngIV and 2.5 ng/ml of HGF produced a near ceiling effect, similar to biological responsive doses of each ligand alone (FIGS. 11A and B). The similarities in the dendritic responses to the AngIV analogues and HGF are consistent with a common mechanism of action.

Figure 12B:
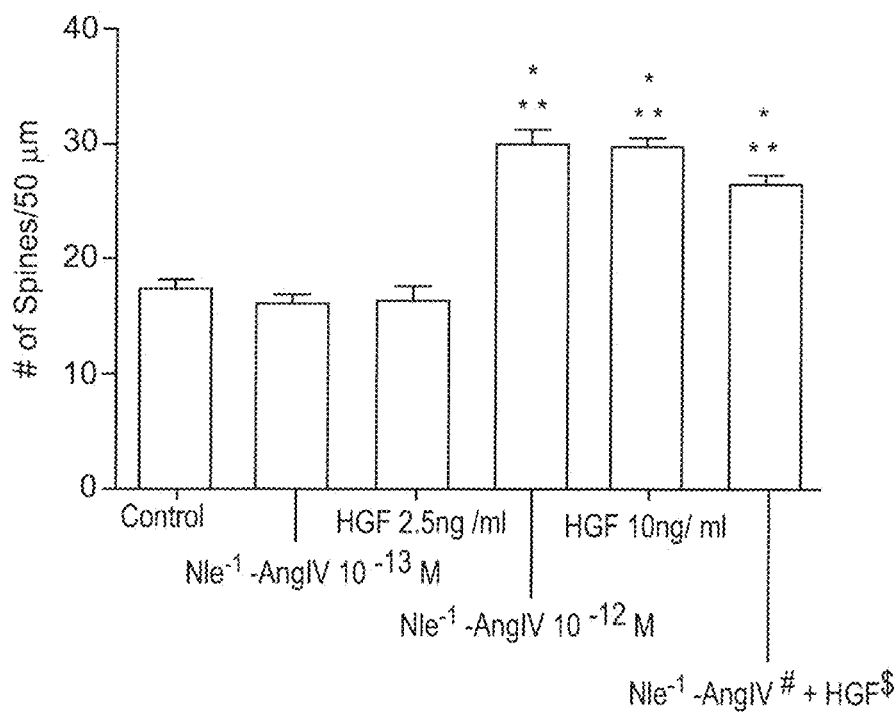

To further strengthen this perceived commonality of mechanism, the novel HGF antagonist Hinge was employed and evaluated for its effects on hippocampal neurons stimulated with AngIV analogues and HGF. Hinge, like the angiotensin IV antagonist Norleual, was established as a c-Met antagonist by its ability to block HGF-dependent c-Met phosphorylation and prevent HGF-dependent scattering in the MDCK epithelial cell line. Cell scattering, which is the hallmark of an HGF/c-Met interaction, leads to a loss of cell adhesion properties that allow cells to migrate. Hinge was found to have no adverse effects on cultured hippocampal neurons and did not promote or hinder spinogenesis (FIG. 12A). At pico molar concentrations, however, Hinge prevented HGF, Nle1-AngIV and Dihexa induced spinogenesis (FIG. 12B-D) further suggesting that the effects observed for our angiotensin IV ligands are HGF/c-Met mediated. The effects of Hinge on synaptogenesis were evaluated by recording mEPSC frequencies on cultured hippocampal neurons. While Hinge alone did alter base-line synaptic transmission it attenuated HGF and Dihexa increases in AMPA-frequencies (FIGS. 13 A and B). This effect was likely due to attenuation of spinogenesis promoted by HGF and Dihexa treatments since, without the antagonizing effect of Hinge, each agonist increased mini-AMPA frequencies (FIG. 13 A-B and FIG. 10) thus forming functional synaptic connections. Taken together, these data suggest that inhibiting HGF does not alter the number of functional synapses in vehicle treated neurons but attenuates the effects of HGF and Dihexa on synaptogenesis by decreasing the number of postsynaptic spines.

To additionally support the contention that the agonists Dihexa and Nle1-AngIV are acting through HGF and its receptor c-Met, hippocampal neurons were transfected with shRNA to knockdown the c-Met receptor. Knockdown of the receptor was verified by immunoblotting against a Myc-tagged c-Met gene product (FIG. 16). As expected, stimulation of hippocampal neurons transfected with mRFP-β-actin with HGF, Dihexa and Nle1-AngIV had significantly enhanced dendritic arbors while those additionally transfected with she-Met RNA were no different from control treated neurons (FIG. 17). These data conclusively show that angiotensin IV ligands Dihexa and Nle1-AngIV act through the HGF/c-Met system.

The newly developed angiotensin IV agonist ligand Dihexa has been shown to facilitate acquisition of a spatial learning and memory task in scopolamine treated rats (data not shown). Because it is prohibitively expensive to test HGF in the water maze, we instead evaluated its involvement in cognition by employing the HGF antagonist Hinge to block the actions of Dihexa. Treatment with the muscarinic cholinergic receptor antagonist scopolamine renders rats acutely amnesic and therefore unable to learn the task. A rescue effect is observed in rats that are given Dihexa following scopolamine pretreatment. These rats exhibit rapid facilitation of the task and did not perform differently from vehicle treated rats. The group of rats that was pretreated with a scopolamine and Hinge did not display the rescue effect observed by Dihexa in the scopolamine preparation (FIGS. 14A and B). These data demonstrate a function for HGF and c-Met system in learning and memory, and that agents which mimic the action of HGF can be used to enhance learning and memory in subjects in need thereof.

Example 3

Development of Antiotensin IV Analogs as Hepatocyte Growth Factor/Met Modifiers

The 6-AH family [D-Nle-X-Ile-NH—$(CH_2)_5$—$CONH_2$; where X=various amino acids] of Angiotensin IV analogs, bind directly to Hepatocyte Growth Factor (HGF) and inhibit HGF's ability to form functional dimers. The metabolically stabilized 6-AH family member, D-Nle-Tyr-Ile-NH—$(CH_2)_5$—$CONH_2$, had a $t_{1/2}$ in blood of 80 min compared to the parent compound Norleual (Nle-Tyr-Leu-Ψ-$(CH_2$—$NH_2)^{3-4}$-His-Pro-Phe, SEQ ID NO: 1), which had a $t_{1/2}$ in blood of <5 min. 6-AH family members were found to act as mimics of the dimerization domain of HGF (hinge region), and inhibited the interaction of an HGF molecule with a $^3$H-hinge region peptide resulting in an attenuated capacity of HGF to activate its receptor Met. This interference translated into inhibition of HGF-dependent signaling, proliferation, and scattering in multiple cell types at concentrations down into the low picomolar range. We also noted a significant correlation between the ability of the 6-AH family members to block HGF dimerization and inhibition of the cellular activity. Further, a member of the 6-AH family with cysteine at position 2, was a particularly effective antagonist of HGF-dependent cellular activities. This compound suppressed pulmonary colonization by B16-F10 murine melanoma cells, which are characterized by an overactive HGF/Met system. Together these data indicate that the 6-AH family of AngIV analogs exert their biological activity by modifying the activity of the HGF/Met system and offer the potential as therapeutic agents in disorders that are dependent on or possess an over-activation of the HGF/Met system.

Introduction

The multifunctional growth factor hepatocyte growth factor (HGF) and its receptor Met are important mediators for mitogenesis, motogenesis, and morphogenesis in a wide range of cell types including epithelial, endothelial, and hematopoietic cells, neurons, melanocytes, and hepatocytes. Furthermore, dysregulation of the HGF/Met system often leads to neoplastic changes and to cancer (in both human and animal) where it contributes to tumor formation, tumor metastasis, and tumor angiogenesis. Over-activation of this signaling system is routinely linked to poor patient prognosis. Therefore molecules that inhibit the HGF/Met system can be expected to exhibit anti-cancer activity and attenuate malignant and metastatic transformations.

HGF is a vertebrate heteromeric polypeptide growth factor with a domain structure that closely resembles the proteinases of the plasminogen family. HGF consists of seven domains: an amino terminal domain, a dimerization-linker domain, four kringle domains (K1-K4), and a serine proteinase homology (SPH) domain. The single chain pro-polypeptide is proteolytically processed by convertases to yield a mature a (heavy chain 55 KDa), and β (light chain 34 KDa) heterodimer, which are bound together by a disulfide link. In addition to proteolytic processing, HGF requires dimerization to be fully activated. Several reports have shown that HGF forms dimers and/or multimers, which are arranged in a head-to-tail orientation, prior to its interaction with Met. The dimer interface, which encompasses the inter-domain linker amino acids (K122, D123, Y124, I125, R126, and N127) is referred to as the hinge region. Although both pre-pro-HGF and the active disulfide-linked heterodimer bind Met with high affinity, it is only the heterodimer that is capable of activating Met.

Recent studies from our laboratory have shown that picomolar concentrations of the AngIV analog, Norleual (Nle-Tyr-Leu-ψ-$(CH_2$—$NH_2)^{3-4}$-His-Pro-Phe), are capable of potently inhibiting the HGF/Met system and bind directly to the hinge region of HGF blocking its dimerization. Moreover, a hexapeptide representing the actual hinge region possessed biochemical and pharmacological properties identical to Norleual's. The major implication of those studies was that molecules, which target the dimerization domain of HGF, could represent novel and viable anti-cancer therapeutics. Additionally, these data support the development of such molecules using Norleual and/or the Hinge peptide as synthetic templates.

Despite its marked anti-cancer profile Norleual is highly unstable making its transition to clinical use problematic. Thus a family of metabolically stabile Ang IV-related analogs has been developed in our laboratory, which are referred to here as the 6-AH family because of 6-amino hexanoic amide substituted at the C-terminal position. This substitution along with D-norleucine at the N-terminal enhances the metabolic resistance of family members.

In this Example 3, it is demonstrated that 6-AH family members (i.e., HGF Mimics) have superior metabolic stability when compared to Norleual, bind to HGF with high affinity, and act as hinge region mimics; thus preventing HGF dimerization and activation. This interference translates into inhibition of HGF-dependent signaling, proliferation, and scattering in multiple cell types at concentration in the picomolar range. A positive correlation was evident between the ability to block dimerization and the inhibition of the cellular outcomes of HGF activation. Finally D-Nle-Cys-Ile-NH—(CH$_2$)$_5$—CONH$_2$, a member of the 6-AH family suppressed pulmonary colonization by B16-F10 murine melanoma cells, which are characterized by an overactive HGF/Met system. This Example highlights the ability of AngIV-like molecules to bind to HGF, block HGF dimerization, and inhibit the HGF/Met system. Moreover, these HGF mimics have utility as AngIV-related pharmaceuticals and can function as therapeutic agents in disorders where inhibition of the HGF/Met system would be clinically advantageous.

Material and Methods

Animals.

C57BL/6 mice from Taconic farms were used in the lung colonization studies. Male Sprague-Dawley rats (250+ g) were obtained from Harlan Laboratories (CA, USA) for use in pharmacokinetic studies. Animals were housed and cared for in accordance with NIH guidelines as described in the "Guide for the Care and Use of Laboratory Animals".

Compounds.

D-Nle-X-Ile-NH—(CH$_2$)$_5$—COOH; where X=various amino acids and Norleual (Nle-Tyr-Leu-ψ-(CH$_2$—NH$_2$)$^{3-4}$-His-Pro-Phe, SEQ ID NO: 1) were synthesized using Fmoc based solid phase methods in the Harding laboratory and purified by reverse phase HPLC. Purity and structure were verified by LC-MS. Hepatocyte growth factor (HGF) was purchased from R&D Systems (Minneapolis, Minn.).

Antibodies.

Anti-Met was purchased from Cell Signaling Technology (Beverly, Mass.) and the phospho-Met antibody was purchased from AbCam, Inc (Cambridge, Mass.).

Cell Culture.

Human embryonic kidney cells 293 (HEK293) and Madin Darby canine kidney cells (MDCK) were grown in DMEM, 10% fetal bovine serum (FBS). Cells were grown to 100% confluency before use. HEK and MDCK cells were serum starved for 2-24 h prior to the initiation of drug treatment.

Blood Stability Studies.

To compare the blood stability of Norleual and D-Nle-Tyr-Ile-NH—(CH$_2$)$_5$—CONH$_2$, a representative member of the 6-AH family, 20 μL of compound-containing vehicle (water [Norleual] or 30% ethanol [D-Nle-Tyr-Ile-NH—(CH$_2$)$_5$—CONH$_2$]) was added to 180 μL of heparinized blood and incubated at 37° C. for various times. For Norleual, 37° C. incubations were stopped at 0, 20, 40, and 60 min, and for D-Nle-Tyr-Ile-NH—(CH$_2$)$_5$—CONH$_2$, incubations were stopped at 0, 1, 3 and 5 h.

At the end of each incubation, 20 μL of Nle$^1$-AngIV (100 μg/mL) was added to each sample as an internal standard. D-Nle-Tyr-Ile-NH—(CH$_2$)$_5$—CONH$_2$ samples were centrifuged at 4° C. for 5 min at 2300×g to pellet erythrocytes, and the plasma was transferred to clean tubes. The Norleual and D-Nle-Tyr-Ile-NH—(CH$_2$)$_5$—CONH$_2$ samples were precipitated by adding 3 vol of ice-cold acetonitrile (ACN) and the samples were vortexed vigorously. All samples were centrifuged at 4° C., 2300×g for 5 min and the supernatants were transferred to clean tubes. Samples were then evaporated to dryness in a Savant SpeedVac® concentrator (Thermo Fisher Scientific, Waltham, Mass.), the residue was reconstituted in 225 μl 35% methanol, vortexed briefly, transferred to HPLC autosampler vials, and 100 μl injected into the HPLC system.

Samples were then separated by HPLC on an Econosphere C18 (100 mm×2.1 mm) from Grace Davison Discovery Science (Deerfield, Ill.). Peaks were detected and analyzed by mass spectrographic methods using a LCMS-2010EV mass spectrometer (Shimadzu, Kyoto Japan). The mobile phase consisted of HPLC water (Sigma St. Louis, Mo.) with 0.1% trifluoroacetic or 0.1% heptafluorobutyric acid (Sigma St. Louis, Mo.) and varying concentrations of ACN or methanol. Separation was carried out using a gradient method, at ambient temperature and a flow rate of 0.3 mL/min (see below for more information). Stability half-lives were determined assuming a normal single phase exponential decay using Prism 5 graphical/statistical program (GraphPad, San Diego, Calif.).

IV Pharmacokinetics

Surgical Procedures.

Male Sprague-Dawley rats (250+ g) were allowed food (Harlan Teklad rodent diet) and water ad libitum in our AAALAC certified animal facility. Rats were housed in temperature-controlled rooms with a 12 h light/dark cycle. The right jugular veins of the rats were catheterized with sterile polyurethane Hydrocoat™ catheters (Access Technologies, Skokie, Ill., USA) under ketamine (Fort Dodge Animal Health, Fort Dodge, Iowa, USA) and isoflurane (Vet One™, MWI, Meridian, Id., USA) anesthesia. The catheters were exteriorized through the dorsal skin. The catheters were flushed with heparinized saline before and after blood sample collection and filled with heparin-glycerol locking solution (6 mL glycerol, 3 mL saline, 0.5 mL gentamycin (100 mg/mL), 0.5 mL heparin (10,000 u/mL)) when not used for more than 8 h. The animals were allowed to recover from surgery for several days before use in any experiment, and were fasted overnight prior to the pharmacokinetic experiment.

Pharmacokinetic Study.

Catheterized rats were placed in metabolic cages prior to the start of the study and time zero blood samples were collected. Animals were then dosed intravenously via the jugular vein catheters, with D-Nle-Tyr-Ile-NH—(CH$_2$)$_5$—CONH$_2$ (24 mg/kg) in 30% ethanol. After dosing, blood samples were collected as follows (times and blood volumes collected are listed in chronological order):

| Compound | Time (min) | Blood Volume Collected (μl) |
| --- | --- | --- |
| D-Nle-Tyr-Ile-NH—(CH$_2$)$_5$—CONH$_2$ | 0, 12, 30, 60, 90, 120, 180, 240, 300 | 200, 200, 200, 200, 200, 300, 400, 500, 500 |

After each blood sample was taken, the catheter was flushed with saline solution and a volume of saline equal to the volume of blood taken was injected (to maintain total blood volume).

Blood Sample Preparation.

Upon collection into polypropylene microfuge tubes without heparin, blood samples were immediately centrifuged at 4° C., 2300×g for 5 min to remove any cells and clots and the serum transferred into clean microcentrifuge tubes. A volume of internal standard (Nle$^1$-AngIV, 100 μg/mL) equal to 0.1 times the sample serum volume was added. A volume of ice-cold acetonitrile equal to four times the sample serum volume was then added and the sample vortexed vigorously for 30 s. The supernatants were transferred to clean tubes, then held on ice until the end of the experiment, and stored at 4° C. afterward until further processing.

Serial dilutions of D-Nle-Tyr-Ile-NH—(CH$_2$)$_5$—CONH$_2$ in 30% ethanol were prepared from the stock used to dose the animals for standard curves. 20 μL of each serial dilution was added to 180 μL of blood on ice for final concentrations of 0.01 μg/mL, 0.1 μg/mL, 1 μg/mL and 10 μg/mL. The samples were centrifuged at 4° C., 2300×g for 5 min and the serum transferred into polypropylene microcentrifuge tubes. A volume of internal standard (Nle$^1$-AngIV, 100 µg/mL) equal to 0.1 times the sample serum volume was added. A volume of ice-cold acetonitrile equal to four times the sample serum volume was then added and the sample vortexed vigorously for 30 s. The supernatants were transferred to clean tubes and samples stored at 4° C. and processed alongside the pharmacokinetic study samples. All samples were evaporated to dryness in a Savant SpeedVac® concentrator. The residue was reconstituted in 225 µl 35% methanol and vortexed briefly. The samples were then transferred to HPLC autosampler vials and 100 µl was injected into the HPLC system a total of 2 times (2 HPLC/MS analyses) for each sample.

Chromatographic System and Conditions.

The HPLC/MS system used was from Shimadzu (Kyoto, Japan), consisting of a CBM-20A communications bus module, LC-20AD pumps, SIL-20AC auto sampler, SPD-M20A diode array detector and LCMS-2010EV mass spectrometer. Data collection and integration were achieved using Shimadzu LCMS solution software. The analytical column used was an Econosphere C18 (100 mm×2.1 mm) from Grace Davison Discovery Science (Deerfield, Ill., USA). The mobile phase consisted of HPLC grade methanol and water with 0.1% trifluoroacetic acid. Separation was carried out using a non-isocratic method (40%-50% methanol over 10 min) at ambient temperature and a flow rate of 0.3 mL/min. For MS analysis, a positive ion mode (Scan) was used to monitor the m/z of D-Nle-Tyr-Ile-NH—(CH$_2$)$_5$—CONH$_2$ at 542 and the m/z of Nle$^1$-AngIV (used for internal standard) at 395. Good separation of D-Nle-Tyr-Ile-NH—(CH$_2$)$_5$—CONH$_2$ and the internal standard in blood was successfully achieved. No interfering peaks co-eluted with the analyte or internal standard. Peak purity analysis revealed a peak purity index for D-Nle-Tyr-Ile-NH—(CH$_2$)$_5$—CONH$_2$ of 0.95 and the internal standard of 0.94. D-Nle-Tyr-Ile-NH—(CH$_2$)$_5$—CONH$_2$ eluted at 5.06 min and the internal standard at 4.31 min. Data were normalized based on the recovery of the internal standard.

Pharmacokinetic Analysis.

Pharmacokinetic analysis was performed using data from individual rats. The mean and standard deviation (SD) were calculated for the group. Noncompartmental pharmacokinetic parameters were calculated from serum drug concentration-time profiles by use of WinNonlin® software (Pharsight, Mountain View, Calif., USA). The following relevant parameters were determined where possible: area under the concentration-time curve from time zero to the last time point (AUC$_{0-last}$) or extrapolated to infinity (AUC$_{0-\infty}$), C$_{max}$ concentration in plasma extrapolated to time zero (C$_0$), terminal elimination half-life (t$_{1/2}$), volume of distribution (Vd), and clearance (CL).

Microsomal Metabolism.

Male rat liver microsomes were obtained from Celsis (Baltimore, Md., USA). The protocol from Celsis for assessing microsomal-dependent drug metabolism was followed with minor adaptations. An NADPH regenerating system (NRS) was prepared as follows: 1.7 mg/mL NADP, 7.8 mg/mL glucose-6-phosphate and 6 units/mL glucose-6-phosphate dehydrogenase were added to 10 mL 2% sodium bicarbonate and used immediately. 500 µM solutions of Norleual, D-Nle-Tyr-Ile-NH—(CH$_2$)$_5$—CONH$_2$, piroxicam, verapamil and 7-ethoxycoumarin (low, moderate and highly metabolized controls, respectively) were prepared in acetonitrile. Microsomes were suspended in 0.1M Tris buffer (pH 7.38) at 0.5 mg/mL and 100 µL of the microsomal suspension was added to pre-chilled microcentrifuge tubes on ice. To each sample, 640 µL 0.1M Tris buffer, 10 µL 500 µM test compound, and 250 µL of NRS was added. Samples were incubated in a rotisserie hybridization oven at 37° C. for the appropriate incubation times (10, 20, 30 40 or 60 min). 500 µL from each sample was transferred to tubes containing 500 µL ice-cold acetonitrile with internal standard per incubation sample. Standard curve samples were prepared in incubation buffer and 500 µL added to 500 µL ice-cold acetonitrile with internal standard. All samples were then analyzed by high performance liquid chromatography/mass spectrometry. Drug concentrations were determined and loss of parent relative to negative control samples containing no microsomes was calculated. Clearance was determined by nonlinear regression analysis for k$_e$ and t$_{1/2}$ and the equation Cl$_{int}$=k$_e$ Vd. For in vitro-in vivo correlation, Cl$_{int}$ per kg body weight was calculated using the following measurements for Sprague-Dawley rats: 44.8 mg of protein per g of liver, 40 g of liver per kg of body weight.

HGF Binding.

The binding of 6-AH analogs to HGF was assessed by competition using a soluble binding assay. 250 µl of PBS containing human HGF (1.25 ng) were incubated with $^3$H-Hinge, the central dimerization domain of HGF, in the presence of varying concentrations of 6-AH analogs between $10^{-13}$ M to $10^{-7}$ M (half-log dilutions) for 40 min at 37° C. The incubates were then spun through Bio-Gel P6 spin columns (400 µl packed volume) for 1 min to separate free and bound $^3$H-Hinge and the eluent was collected. Five milliliters of scintillation fluid was added to the eluent, which contained the HGF bound $^3$H-Hinge, and was then counted using scintillation counter. Total disintegrations per minute of bound $^3$H-Hinge were calculated based on machine counting efficiency. The Ki values for the binding of the peptides were determined using the Prism 5. Competition binding curves were performed in triplicate. Preliminary kinetic studies indicated that equilibrium binding was reached by 40 min of incubation at 37° C. $^3$H-Hinge has recently been shown to bind to HGF with high affinity (Kawas et al., 2011).

HGF Dimerization.

HGF dimerization was assessed using PAGE followed by silver staining (Kawas et al., 2011). Human HGF at a concentration of 0.08 ng/µl with or without 6-AH analogs was incubated with heparin at a final concentration of 5 µg/ml. Loading buffer was then added to each sample and the mixture separated by native PAGE using gradient Criterion XT precast gels (4-12% Bis-Tris; Biorad Laboratories, Hercules, Calif.). Next the gel was silver stained for the detection of the HGF monomers and dimers. Bands were quantitated from digital images using a UVP phosphoimager (Upland, Calif.).

Western blotting.

HEK293 cells were seeded in 6 well tissue culture plates and grown to 95% confluency in DMEM containing 10% FBS. The cells were serum deprived for 24 h prior to the treatment to reduce the basal levels of phospho-Met. Following serum starvation, cocktails comprised of vehicle and HGF with/without 6-AH analogs were prepared and pre-incubated for 30 min at room temperature. The cocktail was then added to the cells for 10 min to stimulate the Met receptor and downstream proteins. Cells were harvested using RIPA lysis buffer (Millipore; Billerica, Mass.) fortified with phosphatase inhibitor cocktails 1 and 2 (Sigma-Aldrich; St. Louis, Mo.). The lysate was clarified by centrifugation at 15,000 nx g for 15 min, protein concentrations were determined using the BCA total protein assay (Pierce), and then appropriate volumes of the lysates were diluted with 2× reducing Laemmli buffer and heated for ten min at 95° C. Samples containing identical amounts of protein were resolved using SDS-PAGE (Criterion, BioRad Laboratories), transferred to nitrocellulose, and blocked in Tris-buffered saline (TBS) containing 5% milk for 1 h at room temperature. The phospho-Met antibody were added to the blocking buffer at a final concentration of 1:1000 and incubated at 4° C. overnight with gentle agitation. The membranes were then washed several times with water and TBS (PBS, 0.05% Tween-20), a 1:5000 dilution of horseradish-peroxidase conjugated goat anti-rabbit antiserum was added, and the membranes further incubated for 1 h at room temperature. Proteins were visualized using the Supersignal West Pico Chemiluminescent Substrate system (Pierce, Fenton, Mo.) and molecular weights determined by comparison to protein ladders (BenchMark, Invitrogen, and Kaleidoscope, BioRad). Film images were digitized and analyzed using a UVP phosphoimager.

Cell Proliferation.

5000 MDCK cells were seeded into the wells of a 96 well plates in 10% FBS DMEM. To induce cellular quiescence, the cells were serum deprived for 24 h prior to initiating the treatments. Following serum starvation, 10 ng/ml HGF alone and with various concentrations of 6-AH analogs or PBS vehicle were added to the media. The cells were allowed to grow under these conditions for 4 days with a daily addition of 6-AH analogs. On the fourth day, 1 mg/ml of 1-(4,5-Dimethylthiazol-2-yl) 3,5-diphenylformazan reagent (MTT, Sigma-Aldrich) prepared in PBS was added to the cells and incubated for 4 h. Dimethyl sulfoxide diluted in a 0.01M glycine buffer was added to solubilize the cell membranes and the absorbance of reduced MTT in the buffer was quantitated at 590 nm using a plate reader (Biotek Synergy 2, Winooski, Vt.). HGF-dependent proliferation was determined by subtracting the basal proliferation (in the absence of HGF) from total proliferation rates in groups containing HGF.

Scattering Assay.

MDCK cells were grown to 100% confluency on the coverslips in six-well plates and washed twice with PBS. The confluent coverslips were then aseptically transferred to new six well plates containing 900 µl serum free DMEM. Norleual, Hinge peptide, and/or HGF (20 ng/ml) were added to appropriate wells. Control wells received PBS vehicle. Plates were incubated at 37° C. with 5% $CO_2$ for 48 h. Media was removed and cells were fixed with methanol. Cells were stained with Diff-Quik Wright-Giemsa (Dade-Behring, Newark, Del.) and digital images were taken. Coverslips were removed with forceps and more digital images were captured. Pixel quantification of images was achieved using Image J and statistics were performed using Prism 5 and InStat v.3.05 (GraphPad; San Diego, Calif.).

Lung Colony Formation.

Six to eight month old C57BL/6 mice were injected with 400,000 B16-F10 cells in 200 µl PBS by tail vein injection and subsequently received daily intraperitoneal injections of either D-Nle-X-Cys-NH—$(CH_2)_5$—$CONH_2$ (10 µg/kg and 100 µg/kg) or a PBS vehicle control. Two weeks later, mice were anesthetized and lungs were perfused with PBS and removed. Photos were taken and lungs were solubilized in 1% Triton x-100, 20 mM Tris, 0.15 M NaCl, 2 mM EDTA, and 0.02% sodium azide. Samples were disrupted by sonication (Mixonix, Farmingdale, N.Y.) and spun. The supernatant was transferred to a 96 well plate and melanin absorbance at 410 mm was measured using a plate reader.

Statistics.

Independent one-way analysis of variance (ANOVA) (InStat v.3.05 and Prism 5) was used to determine differences among groups. Tukey-Kramar or Bonferroni's multiple comparison post-hoc tests were performed where necessary. Statistical comparisons of two groups were determined using the two-tailed Student's t-test (InStat v.3.05 and Prism 5).

Results

The AngIV Analog D-Nle-Tyr-Ile-NH—$(CH_2)_5$—$CONH_2$ is More Metabolically Stable than Norleual (Nle-Tyr-Leu-ψ-$(CH_2$—$NH_2)^{3\text{-}4}$-His-Pro-Phe (SEQ ID NO: 1)

Figure 22:
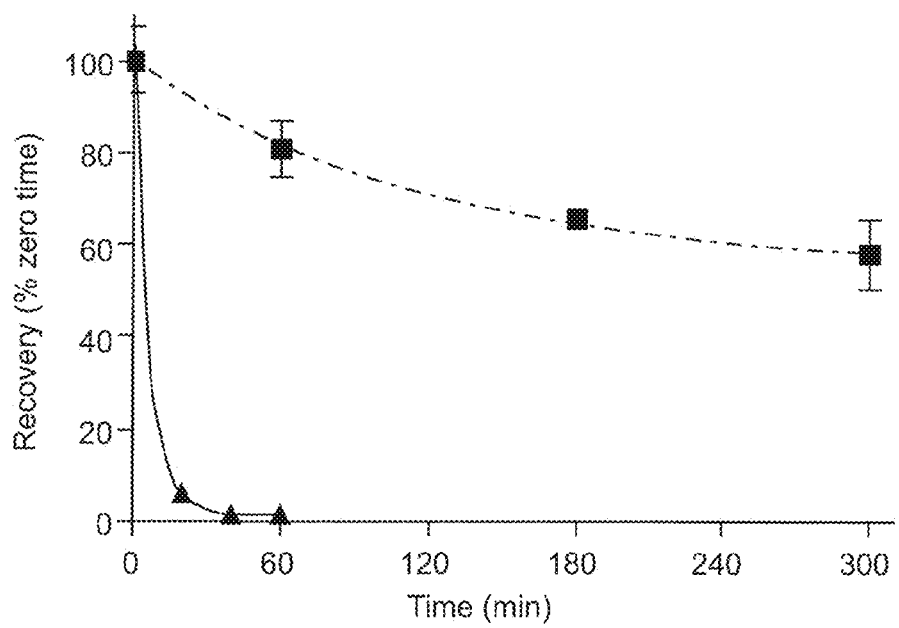
FIG. 22. Stability of Norleual in rat blood as compared to D-Nle-Tyr-Ile-NH—(CH$_2$)$_5$—CONH$_2$. ◆ Norleual and ■ D-Nle-Tyr-Ile-NH—(CH$_2$)$_5$—CONH$_2$ were incubated in heparinized rat blood at 37° C.; the figure shows percent recovery over time (mean±SD). The calculated stability t$_{1/2}$ based on single phase exponential decay for Norleual was 4.6 min and for D-Nle-Tyr-Ile-NH—(CH$_2$)$_5$—CONH$_2$ stability t$_{1/2}$ was 79.97 min.

The AngIV-related peptidomimetic Norleual was previously shown to possess, anti-HGF/Met, anti-angiogenic, and anti-cancer activities. The presence of unprotected peptide bonds at both the N- and C-terminal linkages predicts that Norleual should have poor metabolic stability and rapid clearance for the circulation, properties that may limit its clinical utility. In an attempt to overcome this limitation, a family of compounds, the 6-AH family was designed and synthesized to offer defense against exopeptidases. FIG. 22 demonstrates that as expected Norleual is unstable in heparinized blood while D-Nle-Tyr-Ile-NH—$(CH_2)_5$—$CONH_2$ exhibited improved stability.

The AngIV Analog D-Nle-Tyr-Ile-NH—$(CH_2)_5$—$CONH_2$ has a Much Longer Circulating Half-Life than Norleual (Nle-Tyr-Leu-ψ-$(CH_2$—$NH_2)^{3\text{-}4}$-His-Pro-Phe (SEQ ID NO: 1))

As anticipated from the in-vitro blood stability data, D-Nle-Tyr-Ile-NH—$(CH_2)_5$—$CONH_2$ exhibited an extended in vivo elimination half-life of 1012 min after IV injection in rats. Other relevant pharmacokinetic parameters of D-Nle-Tyr-Ile-NH—$(CH_2)_5$—$CONH_2$ after a single IV bolus dose are summarized in Table 5. Serum data were modeled using WinNonlin® software to perform non-compartmental analysis. D-Nle-Tyr-Ile-NH—$(CH_2)_5$—$CONH_2$ appeared to be extensively distributed outside the central blood compartment and/or bound within the tissues as evidenced by its large volume of distribution (Vd). D-Nle-Tyr-Ile-NH—$(CH_2)_5$—$CONH_2$ is not expected to be highly bound to plasma proteins according to quantitative structure-activity relationship (QSAR) modeling (discussed below) and since total recovery from serum was greater than 35%. These results, which suggest that D-Nle-Tyr-Ile-NH—$(CH_2)_5$—$CONH_2$ is likely to be relatively hydrophobic, are in agreement with the outcome of QSAR modeling estimates generated by ADMET Predictor® that calculated an octanol:water partition coefficient of 28.18 for D-Nle-Tyr-Ile-NH—$(CH_2)_5$—$CONH_2$ (Table 6).

Not surprisingly because of its stability, hydrophobic character, and small size, D-Nle-Tyr-Ile-NH—$(CH_2)_5$—$CONH_2$ was predicted to be orally bioavailable. The $P_{eff}$ value represents the predicted effective human jejunal permeability of the molecule. The predicted $P_{eff}$ value for D-Nle-Tyr-Ile-NH—$(CH_2)_5$—$CONH_2$ (1.53) is intermediate between the predicted $P_{eff}$ values for enalapril (1.25) and piroxicam (2.14), two orally bioavailable drugs. D-Nle-Tyr-Ile-NH—$(CH_2)_5$—$CONH_2$ was also predicted to be 42.68 percent unbound to plasma proteins in circulation, thus making it available for distribution into the tissues.

Also contributing to its slow removal from the blood was a lack of Phase I metabolism for D-Nle-Tyr-Ile-NH—$(CH_2)_5$—$CONH_2$. D-Nle-Tyr-Ile-NH—$(CH_2)_5$—$CONH_2$ exhibited no detectable metabolism over 90 min in an in-vitro metabolism assay using rat liver microsomes (data not shown). Together these data indicate that D-Nle-Tyr-Ile-NH—$(CH_2)_5$—$CONH_2$ is more metabolically stable than Norleual, possesses an elongated half-life in the circulation and penetrates tissue effectively. Overall these favorable pharmacokinetic properties justify the mechanistic and therapeutic evaluation of D-Nle-Tyr-Ile-NH—$(CH_2)_5$—$CONH_2$ and related molecules.

Figure 23:
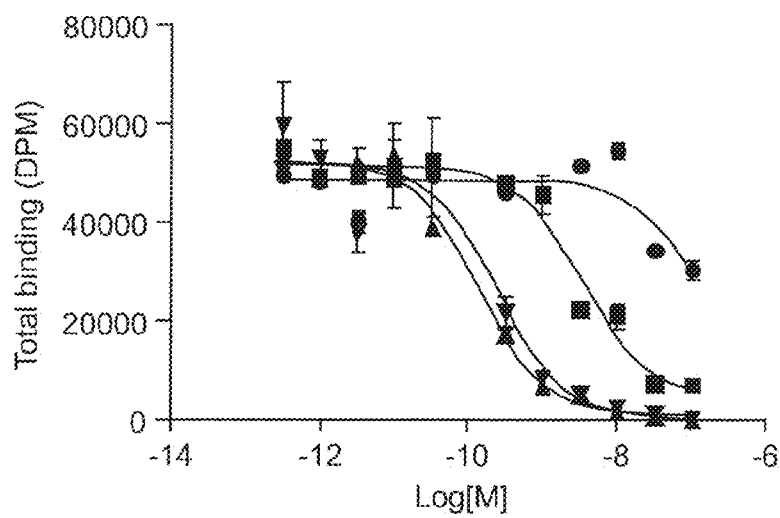
FIG. 23. Binding of D-Nle-X-Ile-NH—(CH$_2$)$_5$—CONH$_2$ analogs to HGF. Representative curves illustrating the competition of D-Nle-X-Ile-NH—(CH$_2$)$_5$—CONH$_2$ analogs for $^3$H-Hinge binding to HGF. The D-Nle-X-Ile-NH—(CH$_2$)$_5$—CONH$_2$ analogs and $^3$H-Hinge (13.3×10$^{-12}$M) were incubated with 1.25 ng of HGF for 40 min at 37° C. in 0.25 ml of buffer. HGF-bound Hinge was eluted from Bio-Gel P6 columns after the addition of different concentrations of the D-Nle-X-Ile-NH—(CH$_2$)$_5$—CONH$_2$ analogs (10$^{-13}$-10$^{-7}$M). The radioactivity of the eluted solutions was quantitated using scintillation counting. These data demonstrate that the D-Nle-X-Ile-NH—(CH$_2$)$_5$—CONH$_2$ analogs exhibit a range of affinities for HGF. The K$_i$s for the Met, Trp, Cys, and Tyr analogs were respectively determined to be: 1.375×10$^{-07}$M, 3.372×10$^{-09}$M, 1.330×10$^{-10}$M, and 2.426×10$^{-10}$ M; N=9. ▲ D-Nle-Cys-Ile-NH—(CH$_2$)$_5$—CONH$_2$, ◆ D-Nle-Met-Ile-NH—(CH$_2$)$_5$—CONH$_2$, ■ D-Nle-Trp-Ile-NH—(CH$_2$)$_5$—CONH$_2$, ▼ D-Nle-Tyr-Ile-NH—(CH$_2$)$_5$—CONH$_2$.

D-Nle-X-Ile-NH—(CH$_2$)$_5$—CONH$_2$ Analogs Bind HGF and Compete with the $^3$H-Hinge Peptide for HGF Binding Several members of the D-Nle-X-Ile-NH—(CH$_2$)$_5$—CONH$_2$, 6-AH family, were analyzed for the capacity to compete for $^3$H-Hinge binding to HGF. As will be evident below, members of the 6-AH family display a varied ability to block the biological action of HGF. As such, the HGF binding properties of a selection of analogs with varying biological activity was assessed to determine if there was a relationship between inhibitory activity and affinity for HGF. The hypothesis that was put forth was that analogs are binding directly to HGF and affecting the sequestration of HGF in an inactive form. To begin the evaluation of this idea, we used a $^3$H-Hinge peptide as a probe to assess direct HGF binding of the peptides. The use of $^3$H-Hinge to probe the interaction was based on the ability of $^3$H-Hinge to bind specifically and with high affinity to HGF (Kawas et al., 2011). A competition study was initiated with several derivatives of the D-Nle-X-Ile-NH—(CH$_2$)$_5$—CONH$_2$ family. This study demonstrated that different analogs have variable abilities to bind HGF, and that the analogs showing antagonism to HGF are acting as a Hinge mimics. D-Nle-X-Ile-NH—(CH$_2$)$_5$—CONH$_2$ derivatives were found to compete with Hinge for HGF binding and exhibited a range of affinities for HGF, with K$_i$s ranging from 1.37×10$^{-7}$-1.33×10$^{-10}$M (FIG. 23). As expected it appears to be relationship between a compound's ability to bind HGF and its capacity to block dimerization and inhibit HGF-dependent activities (see FIGS. 25, 26, 27).

D-Nle-X-Ile-NH—(CH$_2$)$_5$—CONH$_2$ Analogs Block HGF Dimerization

Figure 24A:
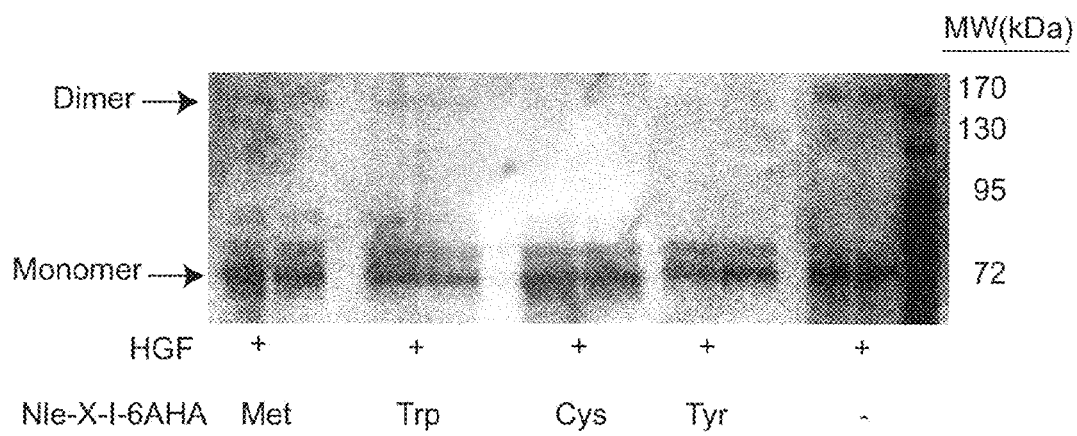
FIGS. 24A and B. Inhibition of HGF dimerization by D-Nle-X-Ile-NH—(CH$_2$)$_5$—CONH$_2$ analogs. HGF spontaneously dimerizes when incubated in PBS in the presence of heparin. HGF was incubated without (control) or with various drug candidates at 10$^{-10}$ M. These include the derivatives of D-Nle-X-Ile-(6) amino-hexanoic amide, an AngIV-based analog family, where X=Tyr, Cys, Trp, and Met. After 30 minute incubation, samples were cross-linked with BS3, separated by gel electrophoresis, and silver stained. Band density was quantified and used to determine the level of HGF dimerization in each group. Treatment groups (Tyr, Cys, Trp) were statistically different than the HGF treated group (P<0.05; N=8) (A) Representative gel. (B) Pooled and quantified data.
Figure 24B:
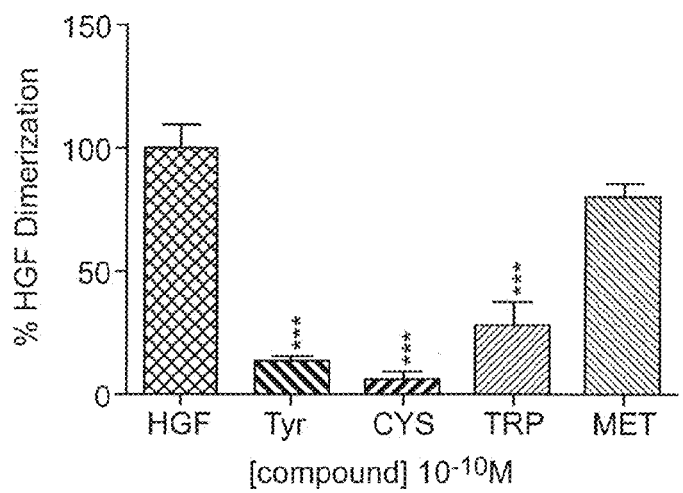
Figure 25:
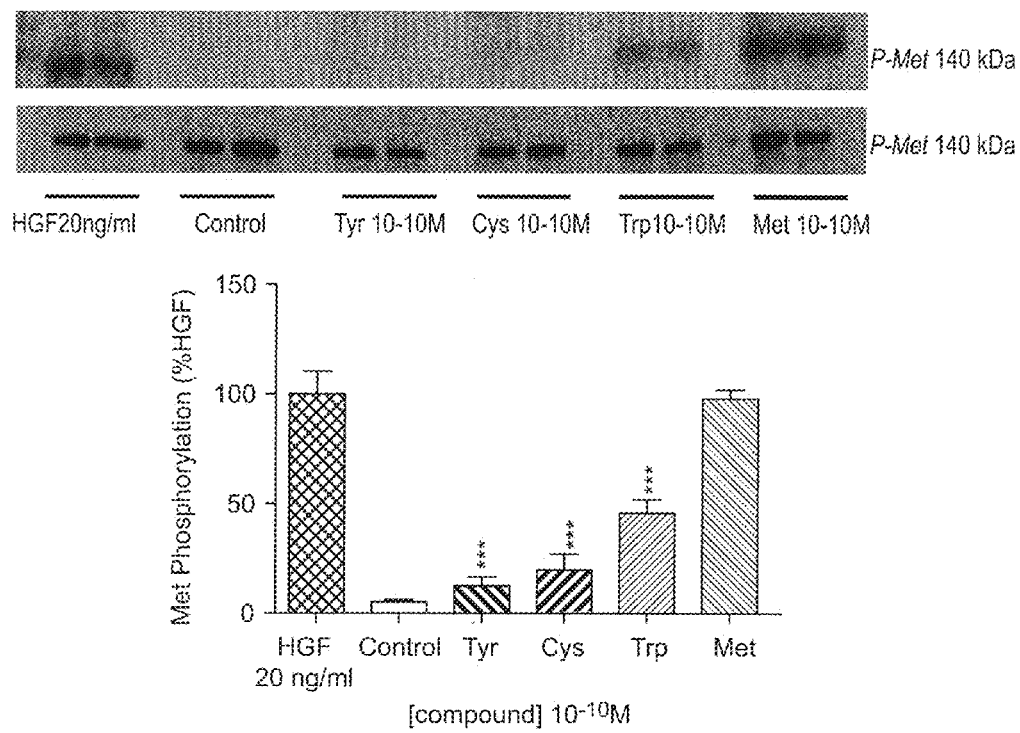
FIGS. 25A and B. Inhibition of Met phosphorylation by D-Nle-X-Ile-NH—(CH$_2$)$_5$—CONH$_2$ analogs. HEK293 cells were treated for 10 min with HGF+/−Nle-X-Ile-(6) amino-hexanoic amide analogs at the indicated concentrations. HEK293 cell lysates were immunoblotted with anti-phospho-Met and anti-Met antibodies. The differences in the mean values for Met phosphorylation among the indicated treatment groups (Nle-X-Ile-(6) amino-hexanoic amide analogs) compared to the HGF treated group were greater than would be expected by chance (P<0.05; N=6). The Met group was not different than the HGF group (P>0.05; N=6). (A) Representative gel. (B) Pooled and quantified data.
Figure 26:
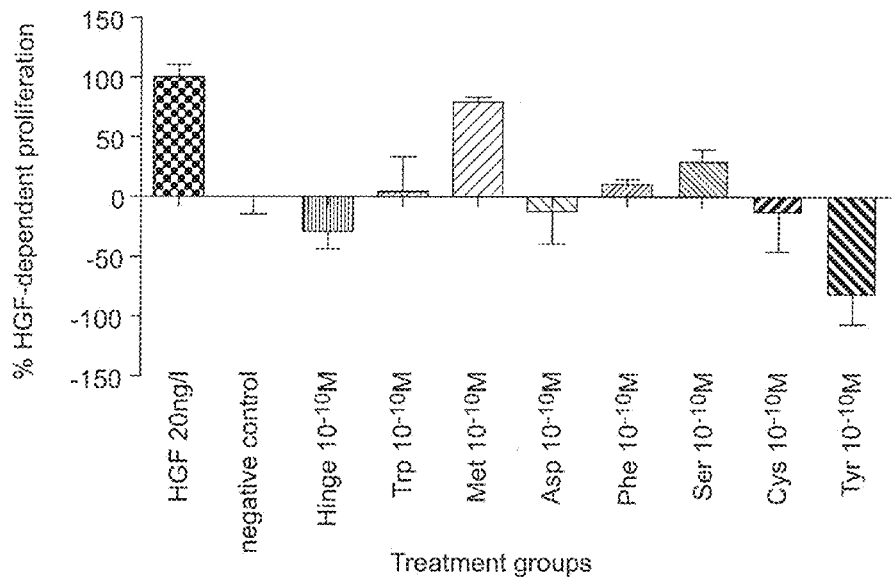
FIG. 26. Effects of D-Nle-X-Ile-NH—(CH$_2$)$_5$—CONH$_2$ analogs on MDCK cell proliferation. MDCK cells were treated with a PBS vehicle (negative control), HGF, or HGF in combination with Nle-X-Ile-(6)-amino-hexanoic amide analogs (X=L-amino acid) at 10$^{-10}$M concentration. The Hinge peptide (KDYIRN), which represents the dimerization domain of HGF, was included as a positive control. The cells were allowed to grow for 4 days. Cell numbers were estimated on the fourth day with an MTT assay by measuring absorbance at 590. % HGF-dependent proliferation: control values were subtracted from all values to determine HGF-induced increase in cell proliferation. N=6. * p<0.001.  p<0.001, * p<0.05, ns: not significant.
Figure 27B:
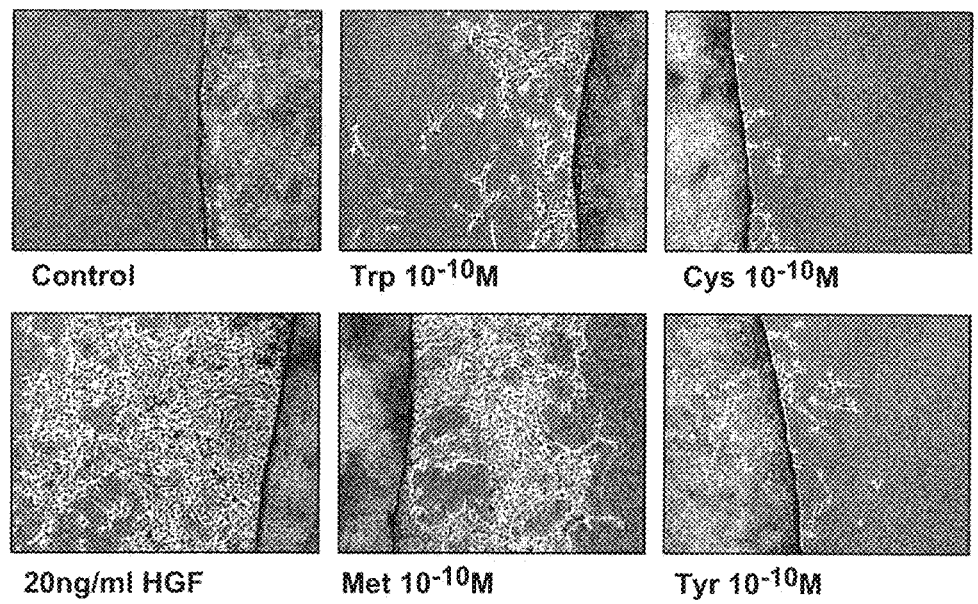
FIGS. 27A and B. Effect of D-Nle-X-Ile-NH—(CH$_2$)$_5$—CONH$_2$ analogs on HGF-dependent scattering in MDCK cells. Cell scattering in which cells lose the cell-to-cell contacts and then migrate rapidly is the classic response to HGF. MDCK cells, the gold standard cellular model for studying the HGF/Met system, were grown to 100% confluence on cover slips and then placed in a clean plate. The cells were stimulated to scatter off of the cover slip by adding 20 ng/ml of HGF to the media alone or in combination with Nle-X-Ile-(6) amino-hexanoic amide analogs (X=L-amino acid). After 48 h of scattering, the cells were fixed with methanol and stained with Diff-Quik. The coverslips were removed to reveal the ring of cells that had scattered off of the cover slip and onto the plate. (A) The effect of HGF on scattering was quantitated by determining by densitometry of the digital images from scattered cells. ANOVA analysis indicates that the Tyr+HGF, Cys+HGF, and Trp+HGF treated groups were different from the HGF alone group but not different from the control group. The HGF and HGF+Met groups were not different. N=8, p<0.05 (B) Representative pictures of MDCK cells scattering off the coverslips.

Several reports have shown that HGF needs to form homodimers and/or multimers, prior to its activation of Met (Chirgadze et al., 1999; Gherardi et al., 2006). This dimer is arranged in a head to tail orientation; the dimer interface comprises a central region, the hinge region that is important for the proper dimer formation and orientation. A homologous sequence-conservation screen against all possible transcripts that were independent of and not derived from angiotensinogen looking for similarities to AngIV identified partial homology with the hinge region of the plasminogen family of proteins, which include plasminogen itself, its anti-angiogenic degradation product, angiostatin, and the protein hormones heptocyte growth factor (HGF) and macrophage stimulating protein (MSP). Moreover, the AngIV analog Norleual, which is a potent inhibitor of the HGF/Met system, was shown to bind to HGF and block its dimerization (Kawas et al., 2011). This knowledge coupled with the demonstration that some members of the 6-AH family bound with high affinity to the hinge region of HGF led to the expectation that other active AngIV analogs, like 6-AH family members, could be expected to inhibit HGF dimerization and that the ability of an individual analog to bind HGF and inhibit HGF-dependent processes should be reflected in its capacity to attenuate dimerization. The data in FIG. 24 confirm this expectation by demonstrating that D-Nle-Cys-Ile-NH—(CH$_2$)$_5$—CONH$_2$ and D-Nle-Tyr-Ile-NH—(CH$_2$)$_5$—CONH$_2$, which bind HGF with high affinity (FIG. 23) and effectively attenuate HGF-dependent processes (FIGS. 25, 26, 27) completely block HGF dimer formation. Conversely D-Nle-Met-Ile-NH—(CH$_2$)$_5$—CONH$_2$, which has low affinity for HGF (FIG. 23) and exhibits little anti-HGF/Met activity, is unable to block dimerization at the concentration tested. The D-Nle-Trp-Ile-NH—(CH$_2$)$_5$—CONH$_2$ analog, which exhibits intermediate inhibition of dimerization, predictably has a moderate affinity for HGF and a moderate ability to inhibit HGF-dependent processes (FIGS. 25, 26, 27). Together these data confirm the expectation that active 6-AH analogs can block dimerization and further that dimerization inhibitory potential of an analog translates, at least qualitatively, to its capacity to block HGF-dependent processes.

D-Nle-X-Ile-NH—(CH$_2$)$_5$—CONH$_2$ Analogs Attenuates HGF-Dependent Met Signaling After establishing that the 6-AH family members exhibit a range of HGF binding and dimerization inhibitory profiles, we next determined whether these properties would parallel a compound's ability to inhibit Met signaling. Characteristic of tyrosine kinase-linked growth factor receptors like Met is a requisite tyrosine residue auto-phosphorylation step, which is essential for the eventual recruitment of various SH2 domain signaling proteins. Thus we evaluated the ability of several 6-AH analogs to induce Met tyrosine phosphorylation. As anticipated, the data in FIG. 25 demonstrate that both D-Nle-Cys-Ile-NH—(CH$_2$)$_5$—CONH$_2$ and D-Nle-Tyr-Ile-NH—(CH$_2$)$_5$—CONH$_2$, which bind HGF with high affinity (FIG. 23) and effectively block its dimerization (FIG. 24) were able to block Met auto-phosphorylation. The D-Nle-Trp-Ile-NH—(CH$_2$)$_5$—CONH$_2$ analog had intermediate inhibitory activity, and the D-Nle-Met-Ile-NH—(CH$_2$)$_5$—CONH$_2$ analog showed no ability to effect on Met activation. Together, these data indicate that the capacity of 6-AH analogs to inhibit HGF-dependent Met activation paralleled their HGF binding affinity and their capacity to block dimerization.

D-Nle-X-Ile-NH—(CH$_2$)$_5$—CONH$_2$ Analogs Affect HGF/Met Stimulated MDCK Cell Proliferation Met activation initiates multiple cellular responses including increased proliferation and motility, enhanced survival, and differentiation. As an initial test of the ability of 6-AH family members to alter HGF-dependent cellular activity we evaluated the capacity of several members of the family to modify the proliferative activity of Madin-Darby canine kidney (MDCK) cells, a standard cellular model for investigating the HGF/Met system (Stella and Comoglio, 1999). As seen in FIG. 26 there is a wide range of inhibitory activity against HGF dependent cellular proliferation. Similar to the results from the binding and dimerization experiments the Cys$^2$ and Tyr$^2$ analogs exhibited marked inhibitory activity. The Asp$^2$ analog, which had not been evaluated in the earlier studies, also exhibited pronounced inhibitory activity. The Trp$^2$, Phe$^2$, and Ser$^2$ analogs all showed inhibitory activity, albeit less than that observed with the most potent analogs. The decrease in HGF-dependent MDCK proliferation below control levels for some compounds is not surprising since the experiment was carried in 2% serum, which likely contains some level of HGF. The Hinge peptide (KDYIRN), which represents the dimerization domain of HGF, was included as a positive control. Studies have demonstrated that Hinge binds to HGF with high affinity blocking its dimerization and acting as a potent inhibitor of HGF-dependent cellular activities including MDCK proliferation.

D-Nle-X-Ile-NH—(CH$_2$)$_5$—CONH$_2$ Analogs Modify HGF/Met Mediated Cell Scattering in MDCK Cells Cell scattering is the hallmark effect of HGF/Met signaling; a process characterized by decreased cell adhesion, increased motility, and increased proliferation. The treatment of MDCK cells with HGF initiates a scattering response that occurs in two stages. First, the cells lose their cell-to-cell adhesion and become polarized. Second, they separate completely and migrate away from each other. It is expected that if the 6-AH family members are capable of inhibiting the HGF/Met system then they should be able to modify HGF dependent MDCK cell scattering.

Figure 28:
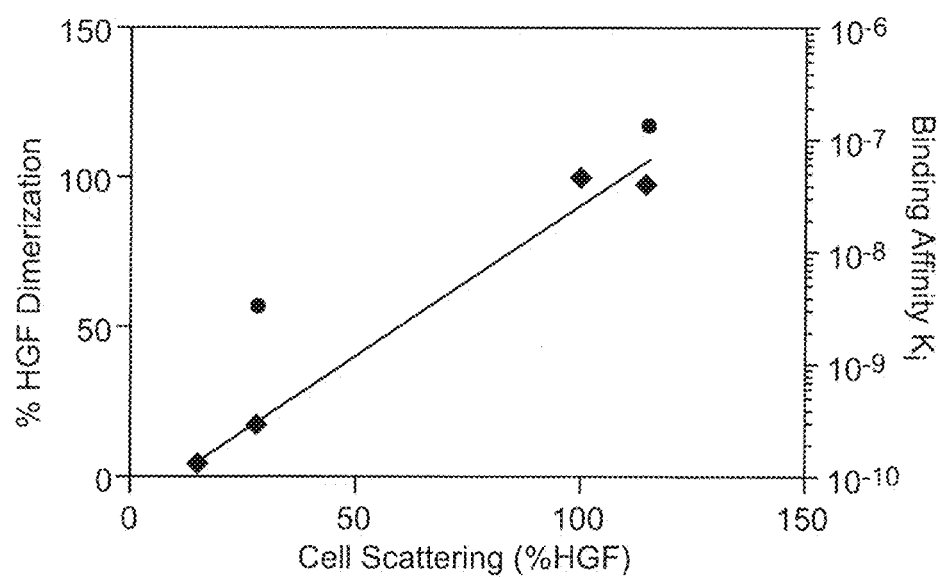
FIG. 28. Correlation between inhibition of MDCK cell scattering and interference with dimerization and the affinity to bind HGF. Three derivatives of the D-Nle-X-Ile-(6)amino-hexanoic amide, where X is: Cys, Trp, or Met were examined to determine whether the percent of inhibition of dimerization and the binding affinity for each compound for HGF could be correlated to in vitro cellular activity, namely inhibition of MDCK cell scattering. The figure shows a strong correlation between percent inhibition of HGF dimerization (◆; $R^2=0.9809$) and for binding affinity to HGF (●; K$_i$ Values; $R^2=0.9903$) and percent inhibition of HGF-dependent cell scattering.

FIGS. 27 A & B indicate that those analogs that were previously found to block HGF dimerization were effective inhibitor of HGF/Met mediated cell scattering in MDCK cells, while those analogs with poor affinity for HGF were ineffective. FIG. 28 shows a correlation between the blockade of HGF dimerization and HGF binding affinity and the ability to prevent MDCK cell scattering.

Figure 29A:
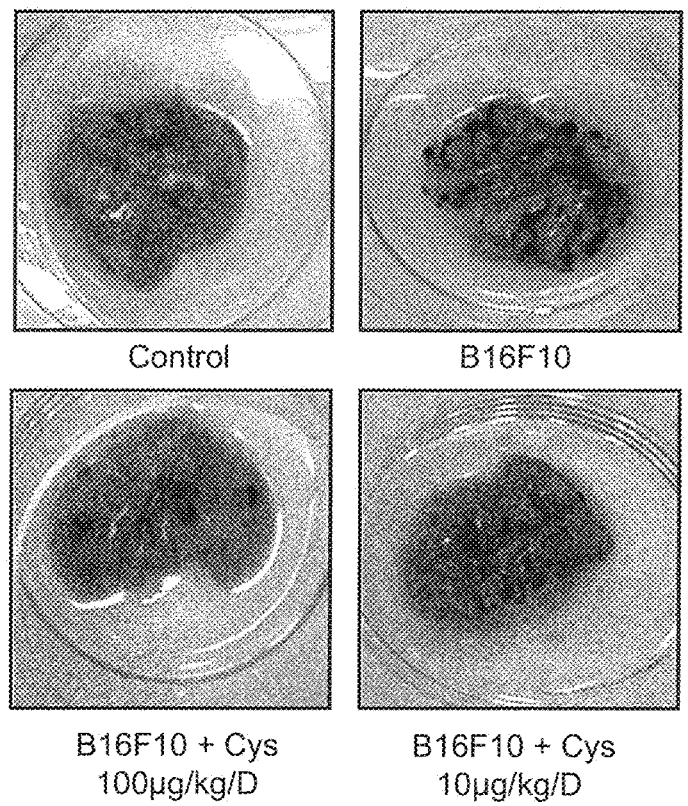
FIGS. 29A and B. Inhibition of B16-F10 melanoma lung colonization by D-Nle-Cys-Ile-NH—(CH$_2$)$_5$—CONH$_2$. 400,000 B16-F10 murine melanoma cells were injected into the tail vein of C57BL/6 mice. Mice received daily IP injections of D-Nle-Cys-Ile-(6)-amino-hexanoic amide (10 µg/kg/day or 100 µg/kg/day) or PBS vehicle. (A) After 14 days, the lungs from D-Nle-Cys-Ile-(6)-amino-hexanoic amide treated mice exhibited an obvious reduction in melanoma colonies when compared to untreated controls. (B) After removal, lungs were homogenized and total melanin content was determined spectrophotometrically and used to quantify total pulmonary melanoma colonization in vehicle treated and D-Nle-Cys-Ile-(6)-amino-hexanoic amide treated. Ungrafted age-matched control lungs exhibited a background absorbance at 410 nm. N=15, Mean±SEM; * P<0.05, *** P<0.001.
Figure 29B:
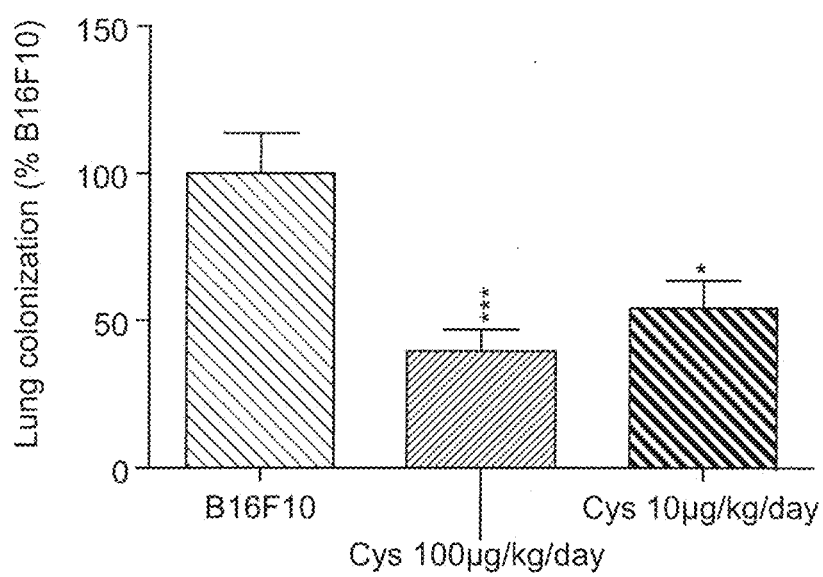

D-Nle-Cys-Ile-NH—(CH$_2$)$_5$—CONH$_2$ inhibits B16-F10 Murine Melanoma Cell Migration and Lung Colony Formation To evaluate the prospective utility of the 6-AH family members' as potential therapeutics, we examined the capacity of [D-Nle-Cys-Ile-NH—(CH$_2$)$_5$—CONH$_2$], an analog that exhibits a strong inhibitory profile against HGF-dependent Met activation, to suppress the migratory and lung colony-forming capacity of B16-F10 murine melanoma cells. B16 melanoma cells over-express Met (Ferraro et al., 2006), and were chosen for these studies because Met signaling is critical for their migration, invasion, and metastasis. As a final test for the physiological significance of the 6-AH family blockade of Met-dependent cellular outcomes, we evaluated the ability of D-Nle-Cys-Ile-NH—(CH$_2$)$_5$—CONH$_2$ to inhibit the formation of pulmonary colonies by B16-F10 cells after tail vein injection in mice. FIG. 29A illustrates the inhibitory response that was observed with daily intraperitoneal injections at two doses (10 µg/kg/day and 100 µg/kg/day) of [D-Nle-Cys-Ile-NH—(CH$_2$)$_5$—CONH$_2$]. FIG. 29B provides a quantitative assessment of pulmonary colonization by measuring melanin content, which reflects the level of melanoma colonization. Together these data demonstrate that treatment of melanoma cells with D-Nle-Cys-Ile-NH—(CH$_2$)$_5$—CONH$_2$ radically prevented lung colonization and highlight the utility of the 6-AH analogs as anti-cancer agents.

Discussion

Recently interest has grown in developing therapeutics targeting the HGF/Met system. At present this interest has been primarily driven by the realization that over-activation of the HGF/c-Met system is a common characteristic of many human cancers. The potential utility of anti-HGF/Met drugs, however, goes well beyond their use as anti-cancer agents. For example, the recognized involvement of the HGF/c-Met system in the regulation of angiogenesis (see review—supports the potential utility of HGF/Met antagonists for the treatment of disorders in which control of tissue vascularization would be clinically beneficial. These could include hyper-vascular diseases of the eye like diabetic retinopathy and the wet type of macular degeneration. In both cases anti-angiogenic therapies are currently in use. Anti-angiogenics are also being examined as treatment options in a variety of other disorders ranging from obesity where adipose tissue vascularization is targeted, to chronic liver disease, to psoriasis where topical application of anti-angiogenic drugs is being considered.

Currently the pharmaceutical industry is employing two general approaches to block Met-dependent cellular activities. The first involves the development of single-arm humanized antibodies to HGF or Met. The second approach utilizes "kinase inhibitors", which block the intracellular consequences of Met activation. These 'kinase inhibitors" are small hydrophobic molecules that work intracellularly to compete for the binding of ATP to the kinase domain of Met thus inhibiting receptor autophosphorylation. Despite the promise of the biologic and kinase-inhibitor approaches, which are currently represented in clinical trials, both have limitations arising from toxicity or specificity considerations and/or cost.

A third approach, which our laboratory has been pursuing exploits a step in the activation process of the HGF-Met system; namely the need for HGF to pre-dimerize before it is able to activate Met. Thus we have targeted the dimerization process by developing molecules that mimic the dimerization domain, the hinge region, with idea that they can act as dominant negative replacements. Recent studies have validated this general approach demonstrating that molecules designed around angiotensin IV or the hinge sequence itself can bind HGF, block its dimerization, and attenuate HGF-dependent cellular actions. The studies described herein represent a first step toward producing useful therapeutics targeted at HGF dimerization. The primary focus of this study was to improve the pharmacokinetic characteristics of a parent compound, Norleual while maintaining biological activity. To this end we successfully synthesized and evaluated a family of new molecules, the 6-AH family [D-Nle-X-Ile-NH—(CH$_2$)$_5$—COOH]. A subset of these molecules not only had improved metabolic stability and circulating $t_{1/2}$ but exhibited excellent in vitro and in vivo activity.

In addition to characterizing a new family of HGF/Met antagonists, this Example demonstrates a qualitative relationship between the ability of a compound to bind HGF and block HGF dimerization and its observed in vitro biological activity. Moreover these studies provide initial structure-activity data and pave the way for more extensive evaluation. The chemical modifications that were made at the N- and C-terminals of the AngIV molecule and the resultant improvement in metabolic stability highlight the critical role played by exopeptidases in the metabolism of AngIV-derived molecules. The demonstrated importance of protecting the terminals to pharmacokinetic characteristics suggests numerous additional synthetic approaches that may be applicable including the insertion of non-peptide linkages between the first and second amino acids, the replacement of the N-terminal amino acid with a non-α amino acid, and N-terminal acylation.

In sum, these studies further validate the notion that targeting the dimerization domain of HGF is an effective means of inhibiting the HGF/Met system. Further they demonstrate that molecules with favorable pharmacokinetic characteristics can be produced thus highlighting their clinical utility.

TABLE 5

WinNonlin ® estimated pharmacokinetic parameters for D-Nle-Tyr-Ile-NH—(CH$_2$)$_5$—CONH$_2$ after intravenous administration in adult male Sprague-Dawley rats Mean +/− SEM; n = 5. AUC$_{0-\infty}$ = area under the curve. Vd = volume of distribution. Cp$^0$ = initial concentration of drug in serum. $t_{1/2}$ = biological half-life. KE = rate of elimination. CL = clearance rate.

| Pharmacokinetic Parameter | D-Nle-Tyr-Ile-NH—(CH2)$_5$—CONH$_2$ (Mean ± SEM) |
|---|---|
| AUC0$^{-\infty}$ (min · ng/mL) | 692.5 ± 293.2 |
| Vd (L/kg) | 104186.8 ± 65034.3 |
| Cp$^0$ (ng/mL) | 68.2 ± 32.2 |
| t½ (min) | 1012.0 ± 391.4 |
| KE (min−1) | 0.001 ± 0.0002 |
| CL (L/min/kg) | 58.3 ± 15.6 |

TABLE 6

Predicted physiochemical properties of
D-Nle-Tyr-Ile-NH—(CH$_2$)$_5$—CONH$_2$. The physiochemical
properties of D-Nle-Tyr-Ile-NH—(CH$_2$)$_5$—CONH$_2$ were
estimated following modeling with ADMET Predictor ® software.
LogP is the octanol:water partitioning coefficient. P$_{eff}$ is the predicted
effective human jejunal permeability. P$_{avg}$ is the approximate
average intestinal permeability along the entire human intestinal tract.
Pr$_{Unbnd}$ is the percent unbound to plasma proteins.

| Physicochemical Property | Predicted Value |
| --- | --- |
| logP | 1.45 |
| Peff | 1.53 |
| Pavg | 0.39 |
| PrUnbnd | 42.68 |

REFERENCES FOR EXAMPLES 1-3

De Bundel, D., H. Demaegdt, et al. (2010) "Involvement of the AT1 receptor subtype in the effects of angiotensin IV and LVV-haemorphin 7 on hippocampal neurotransmitter levels and spatial working memory." J Neurochem 112(5): 1223-34

El-Husseini, A. E., E. Schnell, et al. (2000). "PSD-95 involvement in maturation of excitatory synapses." Science 290 (5495): 1364-8.

Fisher, A., Z. Pittel, et al. (2003). "M1 muscarinic agonists can modulate some of the hallmarks in Alzheimer's disease: implications in future therapy." J Mol Neurosci 20(3): 349-56.

Han, K. and E. Kim (2008). "Synaptic adhesion molecules and PSD-95." Prog Neurobiol 84(3): 263-83.

Hering, H. and M. Sheng (2001). "Dendritic spines: structure, dynamics and regulation." Nat Rev Neurosci 2(12): 880-8.

Kasai, H., M. Fukuda, et al. (2001)"Structural dynamics of dendritic spines in memory and cognition." Trends Neurosci 33(3): 121-9.

Kennedy, M. B. (1997). "The postsynaptic density at glutamatergic synapses." Trends Neurosci 20(6): 264-8.

Meighan, S. E., P. C. Meighan, et al. (2006). "Effects of extracellular matrix-degrading proteases matrix metalloproteinases 3 and 9 on spatial learning and synaptic plasticity." J Neurochem 96(5): 1227-41.

Meijering, E., M. Jacob, et al. (2004). "Design and validation of a tool for neurite tracing and analysis in fluorescence microscopy images." Cytometry A 58(2): 167-76.

Wayman, G. A., M. Davare, et al. (2008). "An activity-regulated microRNA controls dendritic plasticity by down-regulating p250GAP." Proc Natl Acad Sci USA 105(26): 9093-8

Wayman, G. A., S. Impey, et al. (2006). "Activity-dependent dendritic arborization mediated by CaM-kinase I activation and enhanced CREB-dependent transcription of Wnt-2." Neuron 50(6): 897-909.

Wright, J. W., L. Stubley, et al. (1999). "Contributions of the brain angiotensin IV-AT4 receptor subtype system to spatial learning." J Neurosci 19(10): 3952-61.

Wright, J. W. and J. W. Harding (1985) "The brain RAS and Alzheimer's disease." Exp Neurol 223(2): 326-33.

Yasumatsu, N., M. Matsuzaki, et al. (2008). "Principles of long-term dynamics of dendritic spines." J Neurosci 28(50): 13592-608.keep

Example 4

Evaluation of Metabolically Stabilized Angiotensin IV Analogs as Agents to Treat Dementia The results of the study described in this example indicate that N-terminal modifications, and to a lesser extent C-terminal modifications, could improve the metabolic stability of Nle$^1$-AngIV-derived tri- and tetra-peptides while preserving activities that are relevant to the treatment of dementia. Expanding on these data, additional modifications intended to increase hydrophobicity and decrease hydrogen bonding potential yielded N-hexanoic-Tyr-Ile-(6)-aminohexanoic amide (dihexa), a potent cognitive enhancing molecule that proved to be very stable, to be capable of inducing spinogenesis/synaptogenesis at picomolar concentrations, is slowly cleared from the blood compartment, and is sufficiently BBB permeable.

Methods

Compounds and Peptide Synthesis.

Scopolamine hydrobromide (#S-1875) was purchased from Sigma Chemical (St Louis, Mo.). The peptides were synthesized using Fmoc-based solid-phase peptide synthesis methods and purified by reverse phase HPLC in the Harding laboratory. Purity and structure were verified by LC-MS.

Serum Metabolism of Peptides.

Chemicals and Reagents.

HPLC grade acetonitrile (ACN), acetic acid and water, and reagent grade trifluoroacetic acid (TFA) were purchased from Sigma/Aldrich (St Louis, Mo.). Norleucine-YIHPF (Nle$^1$-Ang-IV), D-Nle-YI, Acetyl-NleYIH, Gamma Amino Butyric Acid-YIH, NleYI-amide, N-hexanoic-YI-(6) aminohexanoic amide (dihexa) were synthesized by Fmoc based solid phase methods in the Harding laboratory.

Animals and Serum Preparation.

Four month old male Sprague Dawley rats were used as the blood source for the metabolism studies. Blood was collected from left/right jugular veins of the rats using sterile catheters. After a 30 minute incubation on ice, the blood was centrifuged at 1000 rpm for 15 min to separate the serum. Serum was then transferred to clean tubes and stored at −20° C. until use.

Drug Solution Preparation.

Except for dihexa all drug solutions were prepared in HPLC grade water at 5 mg/ml. Stock drugs were kept in powder form and stored at −20° C. Serum metabolism experimental procedure and analysis. Rat blood serum samples were pre-equilibrated at 37° C. and then 10 μL (50 μg) of each drug solution was added to 90 μL of rat serum in 1.5 mL Eppendorf tube maintained at 37° C. At specified time intervals, metabolism was terminated by precipitating proteins with the addition of 1 ml of a solution of acetonitrile (ACN) and acetic acid (9:1, v/v). The terminated reaction mixture was stored in refrigerator (5° C.) overnight and centrifuged (14,000 rpm) for 30 min to remove precipitated proteins. The separated supernatant was dried in vacuum concentrator. The dried samples were reconstituted using 200 μL HPLC mobile phase (10% v/v ACN in water), vortexed briefly, and subjected to HPLC separation and analysis. A serum blank experiment to detect any interfering peaks in the HPLC chromatogram was performed by in an identical manner except that no drug was added. Zero time values for each drug candidate were established by first treating the serum with ACN, processing the sample as described above, adding drug, and then performing HPLC analysis.

The degradation rate of drug was determined by measuring the decrease in area under curve (AUC) at the retention time of drug over time. The AUC obtained from the zero time experiment was considered to represent the "100%" drug concentration and was used to determine the decreased drug concentration at each specified time interval. The semi-logarithmic plot of drug concentration vs. time was generated to determine degradation kinetic constant (k) of the tested drug. The half-life of drug was ($t_{1/2}$) was calculated by 0.693/k.

Apparatus and Chromatographic Conditions.

Analysis of samples was performed using an HPLC system. The system consisted of a communications bus module, pumps, and a photodiode array detector. Data collection and integration were achieved using suitable software. Separation was achieved using a C18 (250 mm×4.6 mm id., 5 µm particle size) reverse phase column. The column temperature was set at 40° C. The mobile phase consisted of a mixture of ACN and water with 0.1% TFA and was degassed by ultrasonication. Samples were introduced by manual mode with an injection volume of 250 µL. The drug was eluted with a flow rate of 1 mL/min and detected by PDA detector at excitation wavelengths of 215 and 280 nm.

Pharmacokinetics.
Animals and Surgical Procedures.

Male Sprague-Dawley rats (250+ g) were obtained from Harlan Laboratories (CA, USA) and allowed food (Harlan Teklad rodent diet) and water ad libitum in our animal facility. Ethics approval for animal experimentation was obtained from Washington State University. Rats were housed in temperature-controlled rooms with a 12 hour light/dark cycle. The right jugular veins of the rats were catheterized with sterile polyurethane catheters under ketamine (100 mg/kg im, Fort Dodge Animal Health, Fort Dodge, Iowa, USA) and isoflurane anesthesia. The catheters were exteriorized through the dorsal skin and flushed with heparinized saline before and after blood sample collection and filled with heparin-glycerol locking solution (6 mL glycerol, 3 mL saline, 0.5 mL gentamycin (100 mg/mL), 0.5 mL heparin (10,000 u/mL)) when not sampled for more than 8 hours.

Blood Sample Preparation.

Fresh rat blood was obtained prior to each experiment via jugular vein catheters from adult male Sprague-Dawley rats.

Dihexa solutions were prepared by suspending dry stock dihexa in DMSO at 1 mg/mL and subsequent serial dilutions in 50% DMSO or HPLC grade water for the final concentrations specified. Stock dihexa is kept in powder form and stored at −20° C. Quality control (QC) samples were prepared by spiking fresh rat plasma with an appropriate dilution of dihexa for the final concentration of dihexa specified, keeping a 10:1 ratio of plasma to dihexa solution (final DMSO concentration 5%). The compounds, $Nle^1$-Ang-IV and Nle-YI-(6) aminohexanoic amide, molecules very similar in structure and properties to dihexa, were used as internal standards and were prepared the same way.

The proteins present in the plasma samples were precipitated using three volumes of ice-cold acetonitrile. Internal standards were then added and the samples were vortexed for approximately 10 seconds. Samples were then centrifuged at 5000 RPM for 5 minutes. The supernatants were transferred to new tubes and stored until use at −20° C. Samples were then concentrated to a volume of approximately 100 ul. 200 ul HPLC grade water was added to each sample and the samples were transferred to autosampler vials.

Pharmacokinetic Study.

Male Sprague Dawley rats were catheterized as described in the Animals and Surgical Procedures section. Animals were placed in metabolic cages prior to the start of the study and time zero blood and urine samples were collected. The animals were then dosed intravenously via the jugular vein catheters or intraperitoneally with dihexa dissolved in 75% DMSO. The typical injection volume was 200 µL yielding an initial estimated DMSO concentration in blood of 0.46%. After dosing, blood samples were collected as described in Table 7.

TABLE 7

Blood collection schedule following intravenous and intraperitoneal administration of dihexa.

| Dosage Route | Dose | Blood Sample Volume | Sample Collection Times (minutes unless otherwise noted) |
|---|---|---|---|
| Intravenous | 10 mg/kg | 200 µL | 0, 10, 30, 90, 150, 240, 330, 420, 510, 600, 690, 780, 24 hours, 48 hours, 5 days |
| Intraperitoneal | 20 mg/kg | 200 µL | 0, 10, 30, 60, 90, 120, 150, 180, 240, 300, 360, 420, 480, 600, 720, 24 hours, 48 hours, 5 days |

After each blood sample was taken, the catheter was flushed with heparinized lactated Ringer's solution and a volume of heparinized lactated Ringer's equal to the volume of blood taken was injected (to maintain total blood volume).

The blood samples were collected into polypropylene microcentrifuge tubes and cooled on ice for not more than 1 hour. The samples were centrifuged at 5000 RPM for 7 minutes and 80 µL plasma were transferred into previously prepared tubes containing 240 µL ice-cold acetonitrile. The samples were vortexed vigorously for 30 seconds and held on ice. 100 µg/mL Nle-YI-(6) aminohexanoic amide in 10 µL was used as an internal standard and added to each sample on ice. Samples were held on ice until the end of the experiment and stored at −20° C. afterward until further processing.

Serial dilutions of dihexa in 50% DMSO or water (for dilutions of 50 µg/mL or less) were prepared from the stock used to dose the animals to be used for preparation of a standard curve. 10 µL of each serial dilution was then added to 90 µL of blank plasma for final concentrations of 0.01, 0.02, 0.05, 0.1, 0.2, 1, 10, 20, 50 and 100 µg/mL. 80 µL of each plasma sample was transferred to previously prepared tubes containing 240 µL ice-cold acetonitrile and vortexed vigorously. 10 µL containing 100 µg/mL Nle-YI-(6) aminohexanoic amide as an internal standard, was added to each sample on ice. The standard curve plasma samples were then stored at −20° C. and further processed alongside the pharmacokinetic study samples according to the method described above.

Chromatographic System and Conditions.

The HPLC/MS system that was employed consisted of a communications bus module, pumps, an auto sampler, a diode array detector and a mass spectrometer. Data collection and integration were achieved using suitable solution software.

The analytical column that was used was n C18 (100 mm×2.1 mm). The mobile phase consisted of HPLC grade acetonitrile and water with 0.1% acetic acid. For plasma samples, separation was carried out using a non-isocratic method, starting at 23% ACN and climbing to 31% ACN over 9 minutes, at ambient temperature and a flow rate of 0.3 mL/min. For MS analysis, a positive ion mode (SIM) was used to monitor the m/z of dihexa at 527 nm (dihexa with the addition of a sodium adduct) and the m/z of Nle-YI-(6) aminohexanoic amide and $Nle^1$-AngIV (internal standards) at 513 and 541, respectively (both with sodium adducts). Samples were introduced using the autosampler and the injection volume was 50 ul. For the microsomal study, the m/z of verapamil was 455, the m/z of piroxicam was 332, and the m/z of 7-ethoxycoumarin was 191.

Pharmacokinetic Analysis

Pharmacokinetic analysis was performed using data from individual rats from which the mean and standard error of the mean (SEM) were calculated for each group. Noncompartmental pharmacokinetic parameters were calculated from plasma drug concentration-time profiles by use of WinNonlin® software (Pharsight, Mountain View, Calif., USA). The following relevant parameters were determined where possible: area under the concentration-time curve from time zero to the last time point ($AUC_{0-last}$) or extrapolated to infinity ($AUC_{0-\infty}$), $C_{max}$ concentration in plasma extrapolated to time zero ($C_0$), terminal elimination half-life ($t_{1/2}$), volume of distribution (Vd), and clearance (CL).

Blood-Brain Barrier Penetrability Study

To evaluate the of ability dihexa to penetrate the BBB and accumulate in the brain rats were fitted with carotid cannulas and infused with 10 μCi of $^3$H-dihexa and 2 μCi of $^{14}$C inulin, a vascular space marker, in 100 μL of isotonic saline. Thirty minutes after infusion, brains were removed and dissected and blood samples taken. After solubilization, $^3$H and $^{14}$C were quantified by dual window scintillation counting to determine the amount of dihexa and inulin in brain and blood samples. The ratio of dihexa/inulin in blood was then used to account for any blood contamination in the various brain regions.

Microsomal Metabolism

Male rat liver microsomes were obtained from Celsis (Baltimore, Md., USA). The protocol from Celsis for microsome-drug incubation was followed with minor adaptations. An NADPH regenerating system (NRS) was prepared as follows: 1.7 mg/mL NADP, 7.8 mg/mL glucose-6-phosphate and 6 units/mL glucose-6-phosphate dehydrogenase were added to 10 mL 2% sodium bicarbonate. The NRS was used immediately. 500 μM solutions of dihexa, piroxicam, verapamil and 7-ethoxycoumarin (low, moderate and highly metabolized controls, respectively) were prepared in acetonitrile. Microsomes were suspended in 0.1M Tris buffer (pH 7.38) at 0.5 mg/mL. 100 μL microsomes were added to pre-chilled microcentrifuge tubes on ice. To each sample, 640 μL 0.1M Tris buffer and 10 μL of 500 μM test compound were added. The samples and NRS were placed in a water bath at 37° C. for 5 minutes. Samples were removed from the water bath, 250 μL NRS was added, and each was placed into a rotisserie hybridization oven at 37° C. with rotation at high speed for the appropriate incubation time (10, 20, 30 40 or 60 minutes). 500 μL from each sample was transferred to each of two tubes containing 500 μL ice-cold acetonitrile with internal standard per incubation sample. Standard curve samples were prepared in incubation buffer and 500 μL was added to 500 μL of ice-cold acetonitrile with internal standard. All samples were then analyzed by high performance liquid chromatography/mass spectrometry. Drug concentrations were determined and loss of parent relative to negative control samples containing no microsomes was calculated. Clearance was determined by nonlinear regression analysis for $k_e$ and $t_{1/2}$ and the equation $Cl_{int}=k_e Vd$.

Behavioral Studies

Animals and Surgery.

Male Sprague-Dawley rats (Taconic derived) weighing 390-450 g were maintained with free access to water and food (Harland Tekland F6 rodent diet, Madison, Wis.) except the night prior to surgery when food was removed were used for most studies. The aged rat study employed 24 month old rats of mixed sex. For the scopolamine studies each animal was anesthetized with Ketamine hydrochloride plus Xylazine (100 and 2 mg/kg im. respectively; Phoenix Scientific; St. Joseph, Mo., and Moby; Shawnee, Kans.). When required an intracerebroventricular (icv) guide cannula was stereotaxically positioned in the right hemisphere using flat skull coordinates 1.0 mm posterior and 1.5 mm lateral to bregma (refer to Wright et al. 1985). The guide cannula measured 2.5 cm in overall length and was prepared with a heat bulge placed 2.5 mm from its beveled tip, thus acting as a stop to control the depth of penetration at 2.5 mm. Once in position, the cannula was secured to the skull with two stainless-steel screws and dental cement. The guide was then sealed with a thick stainless steel wire. Post-operatively the animals were housed individually in an American Accreditation for Laboratory Animal Care-approved vivarium maintained at 22±1° C. on a 12-h alternating light/dark cycle initiated at 06:00 h. All animals were hand gentled for 5 min per day during the 5-6 days of post-surgical recovery. Histological verification of cannula placement was accomplished by the injection of 5 μl fast-green dye via the guide cannula following the completion of behavioral testing. Correct cannula placement was evident in all rats utilized in this study.

Water Maze Testing.

The water maze consisted of a circular tank painted black (diameter: 1.6 m; height: 0.6 m), filled to a depth of 26 cm with 26-28° C. water. A black circular platform (diameter: 12 cm; height: 24 cm) was placed 30 cm from the wall and submerged 2 cm below the water surface. The maze was operationally sectioned into four equal quadrants designated NW, NE, SW, and SE. For each rat the location of the platform was randomly assigned to one of the quadrants and remained fixed throughout the duration of training. Entry points were at the quadrant corners (i.e. N, S, E, and W) and were pseudo-randomly assigned such that each trial began at a different entry point than the preceding trial. Three of the four testing room walls were covered with extra-maze spatial cues consisting of different shapes (circles, squares, triangles) and colors. The swimming path of the animals was recorded using a computerized video tracking system. The computer displayed total swim latency and swim distance. Swim speed was determined from these values.

Each member of the treatment groups received an icv injection of scopolamine hydrobromide (70 nmol in 2 μl aCSF over a duration of 20 s) 20 min prior to testing followed by Nle$^1$-AngIV or one of the analogs (in 2 μl aCSF) 5 min prior to testing. Control groups received scopolamine or aCSF 20 min prior to testing followed by aCSF 5 min prior testing. The behavioral testing protocol has been described previously in detail (Wright et al. 1999). Briefly, acquisition trials were conducted on 8 consecutive days with 5 trials/day. On the first day of training the animal was placed on the platform for 30 s prior to the first trial. Trials commenced with the placement of the rat facing the wall of the maze at one of the assigned entry points. The rat was allowed a maximum of 120 s to locate the platform. Once the animal located the platform it was permitted a 30 s rest period on the platform. If the rat did not find the platform, the experimenter placed the animal on the platform for the 30 s rest period. The next trial commenced immediately following the rest period.

On the day following acquisition training (day 9), one additional trial was conducted during which the platform was removed (probe trial). The animal was required to swim the entire 120 s to determine the persistence of the learned response. Total time spent within the target quadrant where the platform had been located during acquisition and the number of crossings of that quadrant was recorded. Upon completion of each daily set of trials the animal was towel-dried and placed under a 100 watt lamp for 10-15 min and then returned to its home cage.

Dendritic Spine Analysis.

Hippocampal Cell Culture Preparation.

Hippocampal neurons ($2\times10^5$ cells per square cm) were cultured from P1 Sprague Dawley rats on plates coated with poly-L-lysine from Sigma (St. Louis, Mo.; molecular weight –300,000). Hippocampal neurons were maintained in Neurobasal® A media from Invitrogen (Carlsbad, Calif.) supplemented with B27 from Invitrogen, 0.5 mM L-glutamine, and 5 mM cytosine-D-arabinofuranoside from Sigma added at 2 days in vitro. Hippocampal neurons were then cultured a further 3-7 days, at which time they were either transfected or treated with various pharmacological reagents as described in (Wayman et al., 2008).

Transfection.

Neurons were transfected with mRFP-β-actin on day in vitro 6 (DIV6) using LipofectAMINE 2000 (Invitrogen) according to the manufacturer's protocol. This protocol yielded the desired 3-5% transfection efficiency thus enabling the visualization of individual neurons. Higher efficiencies obscured the dendritic arbor of individual neurons. Expression of fluorescently tagged actin allowed clear visualization of dendritic spines, as dendritic spines are enriched in actin. On DIV7 the cells were treated with vehicle ($H_2O$) or peptides (as described in the text) added to media. On DIV12 the neurons were fixed (4% paraformaldehyde, 3% sucrose, 60 mM PIPES, 25 mM HEPES, 5 mM EGTA, 1 mM $MgCl_2$, pH 7.4) for 20 min at room temperature and mounted.

Slides were dried for at least 20 hours at 4° C. and fluorescent images were obtained with an inverted confocal microscope with a 60× oil immersion lens, NA 1.4 and resolution 0.280 μm. Dendritic spine density was measured on primary and secondary dendrites at a distance of at least 150 μm from the soma. Five 50 μm long segments of dendrites from at least 10 neurons were analyzed for each data point reported. Each experiment was repeated at least three times using independent culture preparations. Dendrite length was determined using the National Institutes of Health's Image J 1.41o program (NIH, Bethesda, Md.) and the neurite tracing program Neuron J (Meijering et al., 2004) Spines were manually counted.

Organotypic Hippocampal Slice Culture Preparation and Transfection.

Hippocampi from P4 Sprague Dawley rats were cultured as previously described (Wayman, Impey et al. 2006). In order to visualize dendritic arbors 400 μm hippocampal slices from postnatal day 5 were cultured for 3 days after which they were biolistically transfected with tomato fluorescent protein (TFP) using a Helios Gen Gun (BioRad, Hercules, Calif.), according to the manufacturer's protocol. Following a 24 hour recovery period slices were stimulated with vehicle ($H_2O$), 1 pM $Nle^1$-AngIV or dihexa for 2 days. Slices were fixed and mounted. Hippocampal CA1 neuronal processes were imaged and measured as described above.

Immunocytochemistry.

Transfected neurons were treated and fixed as described above. Following fixation, cells were rinsed in PBS and permeabilized with 0.1% Triton® X-100 detergent (Bin-Rad; Hercules, Calif.), followed by two rinses in PBS and blocked with 8% bovine serum albumin (Intergen Company; Burlington, Mass.) in PBS for 1 h. Cells were again rinsed with PBS, followed by a 24 hour incubation period with anti-α-VGLUT1 (Synaptic Systems; Goettingen, Germany), anti-synapsin (Synaptic Systems; Goettingen, Germany), anti-PSD-95 (Milipore, Billerica, Mass.) following the manufacturers protocol, at 4° C. Subsequently cells were rinsed twice with PBS, incubated in labeled goat-anti-mouse antibody following the manufacturer's protocol for two hours at room temperature, rinsed again with PBS, and mounted with an anti-fade reagent. Imaging and analysis were performed as described above.

Whole-Cell Recordings.

Patch-clamp experiments were performed on mRFP-β-actin transfected cultured hippocampal neurons with PBS (vehicle control) or 1 pM $Nle^1$-AngIV pretreatment, and recorded. The culture medium was exchanged by an extracellular solution containing (in mM) 140 NaCl, 2.5 KCl, 1 $MgCl_2$, 3 $CaCl_2$, 25 glucose, and 5 HEPES; pH was adjusted to 7.3 with KOH; and osmolality was adjusted to 310 mOsm. Cultures were allowed to equilibrate in a recording chamber mounted on inverted microscope for 30 min. before recording. Transfected cells were visualized with fluorescence (Olympus optical). Recording pipettes were pulled from standard-wall borosilicate glass without filament (OD=1.5 mm; Sutter Instrument). The pipette-to-bath DC resistance of patch electrodes ranged from 4.0 to 5.2 MΩ, the internal solution being the following composition (in mM): 25 CsCl, 100 $CsCH_3O_3S$, 10 phosphocreatine, 0.4 EGTA, 10 HEPES, 2 $MgCl_2$, 0.4 Mg-ATP, and 0.04 Na-GTP; pH was adjusted to 7.2 with CsOH; osmolality was adjusted to 296-300 mOsm. Miniature EPSCs (mEPSCs) were isolated pharmacologically by blocking GABA receptor chloride channels with picrotoxin (100 μM; Sigma), blocking glycine receptors with strychnine (1 μM; Sigma), and blocking action potential generation with tetrodotoxin (TTX, 500 nM; R&D Systems, Minneapolis, Minn.). Recordings were obtained. Analog signals were low-pass Bessel filtered at 2 kHz, digitized at 10 kHz through a digital interface, and stored in a computer using suitable software. The membrane potential was held at –70 mV at room temperature (25° C.) during a period of 0.5-2 h after removal of the culture from the incubator. Liquid junction potentials were not corrected. Data analysis was performed using suitable software. The criteria for a successful recording included an electrical resistance of the seal between the outside surface of the recording pipette and the attached cell >2 GΩ and a neuron input resistance >240 MΩ. The mEPSCs had a 5-min recording time.

Statistical Analyses

The Morris water maze data sets, consisting of mean latencies and path distances to find the platform during each daily block of five trials, were calculated for each animal for each day of acquisition. One-way ANOVAs were used to compare group swim latencies on Days 1, 4, and 8 of training. Past experience with this task has indicated these days to be representative of overall performance. Data collected during the probe trials (time spent in the target quadrant and entries into the target quadrant) were also analyzed using one-way ANOVAs. Significant effects were further analyzed by a Newman-Keuls post-hoc test with a level of significance set at $p<0.05$. Because of variability in the non-treated aged rat group a non-parametric Mann-Whitney U test was performed to evaluate significance.

One-way ANOVA was used to analyze the dendritic spine results and significant effects were analyzed by Tukey post-hoc test. Linear regression analysis was used to determine the correlation between spine characteristics and latency to find the platform in the water maze task. Multiple comparisons of electrophysiological results were made using a one-way ANOVA followed by a Newman-Keuls post-hoc test with a level of significance set at $p<0.05$. Numerical data are expressed as mean SEM.

Results

N- and C-terminal Modifications of Nle¹-AngIV-Derived Peptides Exhibit Improved Stability in Rat Serum

Development of a metabolically stable, BBB permeable Nle$^1$-AngIV-derived molecule with pro-cognitive activity the introduction of several structural changes directed at the N-terminal including: the substitution of D-norleucine for L-norleucine; the N-acetylation of norleucine; and the replacement of norleucine with a non-α-amino acid γ-aminobutyric acid (GABA).

To evaluate the effect of these structural changes on general metabolic stability the compounds were incubated in the presence of rat serum and the resultant incubates analyzed for metabolism by HPLC. The results of this study, which are shown in Table 8, indicate that as expected Nle$^1$-AngIV had an exceedingly short half-life of less than two minutes; while each of the N-terminal modified peptides exhibited markedly elongated half-lives. A more modest increase in stability was noted following C-terminal amidation. These data confirm the importance of attenuating N-terminal dependent degradation, if one desires to improve the metabolic stability of Nle$^1$-AngIV-derived peptides. Thus, the incorporation of these types of modifications or the introduction of non-peptide bonds (Krebs et al., 1996) may provide a workable strategy to improve the bioavailability of Nle$^1$-AngIV-derived peptides and peptidomimetics.

TABLE 8

Serum Stability of AngIV Analogs

| Compound | Half-Life (min) |
| --- | --- |
| Nle1-AngIV | 1.42 +/− .26 |
| N-acetyl-Nle-Tyr-Ile-His | 115 +/− 7.6 |
| D-Nle-Tyr-Ile | 225 +/− 23.7 |
| GABA-Tyr-Ile | 946 +/− 234 |
| Nle-Tyr-Ile-His-NH2 | 23.0 +/− 3.1 |
| Dihexa | 335.5 +/− 9.5 |

Mean +/− SD, N = 3

N- and C-Terminal Modified Nle¹-AngIV Analogs Retain Pro-Cognitive Activity.

While N-terminal modification of Nle$^1$-AngIV-derived tri- and tetra-peptides significantly increased their stability in rat serum the true test of success of these structural modifications is whether the molecules still possess pro-cognitive activity. To gauge the pro-cognitive potential of the molecules we evaluated their capacity to reverse scopolamine-dependent learning deficits following their acute ICV application as assessed by performance in the Morris water maze. The scopolamine preparation that was employed is a widely accepted animal model of the spatial memory dysfunction and produces deficits reminiscent of those observed in early to middle stage Alzheimer's disease patients (Fisher et al., 2003).

Figure 30A:
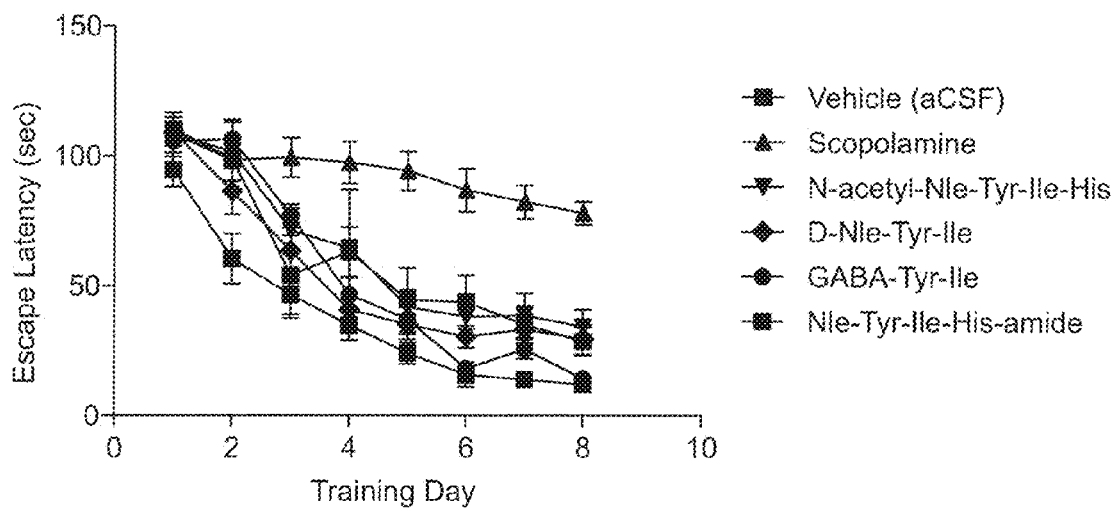
FIGS. 30A and B. Metabolically stabilized AngIV analogs reverse scopolamine-dependent spatial learning deficits. A. Group latencies to find the submerged platform in the Morris water maze task of spatial memory. Data from six groups of rats (N=8 each) that were pretreated with icv scopolamine (70 nmol in 2 µl aCSF) 20 min prior to training followed by the icv infusion of the designated analog (1 nmol in 2 µl aCSF) 5 min prior to daily training are shown. A two-way ANOVA with repeated measures indicated that all groups were different from the scopolamine▶ aCSF on at the last five days of testing. Mean±SEM; *p<0.001. B. Day 9 probe trials by each experimental group. Time spent in the target quadrant was recorded for each experimental group. All treatment groups were different from the scopolamine▶ aCSF group (p<0.01) but not significantly different from the vehicle group (p>0.05). The GABA-Tyr-Ile group was also different than all the other treated groups (*p<0.05). aCSF=artificial cerebrospinal fluid.

As an initial measure of cognitive function, the escape latency to locate the submerged pedestal in a Morris water maze was recorded over an eight day observation period. As can be seen in FIG. 30A, scopolamine application significantly retarded task acquisition when compared to vehicle controls. Tandem application of scopolamine with each of the N- and C-terminal modified peptides significantly improved water maze performance when compared to the scopolamine treated group. Although there were no differences among the groups on Day 1 of training, all the compound treated groups showed improved performance by Day 3 ($p<0.001$). This improved performance was maintained throughout the testing period and post-hoc analyses on Day 8 continued that all had improved performance when compared to the scopolamine/deficit group ($p<0.0001$). On day 8 animals treated with the GABA-Tyr-Ile exhibited the best performance among the compound treated groups, had a significantly lower mean latency to find the platform than the other three treated groups ($p<0.001$), which did not differ from one another ($p>0.05$), and was not significantly different than the vehicle control group ($p>0.05$).

Figure 30B:
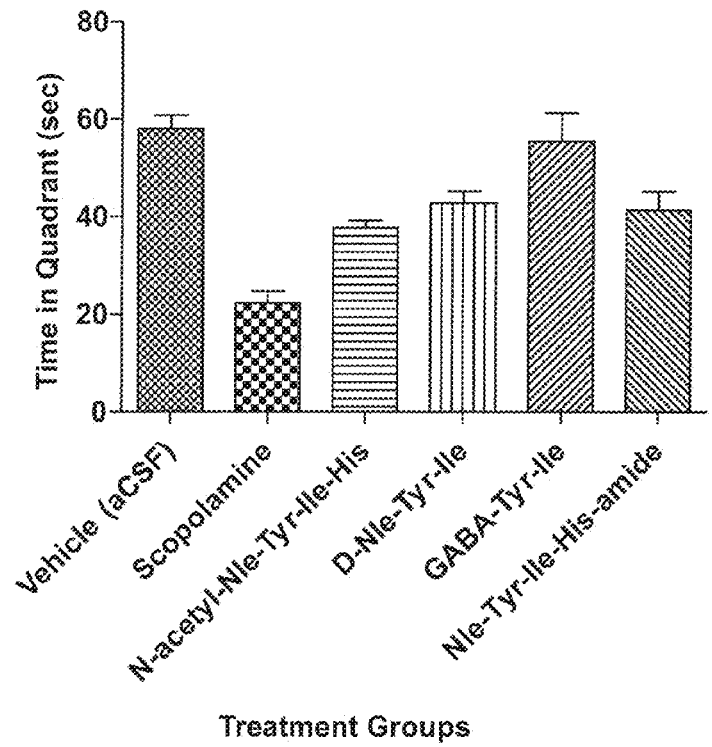
Figure 31B:
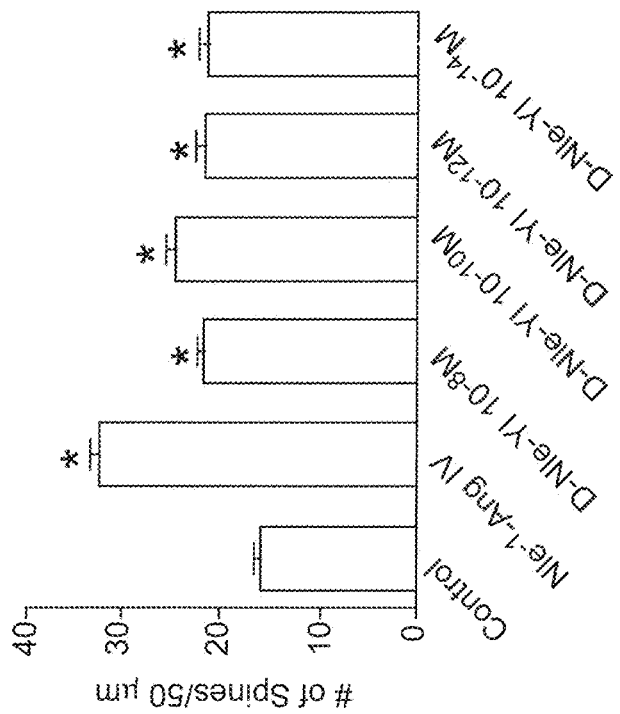
FIG. 31A-D. Metabolically synthesized AngIV analogs induce dendritic spines. Hippocampal neurons transfected with mRFP-β-actin were treated with vehicle (PBS), 10-12 M Nle1-AngIV, as a positive control, or various concentrations for several stabilized analogs for 5 days in culture or for 30 minutes prior to fixation on day in vitro 12 (DVI12). A, acetyl-Nle-YIH; B, D-Nle0YI; C, GABA-YI; D, Nle-YIH-amide. All analogs increased spine numbers at 10-8 and 10-10 M concentrations (*p<0.05) with acetyl-Nle-YIH and D=Nle-HI increasing spine numbers at even lower concentrations (*p<0.05). Mean=/-S.E.M., n=100.
Figure 31A:
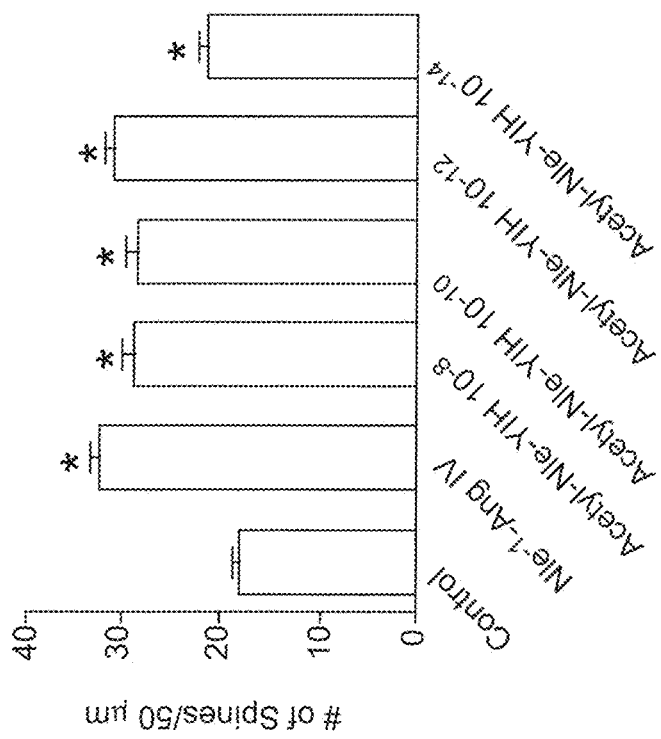
Figure 31D:
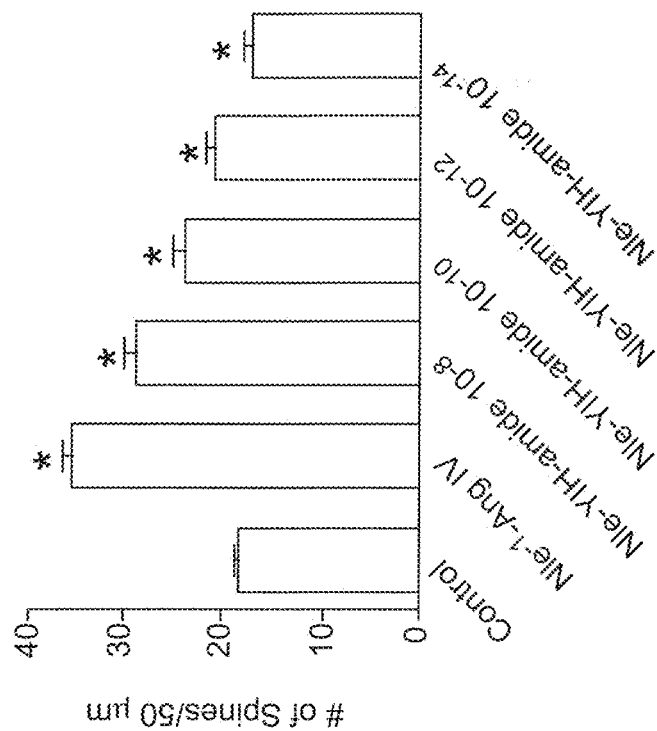
Figure 31C:
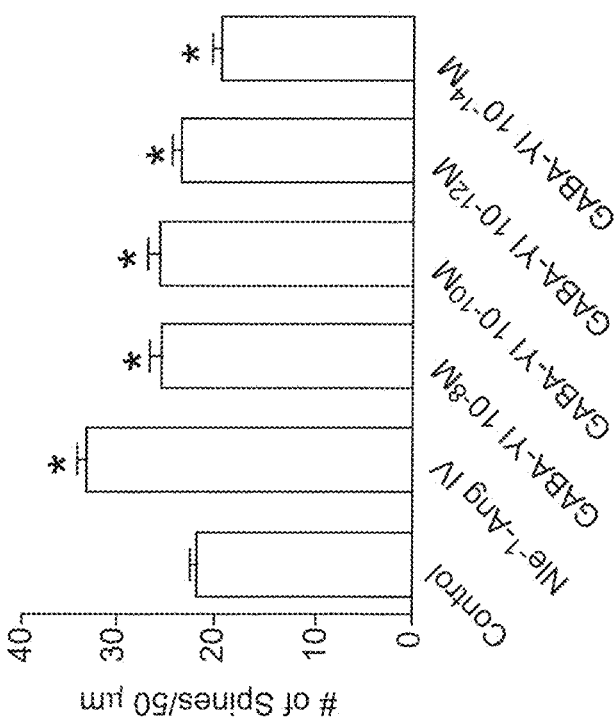

As a second measure of cognitive function, the persistence and strength of the learned task was assessed with a probe trial on Day 9 (FIG. 30B). The rats were exposed to the maze with no pedestal for two minutes and time spent in the quadrant that originally contained the submerged pedestal was determined. These data mirrored the escape latency results with all treated groups performing better than the scopolamine/deficit group ($p<0.01$-$0.001$). Again the performance by the group treated with GABA-Tyr performance was superior to all the other compound treated groups ($p<0.05$-$0.01$) and not different from the vehicle control group ($p>0.05$).

N- and C-Terminal Modified Nle¹-AngIV Analogs Stimulate Dendritic Spinogenesis.

The ability of the cognitively active fragments described here to support hippocampal spinogenesis was tested and the results are presented in FIG. 31A-D. As can be seen from the dose-response curves, each of the metabolically stabilized molecules supported hippocampal spinogenesis. Surprisingly, GABA-Tyr-Ile, which had consistently exhibited the most profound pro-cognitive activity, did not appear to be the most potent generator of new dendritic spines.

N-Hexanoic-Tyr-Ile-(6)Aminohexanoic Amide (Dihexa) is a Metabolically Stabilized, Blood-Brain Barrier Permeable Molecule.

The data presented in Table 7 indicate that increased stability can be imparted to Nle$^1$-AngIV-derived compounds by both N- and C-terminal modification. In addition, the functional studies summarized in FIG. 30 indicate that replacement of norleucine in the number one position with the straight chain, non-α-amino acid GABA yielded a molecule with superior pro-cognitive activity. With this information in hand we synthesized a series of compounds, exemplified by dihexa, that not only were protected at both terminals, but contained the replacement of norleucine with a straight chain acyl group. Instead of simply appending a non-α-amino long straight chain amino acid to the N-terminal we chose to eliminate the N-terminal amine entirely, which increased overall hydrophobicity and removed a critical hydrogen bonding site. As can be seen in Table 8 these modification significantly increased the serum stability of dihexa in comparison to Nle$^1$-AngIV.

Figure 32:
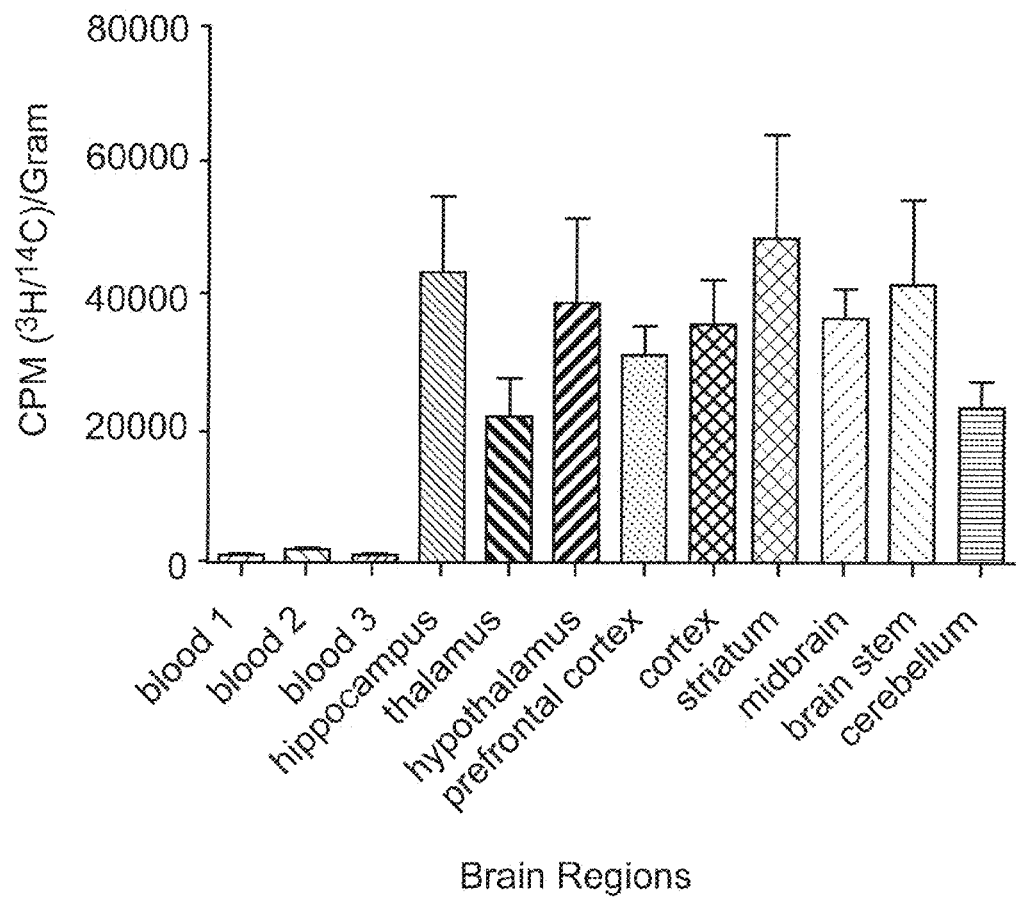
FIG. 32. Dihexa is concentrated in multiple brain regions. Rats fitted with a carotid cannula were anesthetized and infused with 0.5 ml of isotonic saline containing 10 μCi of $^3$H-dihexa and 2 μCi $^{14}$C-Inulin, a vascular marker. Thirty minutes after infusion the rats were decapitated, the brains removed, and various brain regions dissected. The tissues were then weighed and solubilized with NCS, an organic protein solubilizing agent, and 10 ml of scintillation was added. Samples were counted with a scintillation counter using two different windows to quantitate both $^3$H and $^{14}$C counts. $^3$H/$^{14}$C ratios were determined so that blood derived dihexa contamination of tissues could be determined. The results indicate that all brain regions concentrated dihexa (***p<0.001) when compared to blood but no area was statistically different from any other (p>0.05).The average $^3$H/$^{14}$C for blood was 1687. Mean+/-S.E.M.; n=4.

The purpose of elongating the N-terminal acyl group and removing the N-terminal amino group was to increase the probability that resultant molecules might be BBB permeable and access the brain parenchyma. To evaluate the success of the modifications that were incorporated in dihexa in this regard rats were fitted with carotid cannulas and infused with 10 μCi of $^3$H-dihexa and 2 μCi of $^{14}$C inulin, a vascular space marker. Thirty minutes after infusion, brains were removed and dissected and blood samples taken. After solubilization, $^3$H and $^{14}$C were quantified by dual window scintillation counting to determine the amount of dihexa and inulin in brain and blood samples. The ratio of dihexa/inulin in blood was then used to account for any blood contamination in the various brain regions. More importantly, $^3$H/$^{14}$C ratios above that observed in blood were indicative of dihexa being concentrated. As can be seen in FIG. 32, all the brain regions examined avidly concentrated dihexa attesting to its ability to cross the BBB.

Dihexa has a Long Circulating Half-Life.

Figure 33:
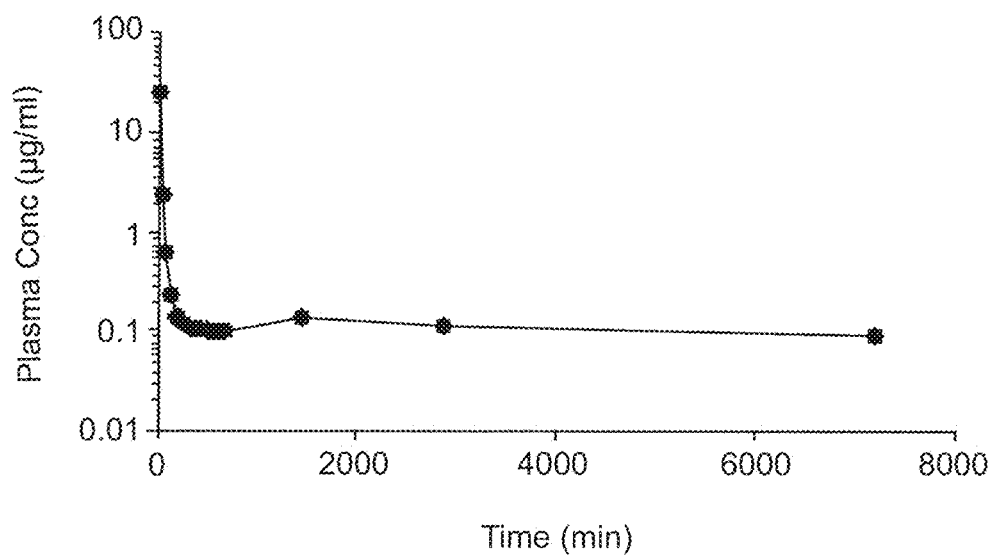
FIG. 33. Dihexa plasma levels after intraovascular (IV) infusion. Representative distribution/elimination curve for Dihexa. Dihexa was administered to aduts male Sprague Dawley rats at 10 mg/kg. Plasma samples were collected and analyzed by HPLC-MS. Plasma data were modeled by non-copartmental analysis. Dihexa exhibited a lone half-life (t½) of 12.68 days.

To begin to evaluate the potential clinical utility of dihexa Adult male Sprague-Dawley rats were administered 10 mg/kg dihexa intravenously and in-vivo pharmacokinetics determined. An example of the resulting plasma concentration/time profile is shown in FIG. 33, dihexa exhibited rapidly decreasing plasma levels from 0 to 4 hours suggesting that both distribution and elimination occurred during this period. After 4 hours, the rate of clearance declined and plasma levels became more stable, exhibiting a relatively linear rate of decline suggesting a phase of pure elimination from 4 to 120 hours. The exception from the linearly declining pattern of plasma levels was between 8.5 to 13 hours, when plasma levels were actually lower than at 24 hours. These results suggest that a small fraction of dihexa undergoes enterohepatic recirculation, which could cause an increase in plasma levels. Elevations in plasma concentration due to enterohepatic recirculation are usually observed after a meal when bile containing drug is released into the duodenum and the drug is reabsorbed from the intestine (Kwon 2001). Since rats were allowed food 12 hours after the onset of the study, any enterohepatic recirculation would be expected to occur subsequent to 12 hours, the time period that corresponded with rising plasma levels of dihexa.

Relevant pharmacokinetic parameters for dihexa as determined after IV dosing are summarized in Table 9. Plasma data were modeled by non-compartmental analysis using Win-Nonlin® software. dihexa exhibited a long half-life ($t_{1/2}$) of 12.68 days following IV administration and similarly when delivered intraperitoneally (8.83+/−2.41 days, Mean+/−SEM; N=4). dihexa appeared to be extensively distributed outside the central blood compartment and/or bound within the tissues as evidenced by its large volume of distribution (Vd). These results, which suggest that dihexa is very hydrophobic (log P) and are in agreement with the outcome of QSAR modeling estimates generated by ADMET Predictor® that calculated an octanol:water partition coefficient of 177.8 for dihexa (Table 10).

TABLE 9

Dihexa pharmacological parameters

| Pharmacokinetic Parameter | Mean ± SEM |
| --- | --- |
| AUC0-∞ (min · μg/mL) | 4471 ± 1408 |
| Vd (L/kg) | 54.4 ± 14.8 |
| Cp0 (μg/mL) | 87.3 ± 31.9 |
| t½ (min) | 18256 ± 7787 |
| KE (min−1) | 0.00007 ± 0.00004 |
| CL (L/min/kg) | 0.0026 ± 0.0007 |

N = 3

TABLE 10

Predicted Physicochemical Properties of Dihexa

| Physicochemical Property | Predicted Value |
| --- | --- |
| logP | 2.25 |
| Peff | 1.78 |
| Pavg | 0.62 |
| PrUnbnd | 22.59 |

Not surprisingly because of its stability, hydrophobic character, and small size, dihexa was predicted to be orally bioavailable. The $P_{eff}$ value represents the predicted effective human jejunal permeability of the molecule (Table 10). The predicted $P_{eff}$ value for dihexa (1.78) is intermediate between the predicted $P_{eff}$ values for enalapril (1.25) and piroxicam (2.14), two orally bioavailable drugs. dihexa was also predicted to be 22.59 percent unbound to plasma proteins in circulation, thus making it available for distribution into the tissues.

Figure 34:
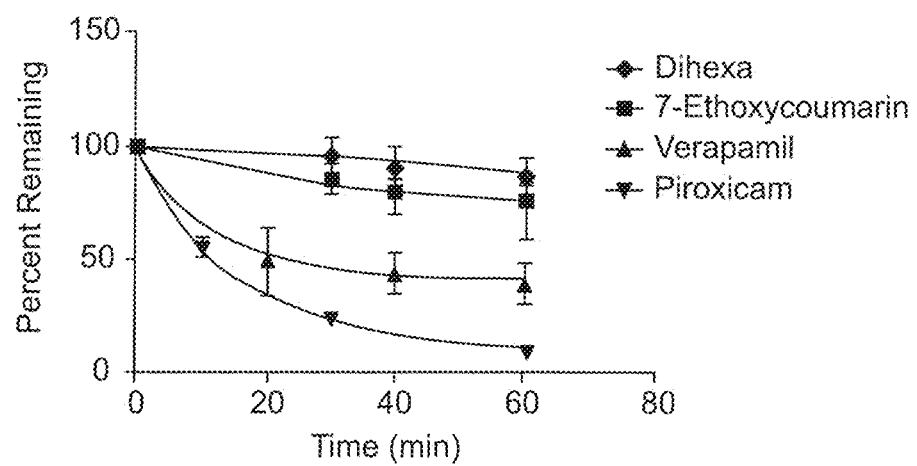
FIG. 34. Phase I metabolism of Dihexa. Phase I metabolism of Dkhexa was investigated using pooled rat liver microsomes. Dihexa exhibited an average intrinsic clearance (CI$_{in}$) of 2.72 μL/min/mg and an average half=life of 509.4 minutes. The stability of piroxicam, verapamil and 7-ethoxy-coumarin were also determined and utilized as high, moderate and low metabolized controls, respectively. Data is presented as the percent remaining time (n=3; mean+/-SEM).

Also contributing to its slow removal from the blood was a lack of Phase I metabolism for dihexa. Phase I metabolism of dihexa, which was determined using pooled male rat liver microsomes, was found to be very low with an average intrinsic clearance ($Cl_{int}$) of 2.72 μL/min/mg and an average half-life of 509.4 minutes. To provide a context for dihexa's clearance rate the stability of piroxicam (60.2 μL/min/mg), verapamil (112.5 μL/min/mg) and 7-ethoxycoumarin (136.7 μL/min/mg) was also monitored as high, moderate and low metabolized standards, respectively. The clearance rates indicated above were within the published ranges for these often employed standards (Di 2003, Shou 2005, Lu 2006, Behera 2008). The clearance time courses for dihexa and the standards fit curves defining single-phase exponential decay processes with an $R^2$ values between of 0.96 and 0.99 (FIG. 34).

Dihexa Exhibits Pro-Cognitive Activity

Figure 35A:
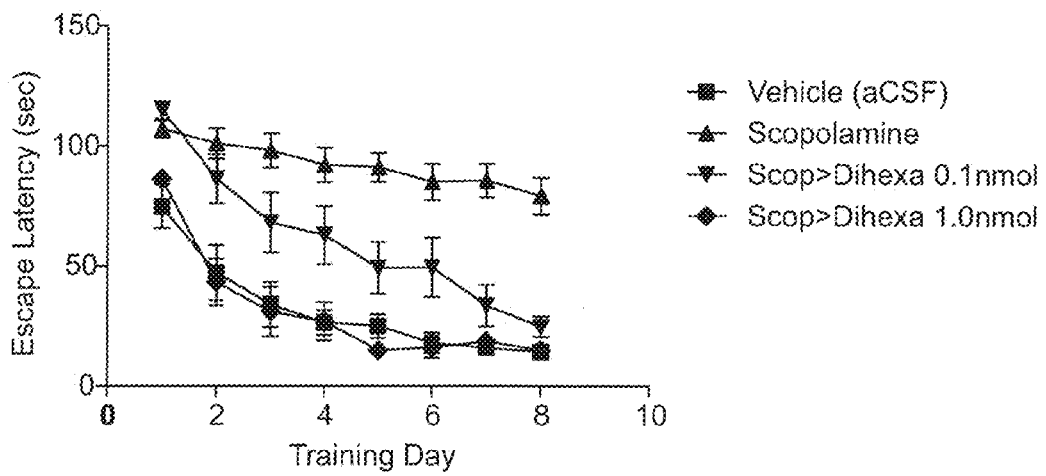
FIG. 35A-C. Dihexa reverses scopolamine-dependent spatial learning deficits. Group latencies to find the submerged platform in the Morris water maze task of spatial memory are shown. 20 minutes before beginning testing 3 month old male Sprague Dawley rats were given scopolamine directly into the brain (icv) and 15 minutes later dihexa was given either intraperitoneally (ip), or orally. There were 5 trials per day for 8 days. The latency to find the pedestal was considered a measure of learning and memory. A. Rats were pretreated with icv scopolamine (70 nmol in 2 μl aCSF) 20 min prior to training followed by the icv infusion of dihexa (0.1 or 1 nmol in 2 μl aCSF) 5 min prior to daily training. A two-way ANOVA with repeated measures indicated that all time points for the 1 nmol dihexa group were different from the scopolamine group, which received vehicle (aCSF) instead of dihexa (***p<0.001). The lower, 0.1 nmol, dose of dihexa was also significantly improved performance when compared to the scopolamine group on days 5-8 of testing (*p<0.05). B. Rats were pretreated with icv scopolamine (70 nmol in 2 μl aCSF) 20 min prior to training followed 15 minutes later by an ip injection of dihexa in DMSO (<1%) at 0.05 mg/kg, 0.25 mg/kg, or 0.50 mg/kg. A two-way ANOVA with repeated measures indicated that the latency curves for dihexa at 0.25 mg/kg and 0.50 mg/kg were different than the scopolamine▶ aCSF group's learning curve (*p<0.001). The 0.50 mg/kg group was not different than the vehicle control group (p>0.05) while the 0.05 mg/kg dihexa group was not different than the scopolamine group (p>0.05). C. Rats were pretreated with icv scopolamine (70 nmol in 2 μl aCSF) 20 min prior to training followed by oral delivery (gavage) of dihexa at 1.25/kg and 2.0 mg/kg 0.25 mg/kg (suspension in isotonic NaCl), 5 min prior to daily training. The high oral (2 mg/kg) dose of dihexa completely reversed the scopolamine-dependent learning deficit (*p<0.001) while the effect of scopolamine was partially reversed at the 1.25 kg/mg dose on days 3-8 (p<0.01). aCSF=artificial cerebrospinal fluid. Mean+/-SEM; n=8-10

The essential test of the success of the structural modifications incorporated into dihexa was whether it possessed pro-cognitive activity like its parent compound $Nle^1$-AngIV. Therefore, dihexa's ability to reverse scopolamine-dependent deficits in water maze performance was established. The initial study, which was simply tasked with verifying its pro-cognitive activity, entailed the direct brain delivery of dihexa via icv cannula. The data presented in FIG. 35A confirm our expectation that dihexa would retain biological activity. Both the low and high dose groups of dihexa yielded significantly improved performance when compared to the scopolamine group from day 2 of testing on ($p<0.001$). The high dose group was indistinguishable from the vehicle control group at all testing days ($p>0.05$).

Figure 35B:
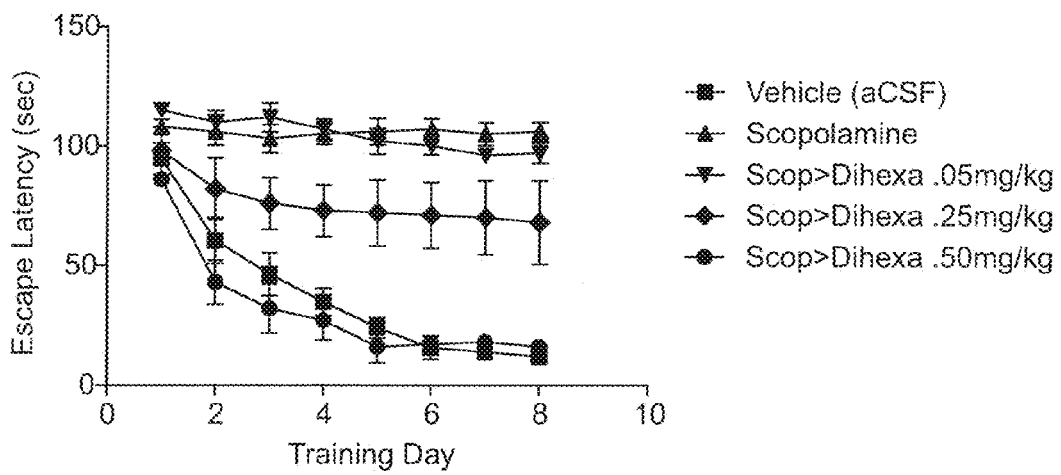
Figure 35C:
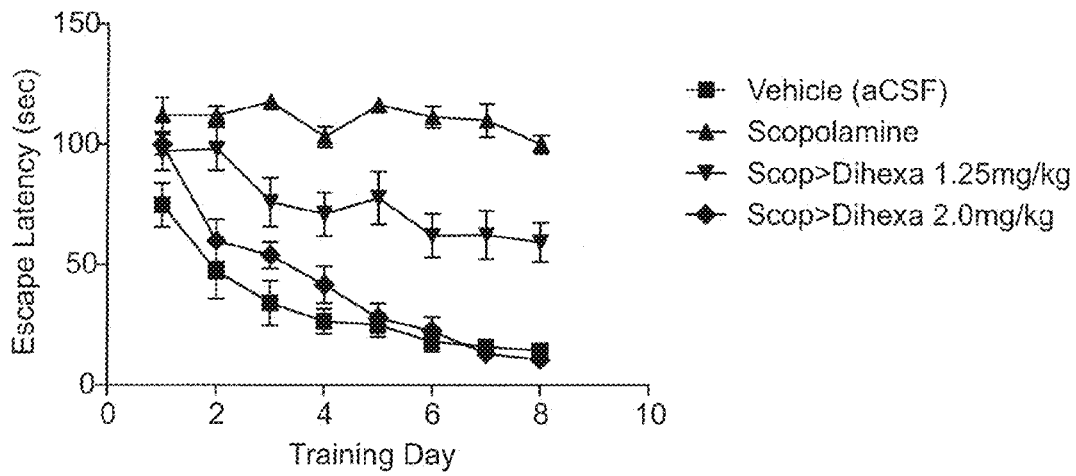

Since the ultimate goal of the project was to produce a clinically relevant molecule that could be delivered peripherally but still exhibit pro-cognitive/anti-dementia activity, the effectiveness of both the intraperitoneal and oral delivery routes of dihexa administration were determined using the scopolamine model. As can be seen in FIGS. 35B&C, both delivery methods yielded the anticipated biological activity. Furthermore, both studies indicated a clear dose-response relationship between the dose of dihexa and water maze performance. The high doses of each method of delivery (ip=0.5 mg/kg/day; oral=2.0 mg/kg/day) produced performances that were significantly improved over that seen in the scopolamine groups ($p<0.001$) and indistinguishable from vehicle controls ($p>0.05$).

Figures 36A, 36B:
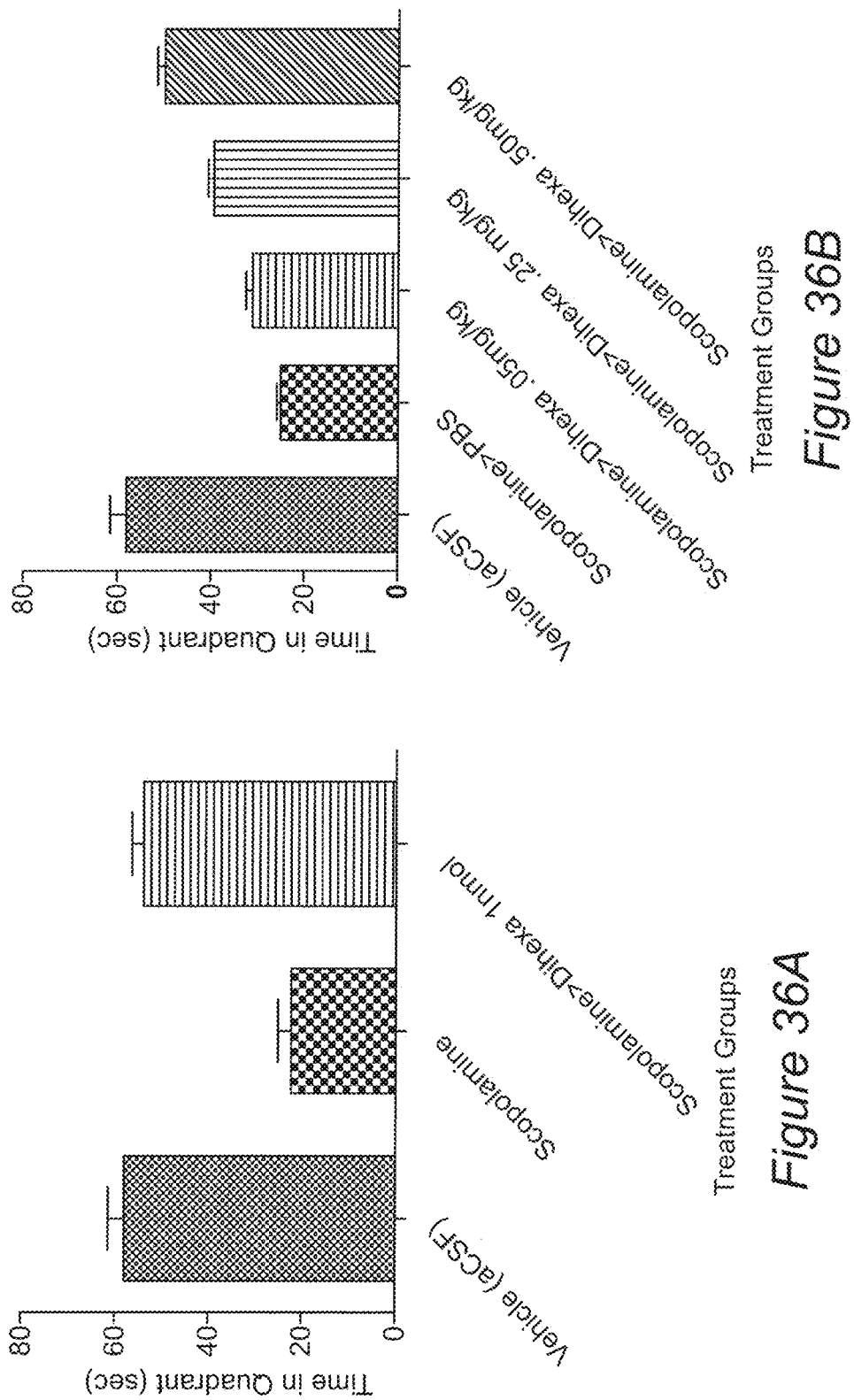
FIG. 36A-C. Dihexa increases time in the target quadrant during day 9 probe trials. Time spent in the target quadrant was recorded for each experimental group following icv, ip, and oral delivery of dihexa. A. In the icv study the scopolamine group performed below the chance level (30 s) and was significantly different from the vehicle control group and the scopolamine▶ dihexa 1 nmol group (*p<0.001) while the scopolamine▶ dihexa 1 nmol and vehicle control groups were not different (p>0.05). B. In the ip delivery study the scopolamine PBS group preformed below the chance level and was different than the vehicle control group (*p<0.001). Each of the treatment groups was different than the scopolamine▶ PBS group (***p<0.001-*p<0.05) while each of the treatment groups was different than one another (***p<0.001-*p<0.05) exhibiting the same dose-response relationship observed in the initial water maze study. C. In the oral delivery study the scopolamine▶ PBS group preformed near the chance level and was different than the vehicle control group (***p<0.001). Both of the treatment groups were different than the scopolamine▶ PBS group (*p<0.05 and *p<0.001 respectively) while both of the treatment groups were different from one another (*p<0.001) exhibiting the same dose-response relationship observed in the initial water maze study. Mean+/-S.E.M.; n=8-10.
Figure 36C:
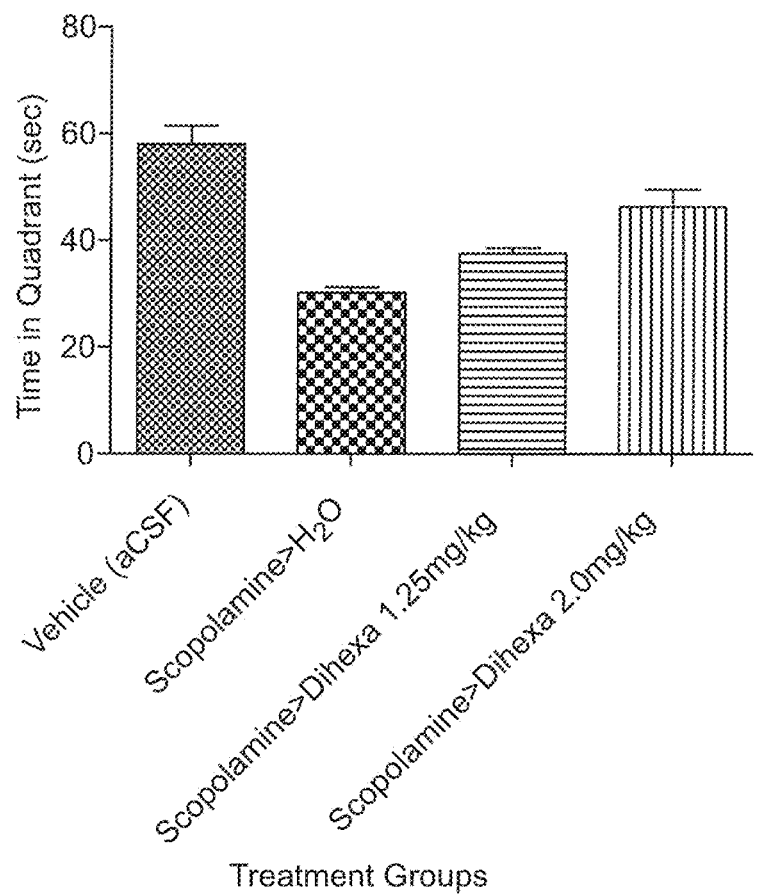

Probe trials on day 9 were again employed to evaluate the strength and persistence of the learned task. As can been seen in FIGS. 36A, B, &C, dihexa at its highest dose significantly ($p<0.001$) increased the time spent in the target quadrant when compared to the scopolamine impaired groups regardless of the delivery method employed and was not different from non-scopolamine treated controls ($p>0.05$). In each case where multiple doses of dihexa were utilized the probe trial data yielded a dose-response relationship similar to that observed for escape latencies.

Figure 37:
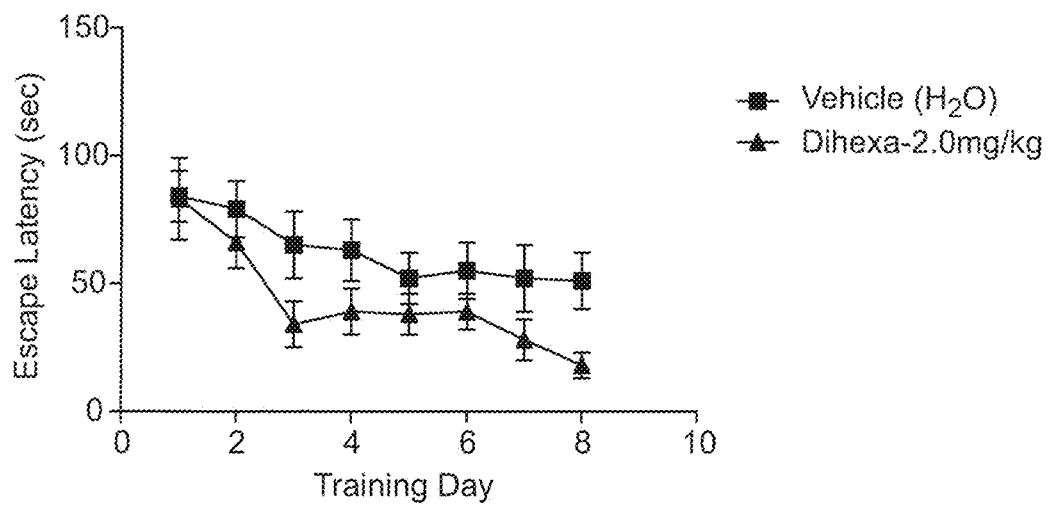
FIG. 37. Dihexa improves spatial learning in aged rats. Group latencies to find the submerged platform in the Morris water maze task of spatial memory are shown. Five minutes before beginning testing 24 month old mixed sex (3 male and 3 female/group) Sprague Dawley rats were administered dihexa (2 mg/kg) orally by gavage (suspension in isotonic NaCl), on a daily basis. There were 5 trials per day for 8 days. The latency to find the pedestal was considered a measure of learning and memory. The learning curve for the treated rats was significantly different than that of the non-treated rats (Mann-Whitney U, *p<0.03). Mean+/-S.E.M.; n=6.

While the scopolamine model is often used to assess the cognitive enhancing capacity of experimental molecules it clearly initiates learning deficits in a non-physiological manner that only results in acute deficits. In order to begin to assess the clinical potential of dihexa as an anti-dementia drug we chose to evaluate its effects on a more physiological relevant model—the aged Sprague Dawley rat. Rats like human develop age-related cognitive difficulties. Typically about 50% of rats exhibit impaired performance in the water maze when compared to 3 month old rats (Zeng et al., 2012). As such, we evaluated the ability of orally delivered dihexa (2 mg/kg/daily) to impact water maze learning in 24 month old Sprague Dawley rats of mixed gender. As expected the results shown in FIG. 37 indicate that dihexa significantly improved performance (p<0.05) on most of the test days. It should be noted that because these aged rats were not pre-screened for cognitive deficits the results substantially underestimate the effect of dihexa. The expectation that only half of the untreated rats would be effective learners even without dihexa treatment likely contributed to the high variability in escape latencies seen with the untreated group.

Dihexa Induces Spinogenesis in Cultured Hippocampal Neurons.

Recently the pro-cognitive effects of Nle$^1$-AngIV, the parent compound of dihexa, and several C-terminal truncated analogs have been correlated with their ability to induce dendritic spine formation and the establishment of new synapses (Benoist et al., 2011). As such, the influence of dihexa on spinogenesis and synaptogenesis in high density mRFP-β-actin transfected rat hippocampal neuronal cultures was evaluated. Actin-enriched spines increased in number in response to both dihexa (FIGS. 38B&D) and Nle$^1$-AngIV (FIGS. 38C&D) following 5 days of treatment at $10^{-12}$M concentration that started on the 7$^{th}$ day in vitro (DIV7) The results revealed a near 3-fold increase in the number of spines stimulated by dihexa and greater than 2-fold increase for Nle$^1$-AngIV. Both treatment groups differed significantly from the vehicle control group for which the average number of spines per 50 μm dendrite length was 15. The average number of spines for the dihexa and Nle$^1$-AngIV treated groups was 41 and 32 spines per 50 μm dendrite length, respectively (mean±S.E.M., n=200 dendritic segments; ***=P<0.001 by one-way ANOVA and Tukey post hoc test).

The icv water maze data with dihexa indicate a modest but significant improvement in spatial learning performance even on the first day of testing thus suggesting that the underlying mechanism responsible for the behavior must be rapidly engaged. Therefore the ability of both dihexa and Nle$^1$-AngIV to promote spinogenesis was assessed following an acute 30 minute application on the final day of culturing (FIG. 38E). The acute 30 minute application of dihexa and Nle$^1$-AngIV, on the 12$^{th}$ day in vitro (DIV12) reveals a significant increase in spines compared to 30 minute vehicle treated neurons (dihexa mean spine numbers per 50 μm dendrite length=23.9; Nle$^1$-AngIV mean spine numbers per 50 μm dendrite length=22.6; vehicle control treated neurons mean spine numbers per 50 μm dendrite length=17.4; n=60; ***=p<0.0001 by one-way ANOVA followed by Tukey post-hoc test).

Figure 39:
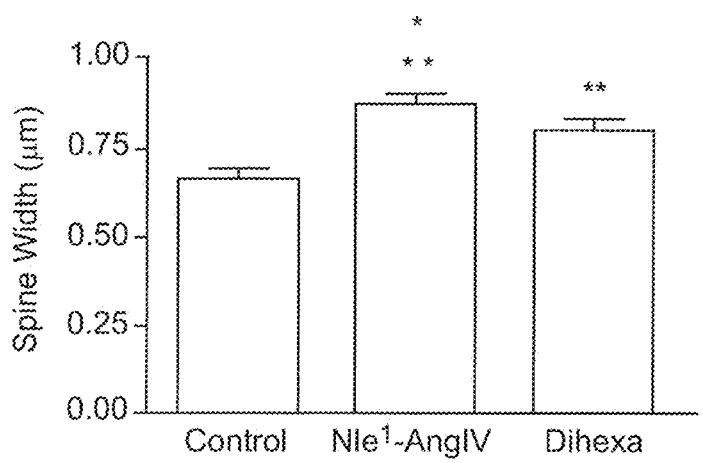
FIG. 39. Nle$^1$-AngIV and Dihexa increase dendritic spine head width. The width of a dendritic spine head is considered and indicator of synaptic strength. Spine heads with a greater surface area can accommodate more neurotransmitter receptors and are more likely to form more responsive synapses. Neonatal hippocampal neurons transfected with mRFP-β-actin were treated with $10^{-12}$ M Nle$^1$-AngIV or $10^{-12}$ M Dihexa for 5 days in culture prior to fixation on day in vitro 12 (DIV12). Both Nle$^1$-AngIV and Dihexa treatment induced increases in spine head width suggesting augmented neurotransmission. ***p<0.001; Mean±S.E.M; n=100.
Figure 40A:
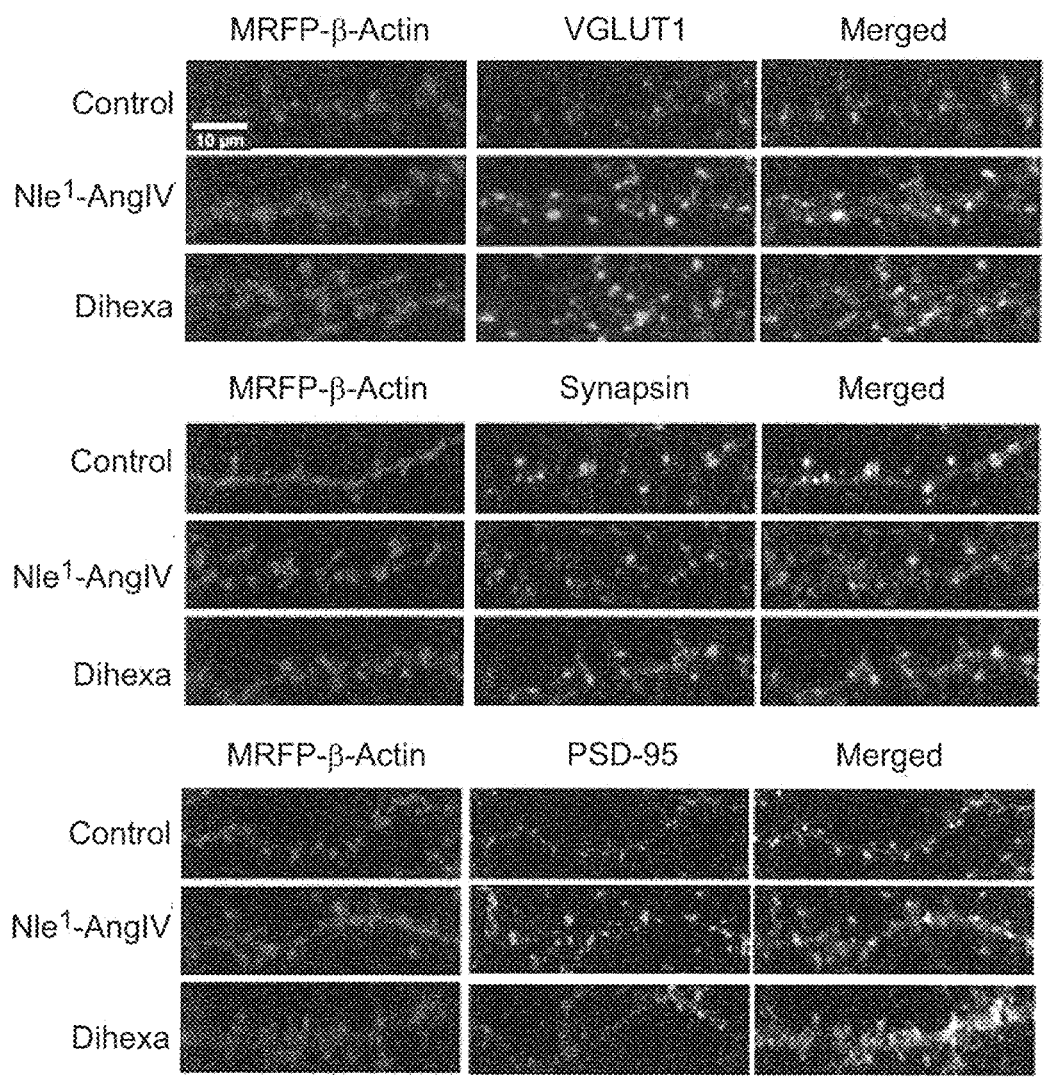
FIG. 40A-G. Localization of synaptic markers following Nle$^1$-AngIV and dihexa-dependent dendritic spine induction. Dihexa and Nle$^1$-AngIV treated neurons were immunostained for the universal presynaptic marker synapsin, the glutamatergic presynaptic marker VGLUT1, and the postsynaptic density maker PSD-95. The percent correlation between the postsynaptic spines and presynaptic puncta, which represented a different marker in each panel, was determined and used as an indicator of functional synapses. A) Representative images of hippocampal neurons transfected with mRFP-β-actin and immunostained for the excitatory presynaptic marker VGLUT1, the general presynaptic marker synapsin, and the postsynaptic marker PSD-95 following a 5 day treatment with vehicle, $10^{-12}$ M Nle$^1$-AngIV or $10^{-12}$ M dihexa. B) Bar graph confirming the expected increase in the number of dendritic spines following treatment with vehicle, Nle$^1$-AngIV or dihexa (*p<0.001; mean±S.E.M.; n=25 dendritic segments). C) Bar graph showing the percent correlation between dendritic spines after treatment and the glutamatergic presynaptic marker VGLUT1. No significant differences between the stimulated neurons and vehicle control treated neurons were observed (P>0.05; mean±S.E.M.; n=25 dendritic segmnets). D) Bar graph confirming the expected increase in the number of dendritic spines following treatment with vehicle, Nle$^1$-AngIV or dihexa (*p<0.001; mean S.E.M.; n=25 dendritic segments). E). Bar graph showing the percent correlation between dendritic spines after treatment and the general presynaptic marker synapsin. No significant differences between the stimulated neurons and vehicle control treated neurons were observed (p>0.05; mean±S.E.M.; n=25 dendritic segments). F) Bar graph confirming the expected increase in the number of dendritic spines following treatment with vehicle, Nle$^1$-AngIV or dihexa (***p<0.001; mean±S.E.M.; n=25 dendritic segments). G) Bar graph showing the percent correlation between dendritic spines after treatment and the postsynaptic marker PSD-95. No significant differences between the stimulated neurons and vehicle control treated neurons were observed (p>0.05; mean±S.E.M.; n=25 dendritic segments). Together these data indicate that dendritic spines formed after treatment support functional synapses.
Figure 40B:
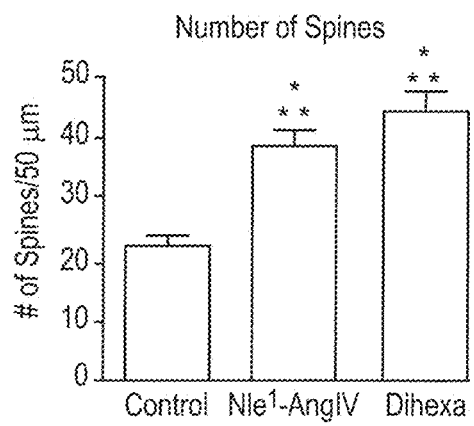
Figure 40C:
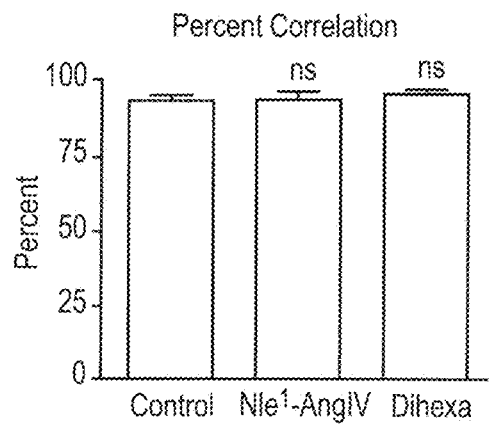
Figure 40D:
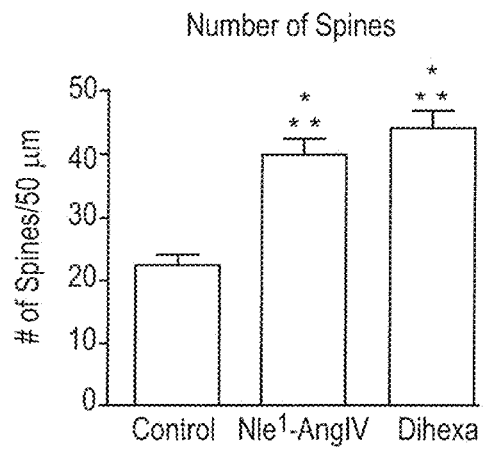
Figure 40E:
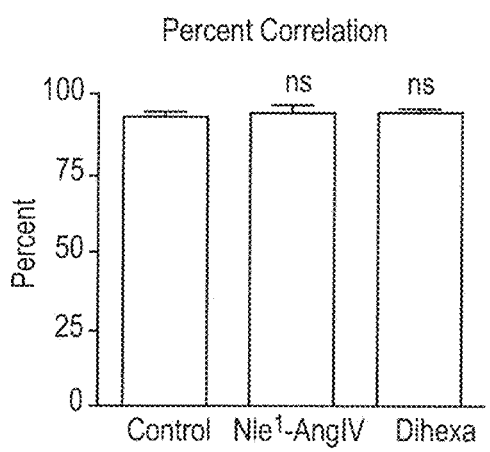
Figure 40F:
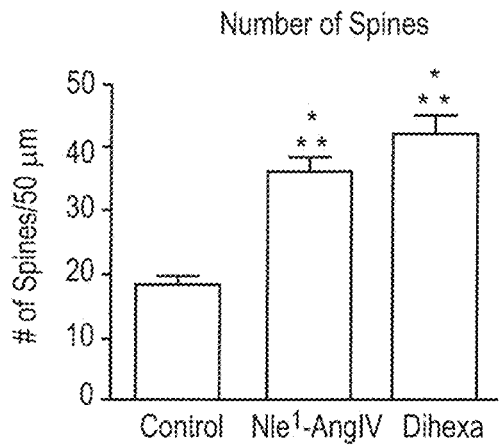
Figure 40G:
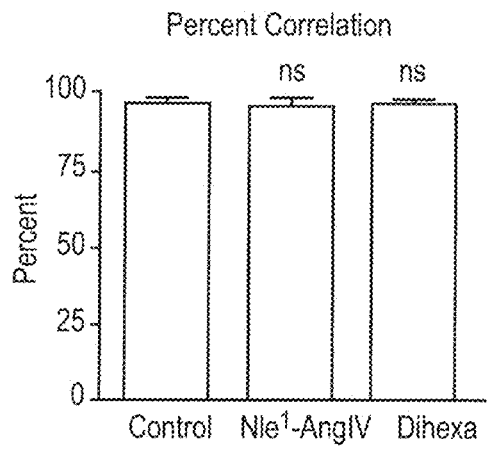

Strong correlations exist between spine size, persistence of spines, number of AMPA-receptors and synaptic efficacy. A correlation between the existence of long-term memories to spine head volume has also been suggested (Kasai, Fukuda et al.; Yuste and Bonhoeffer 2001; Yasumatsu et al. 2008). With these considerations in mind spine head size measurements were taken following 5 days of drug treatment. Results indicate that the $10^{-12}$ M dose of dihexa and Nle$^1$-AngIV both increased spine head width (FIG. 39). The mean spine head width for Nle$^1$-AngIV was 0.87 μm, 0.80 μm for dihexa, and 0.67 μm for vehicle controls.

Dihexa and Nle$^1$-AngIV Mediate Synaptogenesis

To assess the functionality of the newly formed dendritic spines, mRFP-β-actin transfected neurons were immunostained for three synaptic markers. Hippocampal neurons were stimulated for 5 days in vitro with $10^{-12}$ M dihexa or Nle$^1$-AngIV (FIG. 40). Since glutamate synaptic transmission is known to involve receptors that reside on dendritic spines, neurons were probed for excitatory synaptic transmission by staining for the glutamatergic presynaptic marker Vesicular Glutamate Transporter 1 (VGLUT1) (Balschun et al. 2010). The universal presynaptic marker synapsin was also visualized to assess the juxtaposition of the newly formed spines with presynaptic boutons (Ferreira and Rapoport, 2002). Finally PSD-95 served as a marker for the postsynaptic density (El Husseini et al. 2000).

Again dihexa and Nle$^1$-AngIV treatment significantly augmented dendritic spinogenesis (FIG. 40 B, D, F) in each of the three studies; mean spine numbers for the combined studies for Nle$^1$-AngIV=39.4; mean spine numbers for dihexa=44.2; and, mean spine numbers for vehicle treated neurons=23.1 (mean±S.E.M., ***=P<0.001). The percent correlation for the newly formed spines with synaptic markers VGLUT1, synapsin or PSD-95 is shown in FIGS. 40 C, E, and E. Dihexa and Nle$^1$-AngIV treatment-induced spines did not differ from control treated neurons in the percent correlation to VGLUT1, synapsin or PSD-95 (P>0.05) indicating that the newly formed spines contained the same synaptic machinery as already present spines. The above results suggest that the newly formed dendritic spines produced by dihexa and Nle$^1$-AngIV treatment are creating functional synapses.

To further support this conclusion, mini postsynaptic excitatory currents (mEPSCs), the frequency of which corresponds to the number of functional synapses, were recorded from mRFP-β-actin transfected hippocampal neurons (FIG. 41). The mean frequency of AMPA-mediated mEPSCs recorded from vehicle treated neurons was 3.06±0.23 Hz from 33 cells while Nle$^1$-AngIV induced a 1.7 fold increase (5.27±0.43 Hz from 25 cells; Mean±S.E.M.; *=P<0.001 vs. control group) and dihexa produced a 1.6 fold increase (4.82±0.34 Hz from 29 cells; *=P<0.001 vs. control group) confirming the expected expansion of functional synapses. No differences in amplitude, rise- or decay-times were observed (data not shown) which suggests that the individual properties of the synapse were not altered.

Figure 42B:
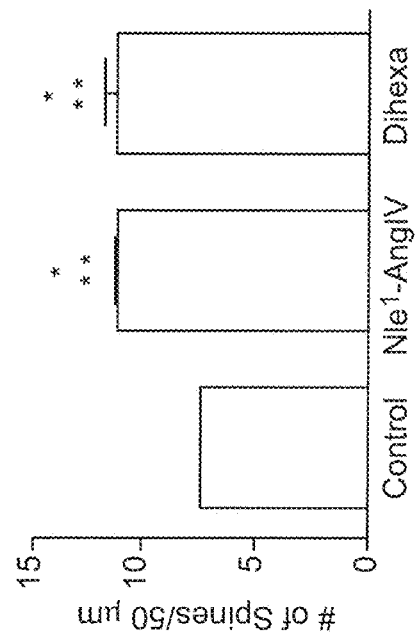
FIGS. 42A and B. Evaluation of Nle$^1$-AngIV- and Dihexa-dependent spinogenesis in CA1 hippocampal neurons from rat organotypic hippocampal slice cultures. Nle$^1$-AngIV and Dihexa were found to indued spinogenesis in rat CA1 hippocampal neurons. The number of spines present was determined. Slices were obtained from postnatal day 5 rats and were biolistically transfected with the red fluorescent dye Tomato to visualze dendritic structues. CA1 hippocampe neurons, which could be morphologically identified, were selected for evaluation because of their known plastic response during learning. A, representatice images of CA1 neuronal dendrites after 2 days of treatment; B, treatment induced spinogenesis is observed. Spine numbers measured for control slices were 7 per 50 μm dendrite length vs 11 spines per 50 μm dendrite length for both Nle$^1$-AngIV and Dihexa treated neurons. p<0.01; Mean+S.E.M.; n=17. Experiments were repeated at least 3 times with similar results.
Figure 42A:
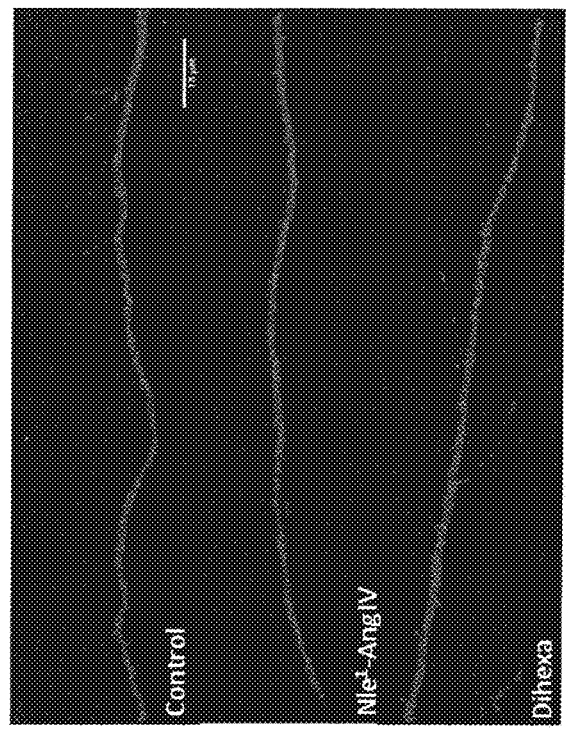

Dihexa and Nle$^1$-AngIV Induce Spinogenesis in Hippocampal Organotypic Cultures To further assess the physiological significance of the spine induction witnessed in dissociated neonatal hippocampal neurons the effects of dihexa and Nle$^1$-AngIV on spine formation in organotypic hippocampal slice cultures was evaluated. These preparations, while still neonatal in origin, represent a more intact and three dimensional environment than dissociated neurons. Hippocampal CA1 neurons, which have been functionally linked to hippocampal plasticity and learning/memory, were easily identified based on morphological characteristics and singled out for analysis. Dihexa and Nle$^1$-AngIV significantly augmented spinogenesis in organotypic hippocampal slice cultures when compared to vehicle treated neurons. There were no differences in spine numbers between the dihexa and Nle$^1$-AngIV treatment groups (FIG. 42). Spine numbers measured for control slices were 7 per 50 μm dendrite length vs. 11 spines per 50 μm dendrite length for both Nle$^1$-AngIV and dihexa treated neurons; mean±S.E.M., n=13-20 dendritic segments; **=P<0.01.

Discussion

The goal of this study was to develop an AngIV-derived molecule that retained the pro-cognitive/anti-dementia activity of AngIV and Nle$^1$-AngIV but possessed improved pharmacokinetic properties, thus allowing it to penetrate the BBB in sufficient quantities to reach therapeutic levels in the brain. The culmination of this effort was dihexa, a hydrophobic, N- and C-terminal modified, AngIV-related peptide. The cursory pharmacokinetic characterization of dihexa included in this study indicated that it was stable in serum, had a long circulating half-life, and penetrated the BBB. Data from behavioral studies using scopolamine amnesia and aged rat models, where dihexa was able to reverse cognitive deficits, indicated that the metabolic stability and BBB permeability of dihexa was apparently high enough to attain therapeutic brain levels after oral administration. Additional mechanistic studies demonstrated that both dihexa and Nle$^1$-AngIV, its parent compound, were effective stimulators of hippocampal synaptogenesis thus providing a rational explanation for their procognitive activities.

Using the N-terminal tripeptide of Nle$^1$-AngIV as a starting point the intermediate goal of this study was to establish the impact of various N- and C-terminal modifications of peptide stability. The results indicated that N-terminal modifications were particularly effective at enhancing metabolic stability; while C-terminal amidation offered more modest protection. The observation that replacement of the N-terminal norleucine with GABA yielded a compound with superior anti-dementia activity indicated that an N-terminal α-amino group was not required for activity. Furthermore, these data suggested that N-terminal, N-acyl tyrosine containing tripeptides should be biologically active. This observation, coupled with the added stability contributed by C-terminal amidation and the desire to increase the hydrophobicity of the peptide, led to the generation of a series of compounds with the structure, N-acyl-Tyr-Ile-(6) amino-hexanoic amide. After preliminary functional screening (see below), N-hexanoic-Tyr-Ile-(6)amino-hexanoic amide was chosen for further investigation with the expectation that it would be biologically active, metabolically stable, and BBB permeable.

The ultimate goal of this project was to produce a clinically useful pharmaceutical for the treatment of dementia including Alzheimer's disease. At its core dementia results from a combination of diminished synaptic connectivity among neurons and neuronal death in the entorhinal cortex, hippocampus and neocortex. Therefore, an effective treatment would be expected to augment synaptic connectivity, protect neurons from underlying death inducers, and stimulate the replacement of lost neurons from preexisting pools of neural stem cells. These clinical endpoints advocate for the therapeutic use of neurotrophic factors, which mediate neural development, neurogenesis, neuroprotection, and synaptogenesis.

The direct use of protein neurotrophic factors such as HGF as therapeutic agents has two serious limitations: 1) large size and hydrophilic character precludes BBB permeability; and 2) the need to be manufactured by recombinant methods at high cost, thus limiting its widespread use. The development of Dihexa has overcome these impediments by virtue of its oral activity, demonstrated pro-cognitive/anti-dementia activity, and low manufacturing costs.

REFERENCES FOR EXAMPLE 4

Balschun D, Moechars D, Callaerts-Vegh Z, Vermaercke B, Van Acker N, and Andries L, D'Hooge R (2010) Vesicular glutamate transporter VGLUT1 has a role in hippocampal long-term potentiation and spatial reversal learning. Cereb Cortex 20:684-693.

Behera D, Damre A, Varghese A, and Addepalli V (2008) In vitro evaluation of hepatic and extra-hepatic metabolism of coumarins using rat subcellular fractions: correlation of in vitro clearance with in vivo data. Drug Metabolism and Drug Interactions 23:329-350.

Di L, Kerns E H, Gao N, Li S Q, Huang Y, Bourassa it, and Huryn D M (2004) Experimental design on single-time-point high-throughput microsomal stability assay. J Pharmaceut Sci 93:1537-1544.

El-Husseini A E, Schnell E, Chetkovich D M, Nicoll R A, and Bredt D S (2000) PSD-95 involvement in maturation of excitatory synapses. Science 290: 1364-1368.

Ferreira A and Rapoport M (2002) The synapsins: beyond the regulation of neurotransmitter release. Cell Mol Life Sci 59:589-595.

Fisher A, Pittel Z, Haring R, Bar-Ner N, Kliger-Spatz M, Natan N, Egozi I, Sonego H, Marcovitch I and Brandeis R (2003) M1 muscarinic agonists can modulate some of the hallmarks in Alzheimer's disease: implications in future therapy. J Mol Neurosci 20:349-356.

Kasai H, Fukuda M, Watanabe S, Hayashi-Takagi A and Noguchi (2010) J Structural dynamics of dendritic spines in memory and cognition. Trends Neurosci 33:121-129.

Krebs L T, Kramár E A, Hanesworth J M, Sardinia M F, Ball A E, Wright J W, and Harding J W (1996) Characterization of the binding properties and physiological action of divalinal-angiotensin IV, a putative AT4 receptor antagonist. Regul Pept 3:123-30.

Lu C, Li P, Gallegos R, Uttamsingh V, Xia C Q, Miwa G T, Balani S K, and Gan L (2006) Comparison of intrinsic clearance in liver microsomes and hepatocytes from rats and humans: evaluation of free fraction and uptake in hepatocytes. Drug Metab Disposition 34:1600-1605.

Meijering E, Jacob M, Sarria J C, Steiner P, Hiding H and Unser M (2004) Design and validation of a tool for neurite tracing and analysis in fluorescence microscopy images. Cytometry A 58:167-176.

Shou W Z, Magis L, Li A C, Naidong W, and Bryant M S (2005) A novel approach to perform metabolite screening during the quantitative LC-MS/MS analyses of in vitro metabolic stability samples using a hybrid triple-quadrupole linear ion trap mass spectrometer. J Mass Spectrometry 40:1347-1356

Wayman G A, Davare M, Ando H, Fortin D, Varlamova O, Cheng HY, Marks D, Obrietan K, Soderling T R, Goodman R H and Impey S (2008) An activity-regulated microRNA controls dendritic plasticity by down-regulating p250GAP. Proc Natl Acad Sci USA 105:9093-9098.

Wayman G A, Impey S, Marks D, Saneyoshi T, Grant W F, Derkach V, Soderling T R. (2006) Activity-dependent dendritic arborization mediated by CaM-kinase I activation and enhanced CREB-dependent transcription of Wnt-2. Neuron 50:897-909.

Wright J W, Morseth S L, Abhold R H, and Harding J W (1985) Pressor action and dipsogenicity induced by angiotensin II and III in rats. Am J Physiol 249:R514-521.

Yasumatsu, N., Matsuzaki M, Noguchi J, and Kasai H (2008). "Principles of long-term dynamics of dendritic spines." J Neurosci 28: 13592-608.

Yuste, R. and Bonhoeffer T (2001) Morphological changes in dendritic spines associated with long-term synaptic plasticity Annu Rev Neurosci 24: 1071-89.

Example 5

Use of Dihexa to Treat Parkinson's Target Rational for Parkinson's Disease

The therapeutic options that are currently dominating the treatment of Parkinson's disease (PD) are neither effective long-term nor able to slow disease progression. Furthermore, these approaches, like levodopa administration or deep brain stimulation, have no capacity to restore lost function. The failure of these treatments to restore function and slow functional disease progression can be traced to their inability to correct the underlying cause of the dysfunction—diminished synaptic connectivity among neurons in the striatum and neuronal loss in the substantia nigra (SN). As such, an effective treatment would be expected to augment striatal synaptic connectivity, protect SN neurons from underlying death inducers, and ideally stimulate the replacement of lost SN neurons from preexisting pools of neural stem cells.

Neurotrophic factors mediate neural development, neurogenesis, neuroprotection, and synaptogenesis, and their use for the treatment of Parkinson's has been of interest. For example, glial cell line derived neurotrophic factor (GDNF) has been used in human clinical trials. The trials yielded mixed results and provided only partial validation for a neurotrophic-based PD treatment, while underscoring multiple issues raised by this type of therapy, including toxicity, inconsistent effectiveness, and the likely need to deliver drug to both the cell body area and terminal fields. In every study, the growth factor was delivered by cannula to the putamen as the naked protein or as an AAV2 carrying c-DNA construct. This highly invasive delivery methodology itself induces brain damage, introduces surgical risks from anesthesia and infection, and requires four separate cannulas to dose all essential terminal fields and cell body areas. Further, the exorbitant expense, limits widespread use of such therapy.

The potential of neurotrophic therapy for PD and other neurodegenerative diseases has thus far been consistently thwarted by drug delivery limitations. The solution to this problem, which is widely recognized, is the generation of small molecule, blood-brain-barrier (BBB) permeable drugs that act as mimetics of pertinent neurotrophic factors. The present study describes small molecule mimetics of the potent neurotrophic factor "hepatocyte growth factor" (HGF) which overcome these impediments. Some of the mimetics are BBB permeable, orally active, and display profound PD therapeutic as well as pro-cognitive/anti-dementia activity. Further, the mimetics are advantageously inexpensive to synthesize.

Therapeutic Strategy

The impediments to instituting a therapeutic strategy based on augmentation of a critical neurotrophic factor system for the treatment of PD are several. First neurotrophic factors are large proteins that lack significant BBB penetrability. Second, like all proteins neurotrophic factors are susceptible to degradation by proteases and hence require chronic dosing methods. Thirdly, they are manufactured using recombinant methods, resulting in high patient costs. All of these limitations are relevant to HGF.

Figure 43:
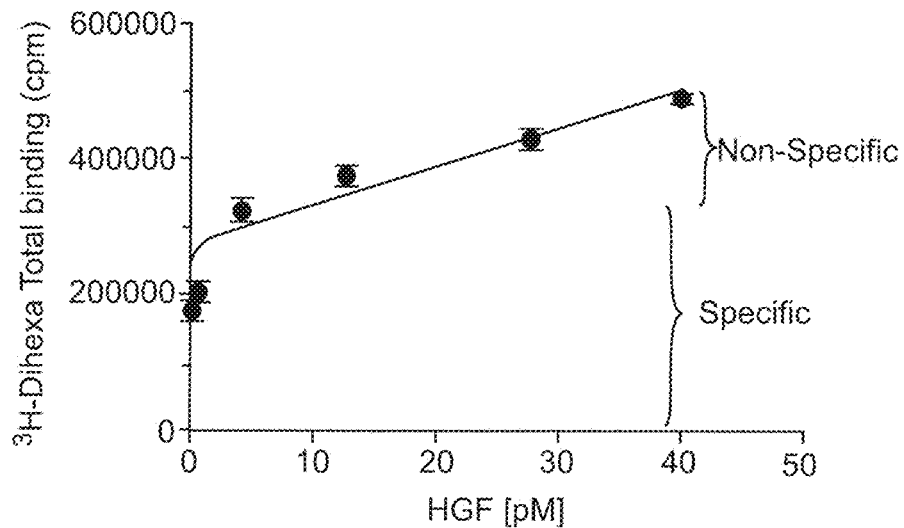
FIG. 43. $^3$H Dihexa (N-hexanoic-YI-6AH) binding to HGF. HGF was incubated with $^3$H Dihexa (250 μl of solution containing 10 μCi) for 30 minutes at 37° C. HGF-bound Dihexa was eluted from Biogel P6 columns after the addition of different concentrations of HGF. The radioactivity of the eluted solution was detected using a scintillation counter. These data demonstrate that Dihexa binds to HGF. Kd=2.21× $10^{-13}$M; N=4.
Figure 44:
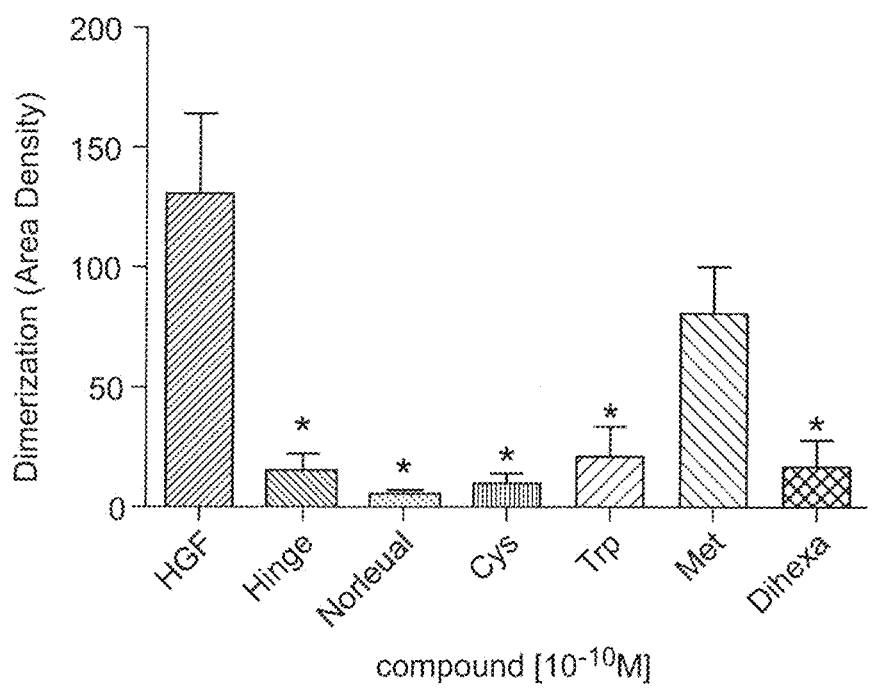
FIG. 44. Dihexa blocks HGF dimerization. HGF dimerization was assessed in the presence of various analogs including Dihexa. Dimerization was carried out for 30 minutes in the presence of heparin. Samples where cross-linked with BS3 and separated by native PAGE. Bands were visualized by silver staining and quantitated by densitometry. N=6, *** p<0.001.
Figure 45A:
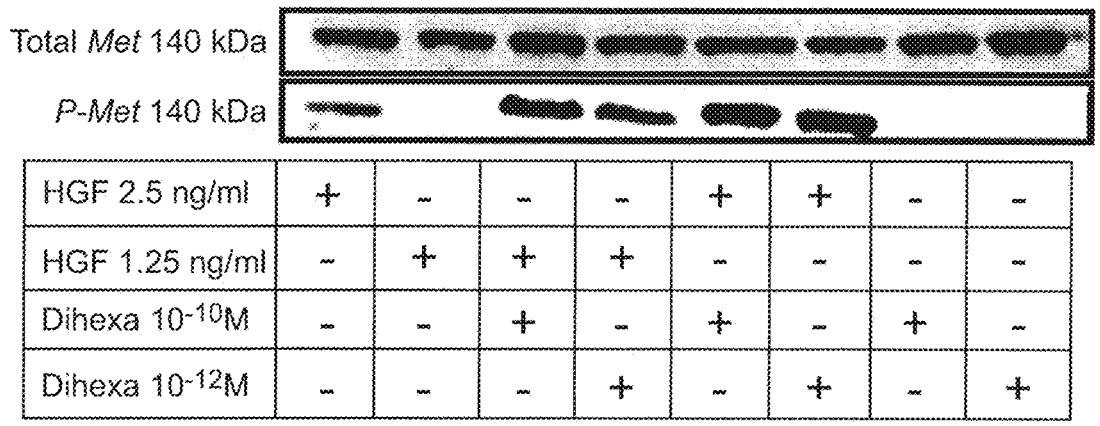
FIGS. 45A and B. Effect of the HGF mimetic, Dihexa, on c-Met activation. HEK 293 cells were treated with HGF+/− Dihexa and analyzed for phosphorylated (activated) c-Met by by immunoblotting. A, immunoblot results; B, graphic representation of the data.
Figure 45B:
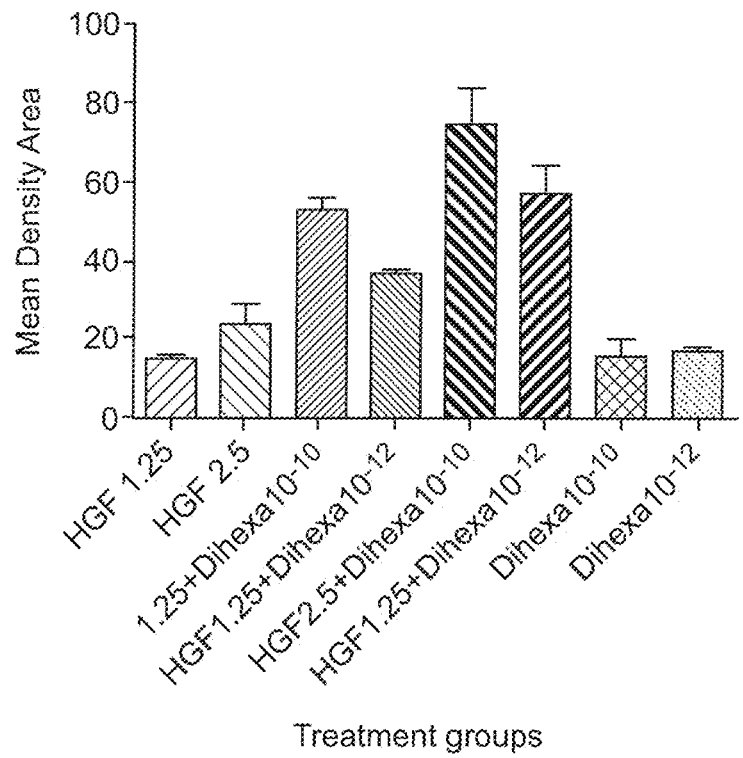

The present strategy therefore has been to enhance the activity of endogenous HGF instead of devising methods of HGF delivery. HGF dimerizes or multimerizes and that under physiological circumstances this process is required for its activation and ultimately the activation of its receptor, c-Met. The dimerization process is mediated by a small, 6-amino acid domain called the "hinge region". As described herein (e.g. see previous Examples) analogs that are "hinge region" mimics that bind to HGF with high affinity and block the dimerization process have been synthesized. The majority of the mimics are powerful HGF antagonists with substantial anti-angiogenic and anti-cancer activity. The exemplary mimic, Dihexa, binds to HGF with extraordinary affinity (FIG. 43), blocking HGF dimerization (FIG. 44), and markedly augments the ability of HGF to signal to c-Met (FIG. 45) and initiate cellular responses (as discussed above). Without being bound by theory, it appears that Dihexa binds HGF better than HGF itself forming an active heterodimer of HGF: Dihexa. Furthermore, it appears that HGF dimerization is a process designed to yield an active HGF conformation and not as typically suggested to mediate receptor dimerization. Further, the extraordinary affinity of HGF for Dihexa ($Kd=2.2\times10^{-13}M$) suggests that normally non-biologically active levels of HGF become physiologically relevant in the presence of a high affinity mimetic. Dihexa and its parent compounds exhibit powerful synaptogenic and pro-cognitive/anti-dementia activities (see previous Examples). In addition, these studies confirm that that the endogenous level of brain HGF is sufficient to support Dihexa's neuroprotective/neurorestorative activity and are in concert with the high levels of c-Met in the brain. These activities of Dihexa appear to be fully HGF dependent.

Behavioral Testing Protocols

Three groups of rats (8 animals per group) were utilized. The first two groups were prepared with unilateral 6-OHDA lesions and members of the first group was treated with MM-201 in DMSO 100 μl:PBS 8 ml (0.5 mg/kg, i.p.) Members of Group 2 were treated with sterile DMSO 100 μl:PBS 8 ml equivalent volumes to the weights. Members of Group 3 had only a sham surgery and served as the non-treated controls. These three groups of animals were tested on behavioral tasks the day prior to surgery and on 13 days following surgery. The tasks included rope hang, and gait analysis.

The rope hang test involved the placement of the forepaws on a hemp rope (1.0 cm in dia.) located 1 m above a basket of towels. Hang time was recorded beginning when the experimenter let go of the animal. This test was repeated 3 times/animal/test (5 minutes rest between each test) every other day.

Step gait analyses were conducted in a dark room painted black under red light. The bottoms of each rat's feet were painted with black ink (Parker Quink) and the rat was placed in a Plexiglas straight maze (length×width×height: 116×7.6× 10 cm). The maze was slightly elevated at one end such that the animal's tendency was to walk up hill. White paper strips placed on the floor of the maze were used to collect the gait patterns. These ink tracks were analyzed for stride length (distance between the mid point of the fore paw and hind paw comparing left and right strides).

Results

Figure 47:
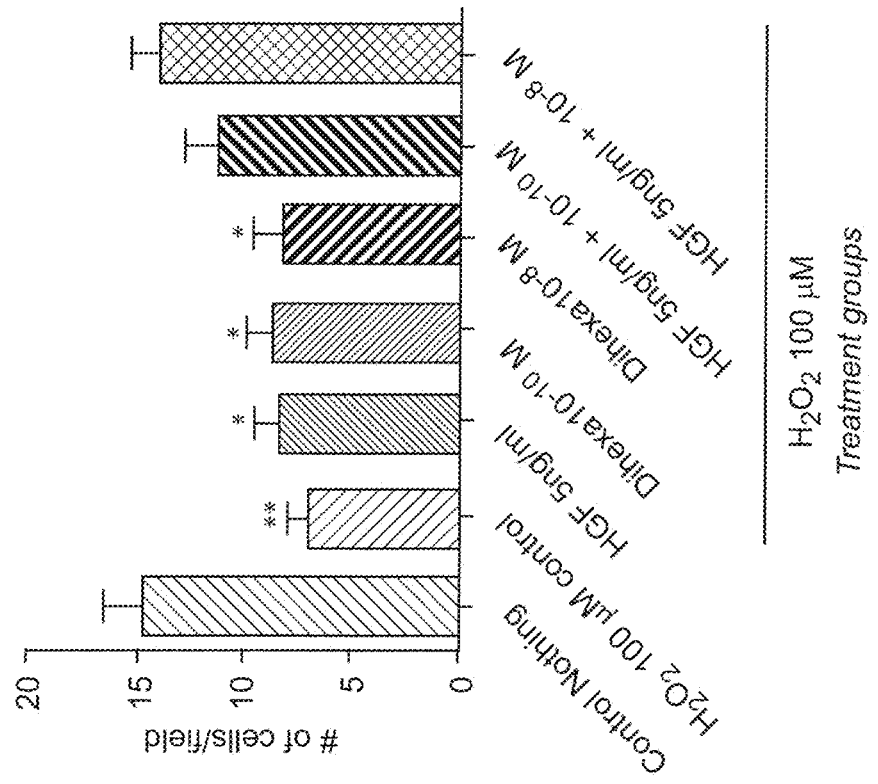
FIG. 47. Dihexa protects neurons from oxidative stress. Dissociated hippocampal neurons were treated with 100 μM $H_2O_2$ for 24 hrs+/−HGF at sub-threshold concentrations 5 ng/ml and or Dihexa at 2 different concentrations $10^{-8}$M and $10^{-8}$M. (*p<0.05,** p<0.01; Mean+/−SEM).
Figure 46:
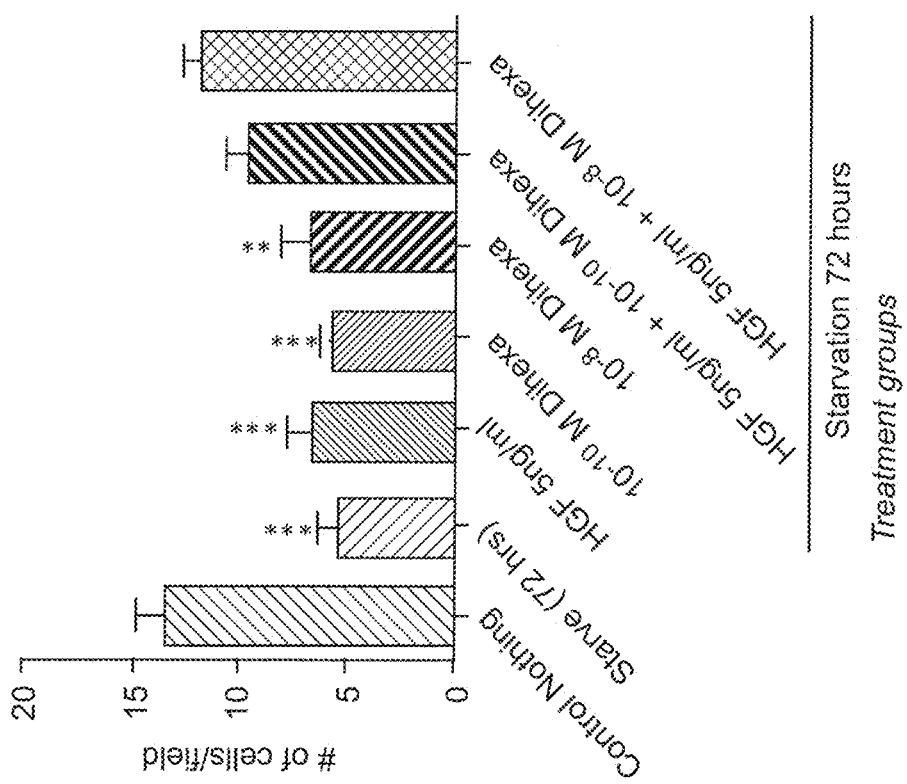
FIG. 46. Dihexa protects neurons from growth factor deprivation. Dissociated hippocampal neurons were starved for 72 hrs+/−HGF at sub-threshold concentrations 5 ng/ml and or Dihexa at 2 different concentrations $10^{-8}$M and $10^{-8}$M. (p<0.001,* p<0.0001; Mean+/−SEM).
Figure 48:
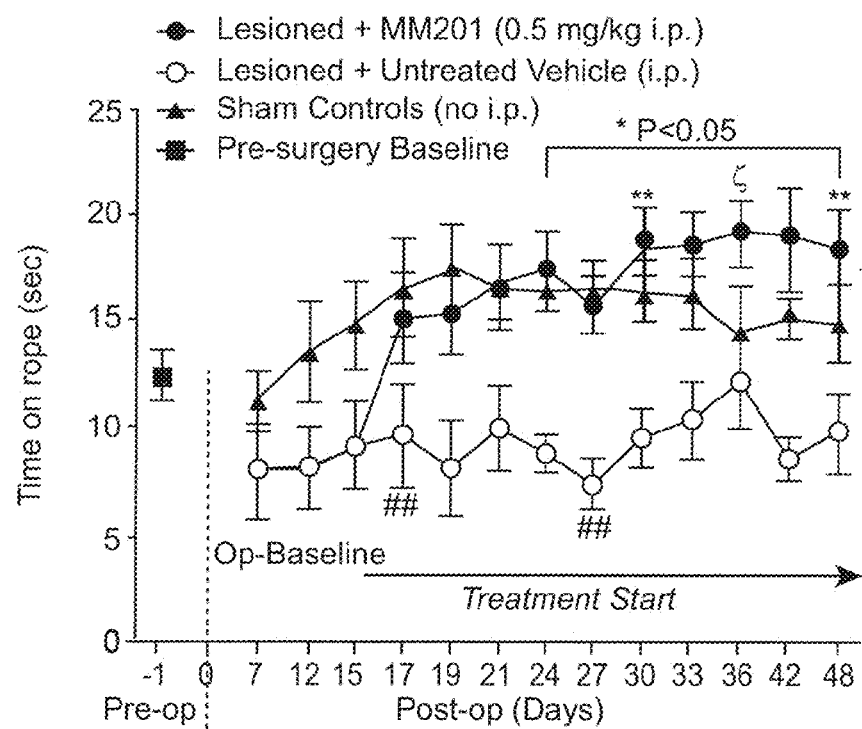
FIG. 48. Dihexa restores performance in the rope hang test. After 2 weeks of 6-OHDA lesion, rats were treated with either 0.5 mg/kg or equivalent volumes of the vehicle ip. Dihexa completely restored the performance of the treated animals on the rope hang test.
Figure 49:
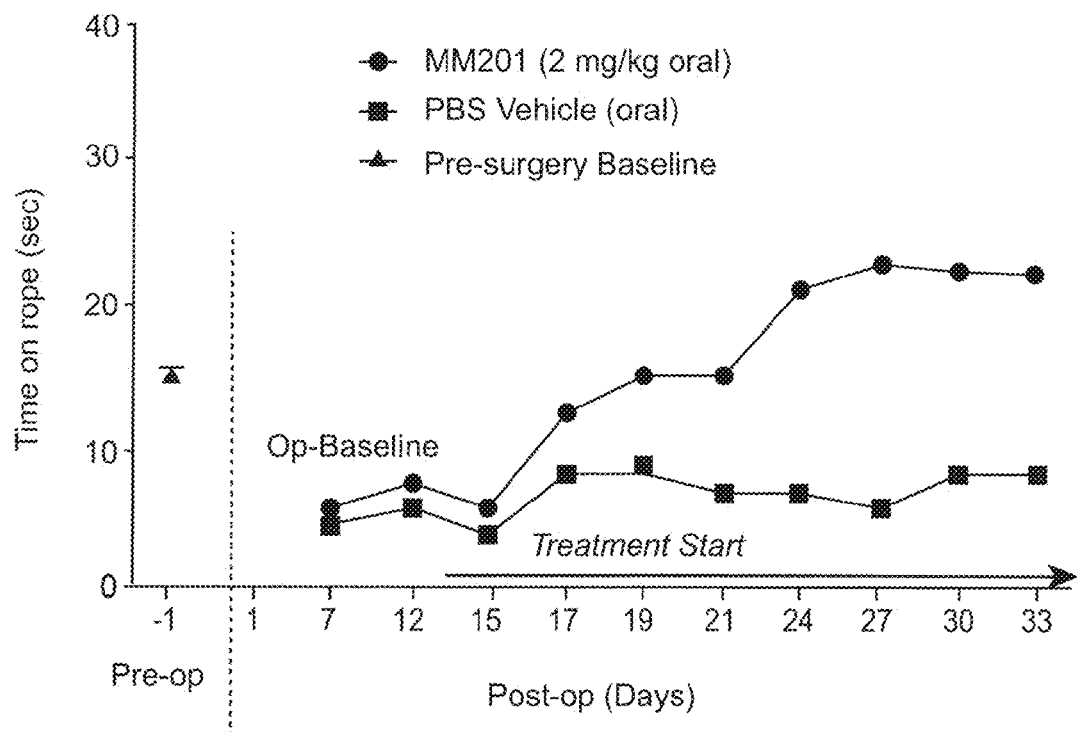
FIG. 49. Oral Dihexa reverses motor deficits in the 6-OHDA Rat. Baseline was calculated from 4 naïve animals to get the pre-op baseline for normal un-lesioned animals. 2 animals were lesioned with 6-OHDA in the right Hemisphere. 14 days post-op, treatment with vehicle started. 2 animals were lesioned with 6-OHDA in the right Hemisphere. 14 days post-op, treatment with Dihexa started. Animals were tested every other day. Dosing regimen (2 mg/kg by oral gavage/48 hrs).
Figure 50A:
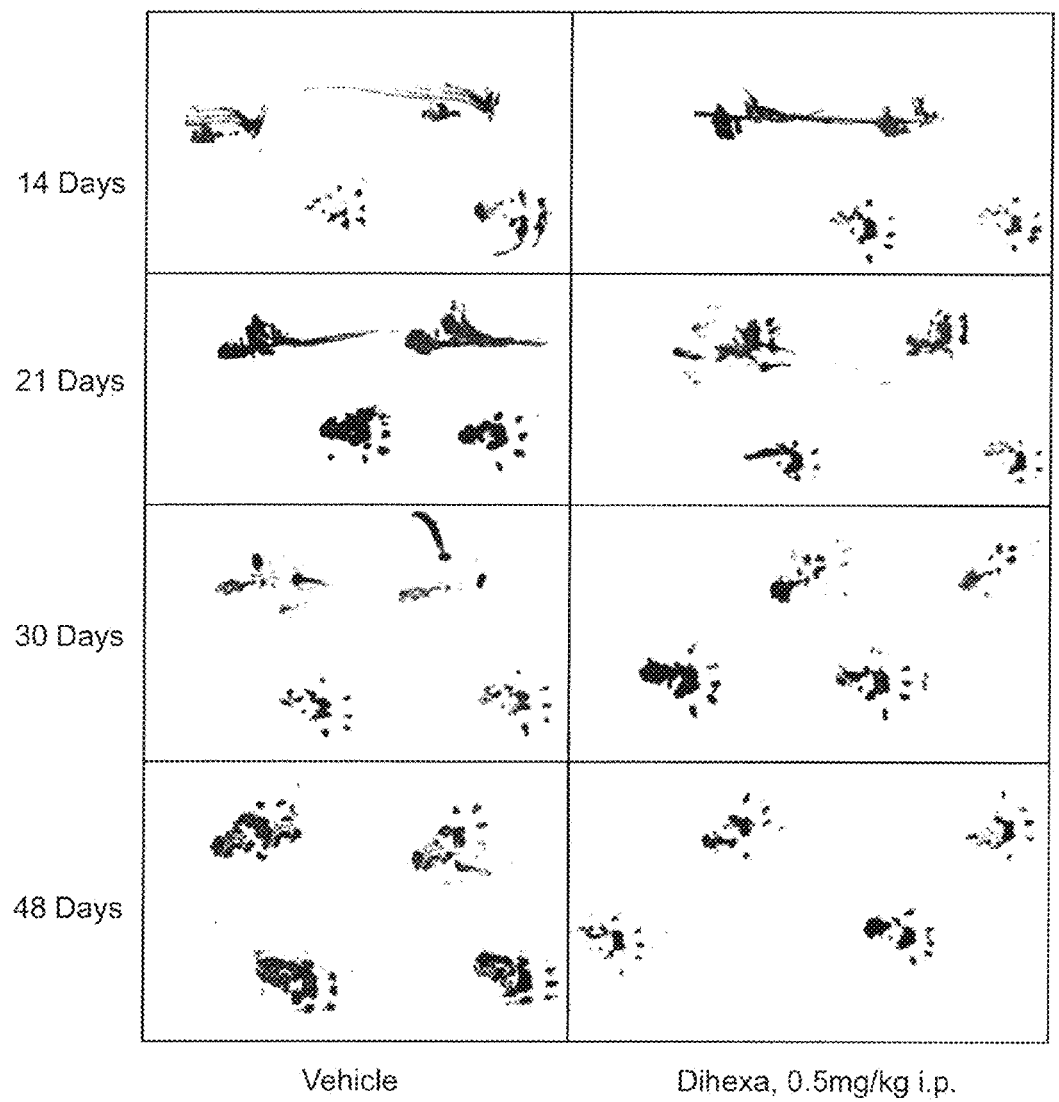
FIG. 50A, B and C. A: Step gait analysis of rats after 6-OHDA lesioning and treatment with Dihexa. B: Left stride analysis. C: Right stride analysis.
Figure 50B:
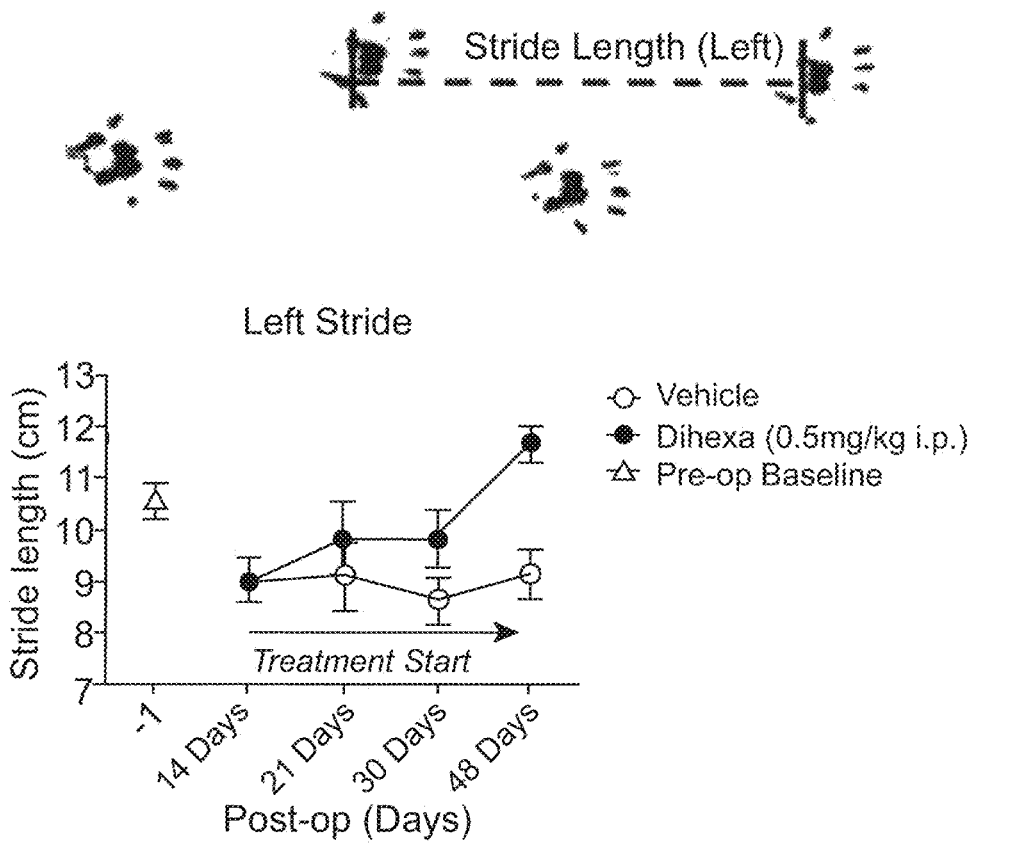
Figure 50C:
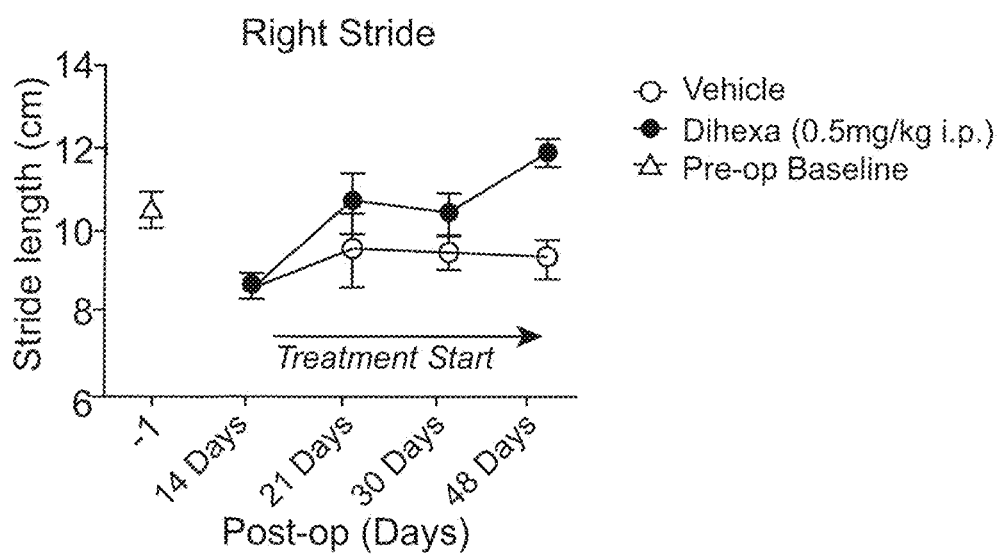

Directly relevant to its use as a PD therapeutic is the capacity of Dihexa to act synergistically to protect neurons from general growth factor deprivation (FIG. 46) and oxidative stress (FIG. 47), the underlying cause of neuronal cell death in PD. (Mounsey et al. *Parkinson's Disease* (20420080) 2011; Janda et al. *Mol Neurobiol Molecular Neurobiology* 2012) .Remarkably, Dihexa completely restores performance in the rope hang test in 6-OHDA lesioned rats after two weeks treatments when delivered by the intraperitoneal route (FIG. 48). This and additional blind studies suggest that this restoration of motor function is likely permanent having been observed out to three months post-lesioning. Similarly, gait analysis (FIGS. 49 and 50) confirmed the recovery of normal motor function over the same timeframe. Currently available histological data indicate a dramatic restoration of tyrosine hydroxylase (TH) staining in the substantia nigra (SN) following six weeks of ip Dihexa treatment, and three months of Dihexa treatment results in nearly 100% recovery of SN TH staining (see FIG. 32 of Example 4). This may be the underlying reason for motor function restoration. Significantly, no overt toxicity was noted during 96 day studies.

This Example demonstrates that the exemplary HGF mimic Dihexa can reverse Parkinsons' symptoms (e.g. motor abnormalities in gait, etc.) when administered to a mammal either ip or orally.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

The invention claimed is:

1. A method for slowing progression of dementia associated with Alzheimer's disease or Parkinson's disease in a subject in need thereof comprising the step of administering to said subject a therapeutic amount of hexanoic-tyrosine-isoleucine-(6)-amino-hexanoic amide.

* * * * *